(12) United States Patent
Wang et al.

(10) Patent No.: US 10,041,959 B2
(45) Date of Patent: Aug. 7, 2018

(54) MICRO-RNA, AUTOANTIBODY AND PROTEIN MARKERS FOR DIAGNOSIS OF NEURONAL INJURY

(71) Applicant: BANYAN BIOMARKERS, INC., Alachua, FL (US)

(72) Inventors: Kevin Ka-Wang Wang, Gainesville, FL (US); Zhiqun Zhang, Auburndale, MA (US); Ming-Cheng Liu, Plano, TX (US); Ronald L. Hayes, Alachua, FL (US); Jitendra Ramanlal Dave, Gaithersburg, MD (US)

(73) Assignees: Banyan Biomarkers, Inc., Alachua, FL (US); The United States of America, as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 15/391,755

(22) Filed: Dec. 27, 2016

(65) Prior Publication Data

US 2017/0242041 A1 Aug. 24, 2017

Related U.S. Application Data

(63) Continuation of application No. 13/395,931, filed as application No. PCT/US2010/048789 on Sep. 14, 2010.

(Continued)

(51) Int. Cl.
*G01N 33/53* (2006.01)
*C07K 16/18* (2006.01)
(Continued)

(52) U.S. Cl.
CPC ......... *G01N 33/6896* (2013.01); *C07K 16/18* (2013.01); *G01N 33/5308* (2013.01); *G01N 33/564* (2013.01); *G01N 2800/28* (2013.01)

(58) Field of Classification Search
None
See application file for complete search history.

(56) References Cited

U.S. PATENT DOCUMENTS 5,492,812 A 2/1996 Vooheis
6,589,746 B1 7/2003 Zemlan
(Continued)

FOREIGN PATENT DOCUMENTS

EP 1 992 688 11/2008
EP 2 143 735 1/2010
(Continued)

OTHER PUBLICATIONS

Adams et al., "The neuropathology of the vegetative state after an acute brain insult," Brain (2000) 123:1327-1338.
(Continued)

*Primary Examiner* — Jeffrey J Stucker
*Assistant Examiner* — Aurora M Fontainhas
(74) *Attorney, Agent, or Firm* — Morrison & Foerster LLP

(57) ABSTRACT

Processes and materials are provided for the detection, diagnosis, or determination of the severity of a neurological injury or condition, including traumatic brain injury, multiple-organ injury, stroke, Alzeimer's disease, Parkinson disease and Chronic Traumatic Encephalopathy (CTE). The processes and materials include biomarkers detected or measured in a biological sample such as whole blood, serum, plasma, or CSF. Such biomarkers include Tau and GFAP proteins, their proteolytic breakdown products, brain specific or enriched micro-RNA, and brain specific or enriched protein directed autoantibodies. The processes and materials are operable to detect the presence of absence of acute, subacute or chronic brain injuries and predict outcome for the brain injury.

11 Claims, 36 Drawing Sheets

Related U.S. Application Data

(60) Provisional application No. 61/242,123, filed on Sep. 14, 2009, provisional application No. 61/354,504, filed on Jun. 14, 2010, provisional application No. 61/355,779, filed on Jun. 17, 2010, provisional application No. 61/380,158, filed on Sep. 3, 2010.

(51) Int. Cl.
*C12Q 1/68* (2018.01)
*G01N 33/68* (2006.01)
*G01N 33/564* (2006.01)

(56) References Cited

U.S. PATENT DOCUMENTS

| | | |
|---|---|---|
| 7,014,854 B2 | 3/2006 | Jackowski et al. |
| 7,144,708 B2 | 12/2006 | Janigro et al. |
| 7,291,710 B2 | 11/2007 | Hayes et al. |
| 7,396,654 B2 | 7/2008 | Hayes et al. |
| 7,456,027 B2 | 11/2008 | Wang et al. |
| 8,298,835 B2 | 10/2012 | Wang et al. |
| 8,492,107 B2 | 7/2013 | Wang et al. |
| 2003/0199000 A1 | 10/2003 | Valkirs et al. |
| 2004/0121343 A1 | 6/2004 | Buechler et al. |
| 2004/0203083 A1 | 10/2004 | Buechler et al. |
| 2004/0253637 A1 | 12/2004 | Buechler et al. |
| 2005/0260697 A1 | 11/2005 | Wang et al. |
| 2007/0042425 A1 | 2/2007 | Hochstrasser et al. |
| 2009/0068691 A1 | 3/2009 | Dave et al. |
| 2009/0087868 A1 | 4/2009 | Wang et al. |
| 2011/0082203 A1 | 4/2011 | Wang et al. |
| 2011/0143375 A1 | 6/2011 | Wang et al. |
| 2011/0177974 A1 | 7/2011 | Wang et al. |
| 2012/0202231 A1 | 8/2012 | Wang et al. |
| 2013/0022982 A1 | 1/2013 | Wang et al. |
| 2013/0029362 A1 | 1/2013 | Jeromin et al. |
| 2013/0029859 A1 | 1/2013 | Svetlov et al. |
| 2014/0024053 A1 | 1/2014 | Kobeissy et al. |
| 2014/0275294 A1 | 9/2014 | Svetlov et al. |
| 2014/0303041 A1 | 10/2014 | Hayes et al. |
| 2014/0342381 A1 | 11/2014 | Hayes |
| 2015/0141528 A1 | 5/2015 | Larner |
| 2015/0259740 A1 | 9/2015 | Pollard et al. |
| 2015/0268252 A1 | 9/2015 | Svetlov et al. |

FOREIGN PATENT DOCUMENTS

| | | |
|---|---|---|
| JP | 2002-524740 | 8/2002 |
| JP | 2003-503314 | 1/2003 |
| JP | 2003-185657 | 7/2003 |
| JP | 2007-535318 | 12/2007 |
| JP | 2011-511301 | 4/2011 |
| WO | WO-00/014546 | 3/2000 |
| WO | WO-2000/78807 | 12/2000 |
| WO | WO-02/093174 | 11/2002 |
| WO | WO-03/016910 | 2/2003 |
| WO | WO-03/032894 | 4/2003 |
| WO | WO-04/025298 | 3/2004 |
| WO | WO-04/059293 | 7/2004 |
| WO | WO-04/078204 | 9/2004 |
| WO | WO-05/029087 | 3/2005 |
| WO | WO-05/029088 | 3/2005 |
| WO | WO-05/106038 | 11/2005 |
| WO | WO-05/113798 | 12/2005 |
| WO | WO-07/007129 | 1/2007 |
| WO | WO-07/046811 | 4/2007 |
| WO | WO-07/140188 | 12/2007 |
| WO | WO-2007/094395 | 7/2009 |
| WO | WO-09/100131 | 8/2009 |
| WO | WO-10/019553 | 2/2010 |
| WO | WO-10/059242 | 5/2010 |
| WO | WO-10/148391 | 12/2010 |
| WO | WO-11/032155 | 3/2011 |
| WO | WO-11/123844 | 10/2011 |
| WO | WO-11/160096 | 12/2011 |

OTHER PUBLICATIONS

Arnaud et al., "Proteasome-caspase-cathepsin sequence leading to tau pathology induced by prostaglandin J2 in neuronal cells," J Neurochem (2009) 110(1):328-342.
Avila et al., "Assembly in vitro of tau protein and its implications in Alzheimer's disease," Curr Alzheimer Res (2004) 1(2):97-101.
Baldwin et al., "Intermediate filament change in astrocytes following mild cortical contusion," Glia (1996) 16(3):266-275.
Bartus, "The calpain hypothesis of neurodegeneration: evidence for a common cytotoxic pathway," The Neuroscientist (1997) 3:314-327.
Beer et al., "Temporal Profile and Cell Subtype Distribution of Activated Caspase-3 Following Experimental Traumatic Brain Injury," J Neurochem (2000) 75:1264-1273.
Belay et al., Creutzfeldt-Jakob Disease in Unusually Young Patients Who Consumed Venison, Arch. Neurol "2001" 58(10):1673-1678.
Binder et al., "The Distribution of Tau in the Mammalian Central Nervous System," J Cell Biol (1985)101:1371-1378.
Bitsch et al., "Serum Tau Protein Level as a Marker of Axonal Damage in Acute Ischemic Stroke," Eur Neurol (2002) 47(1):45-51.
Bramlett et al., "Quantitative structural changes in white and gray matter 1 year following traumatic brain injury in rats," Acta Neuropathologica (2002) 103:607-614.
Buki et al., "The role of calpain-mediated spectrin proteolysis in traumatically induced axonal injury," J Neuropathol Exp Neurol (1999) 58:365-375.
Buki et al., "Cytochrome c Release and Caspase Activation in Traumatic Axonal Injury," J Neurosci (2000) 20(8):2825-2834.
Canu et al., "Tau Cleavage and Dephosphorylation in Cerebellar Granule Neurons Undergoing Apoptosis," J Neurosci (1998) 18(18):7061-7074.
Chekhonin et al., "Enzyme immunoassay of antibodies to neurospecific proteins in examination of blood-brain barrier function," Immunologiya (1996) 0(2):67-69.
Chiesa et al., "Extracellular calcium deprivation in astrocytes: regulation of mRNA expression and apoptosis," J Neurochem (1998) 70(4):1474-1483.
Christman et al., "Ultrastructural Studies of Diffuse Axonal Injury in Humans." J Neurotrauma (2009) 11:173-186.
Chung et al., "Proapoptotic Effects of Tau Cleavage Product Generated by Caspase-3," Neurobiol Dis (2001) 8(1):162-172.
Clark et al., "Caspase-3 Mediated Neuronal Death After Traumatic Brain Injury in Rats," J Neurochem (2000) 74(2):740-753.
Cotman et al., "The Role of Caspase Cleavage of Tau in Alzheimer Disease Neuropathology," J Neuropathol Exp Neurol (2005) 64(2): 104-112.
Dambinova, S. et al. "The presence of autoantibodies to N-terminus domain of GluR1 subunit of AMPA receptor in the blood serum of patients with epilepsy", J Neurol Sci (1997) 152(1):93-97.
Dambinova, S. et al. "Blood Test Detecting Autoantibodies to N-Methyl-D-aspartate Neuroreceptors for Evaluation of Patients with Transient Ischemic Attack and Stroke", Clin Chem (2003) 49(10):1752-1762.
Delobel et al., "Proteasome inhibition and Tau proteolysis: an unexpected regulation," FEBS Lett (2005) 579(1):1-5.
Dixon et al., "A controlled cortical impact model of traumatic brain injury in the rat," J Neurosci Methods (1991) 39(3):253-262.
Drubin et al., "Tau Protein Function in Living Cells," J Cell Biol (1986) 103(6):2739-2746.
El-Fawal et al., "Autoantibodies to neurotypic and gliotypic proteins as biomarkers of neurotoxicity: assessment of trimethyltin (TMT)," Neurotoxicology (2008) 29(1):109-115.
El-Hefnawy et al., "Characterization of Amplifiable, Circulating RNA in Plasma and Its Potential as a Tool for Cancer Diagnostics," Clinical Chem (2004) 50(3):564-573.
Foerch et al., "Serum glial fibrillary acidic protein as a biomarker for intracerebral hemorrhage in patients with acute stroke," J Neurol Neurosurg Psychiatry (2006) 77:181-184.
Franz et al., "Amyloid beta 1-42 and tau in cerebrospinal fluid after severe traumatic brain injury," Neurology (2003) 60(9):1457-1461.

(56) References Cited

OTHER PUBLICATIONS

Gabbita et al., "Cleaved-Tau: A Biomarker of Neuronal Damage after Traumatic Brain Injury," J Neurotrauma (2005) 22(1):83-94.
Gale et al., "Nonspecific white matter degeneration following traumatic brain injury," J Int Neuropsychol Soc (1995) 1:17-28.
Gamblin et al., "Caspase cleavage of tau: Linking amyloid and neurofibrillary tangles in Alzheimer's disease," Proc Natl Acad Sci USA (2003) 100(17):10032-10037.
Garcia et al., "Going new places using an old MAP: tau, microtubules and human neurodegenerative disease" Curr Opin Cell Biol (2001) 13(1):41-48.
Garcia-Sierra et al., "Truncation of Tau Protein and its Pathological Significance in Alzheimer's Disease," J Alzheimers Dis (2008) 14(4):401-409.
Gaskin et al., "Patients with clinically diagnosed senile dementia of the Alzheimer type make autoantibodies that react with neurofibrillary tangles," Clinical Research (1986) 34(2): 669A.
Gorman et al., "Analysis of acetylcholine release following concussive brain injury in the rat," J Neurotrauma (1989) 6:203.
Goryunova et al., "Glutamate Receptor Autoantibody Concentrations in Children with Chronic Post-Traumatic Headache," Neuroscience and Behavioral Physiology (2007) 37(8):761-764.
Guillozet-Bongaarts et al., "Tau truncation during neurofibrillary tangle evolution in Alzheimer's disease," Neurobiol Aging (2005) 26(7):1015-1022.
Hackeng et al., "Total chemical synthesis of enzymatically active human type II secretory phospholipase A2," Proc Natl Acad Sci U S A (1997) 94(15):7845-7850.
Hamaoui et al., "Real-Time Quantitative PCR Measurement of Circulatory Rhodopsin mRNA in Healthy Subjects and Patients with Diabetic Retinopathy," Annals of the New York Academy of Sciences (2004) 1022:152-156.
Hasselmann et. al., "Extracellular Tyrosinase mRNA within Apoptotic Bodies is Protected from Degradations in Human Serum," Clinical Chemistry (2001) 47(8):1488-1489.
Herrmann et al., "Release of Glial Tissue-Specific Proteins After Acute Stroke: A comparative analysis of serum concentrations of protein S-100B and glial fibrillary acidic protein," Stroke (2000) 31(11):2670-2677.
Higuchi et al., "Tau and axonopathy in neurodegenerative disorders," Neuromolecular Med (2002) 2(2):131-150.
Hozumi et al., "GFAP mRNA levels following stab wounds in rat brain," Brain Res (1990) 534(1-2):291-294.
Jeyaseelan et al., "MicroRNA expression in the blood and brain of rats subjected to transient focal ischemia by middle cerebral artery occlusion," Stroke (2008) 39(3):959-966.
Johnson et al., "Proteolysis of Tau by Calpain," Biochem Biophys Res Commun (1989) 163(3):1505-1511.
Kampfl et al., "Mechanisms of Calpain Proteolysis Following Traumatic Brain Injury: Implications for Pathology and Therapy: A Review and Update," J Neurotrauma (1997) 14(3):121-134.
Kiraly et al., "Traumatic Brain Injury and Delayed Sequelae: A Review—Traumatic Brain Injury and Mild Traumatic Brain Injury (Concussion) are Precursors to Later-Onset Brain Disorders, Including Early-Onset Dementia," Scientific World Journal (2007) 12(7):1768-1776.
Knoblach et al., "Multiple Caspases Are Activated after Traumatic Brain Injury: Evidence for Involvement in Functional Outcome," J Neurotrama (2002) 19(10):1155-1170.
Kobeissy et al. "Novel differential neuroproteomics analysis of traumatic brain injury in rats, " Mol Cell Proteomics (2006) 5(10):1887-1898.
Kosik et al., "MAP2 and Tau Segregate into Dendritic and Axonal Domains After the Elaboration of Morphologically Distinct Neurites: An Immunocytochemical Study of Cultured Rat Cerebrum," J Neurosci (1987) 7(10):3142-3153.
Koumura et al., "A novel calpain inhibitor, ((1S)-1 ((((1S)-1-benzyl-3-cyclopropylamino-2,3-di-oxopropyl)amino)carbonyl)-3-methylbutyl) carbamic acid 5-methoxy-3-oxapentyl ester, protects neuronal cells from cerebral ischemia-induced damage in mice," Neuroscience (2008) 157(2):309-318.
Kovesdi et al., "Update on protein biomarkers in traumatic brain injury with emphasis on clinical use in adults and pediatrics", Acta Neurochirurgica (2010) 152(1):1-17.
Krishnamurthy et al., "Molecular and biologic markers of premalignant lesions of human breast," Adv Anat Pathol (2002) 9(3):185-197.
Kumagae et al., "Output, Tissue Levels, and Synthesis of Acetylcholine During and After Transient Forebrain Ischemia in the Rat," J Neurochem (1991) 56(4):1169-1173.
Lamers et al., "Protein S-100b, Neuron-Specific Enolase (NSE), Myelin Basic Protein (MBP) and Glial Fibrillary Acidic Protein (GFAP) in Cerebrospinal Fluid (CSF) and Blood of Neurological Patients," Brain Res Bull (2003) 61(3): 261-264.
Le Prince et al., "Alterations of glial fibrillary acidic protein mRNA level in the aging brain and in senile dementia of the Alzheimer type," Neurosci Lett (1993) 151(1):71-73.
Lee et al., "Rapid increase in immunoreactivitiy to GFAP in astrocytes in vitro induced by acidic pH is mediated by calcium influx and calpain I," Brain Research (2000) 864(2): 220-229.
Lee et al., "Fit-for-Purpose Method Development and Validation for Successful Biomarker Measurement," Pharm Res (2006) 23(2):312-328.
Lei et al., "Microarray based analysis of microRNA expression in rat cerebral cortex after traumatic brain injury," Brain Res (2009) 1284:191-201.
Leon et al., "Free DNA in the Serum of Cancer Patients and the Effect of Therapy," Patients Cancer Research (1977) 37:646-650.
Litersky et al., "Phophorylation, calpain proteolysis and tubulin binding of recombinant human tau isoforms," Brain Res (1993) 604:32-40.
Liu et al., "Altered microRNA expression following traumatic spinal cord injury," Exp Neurol (2009) 219(2):424-429.
Lo et. al., "Presence of fetal DNA in maternal plasma and serum," The Lancet (1997) 350:485-487.
Lumpkins et al., "Glial Fibrillary Acidic Protein is Highly Correlated With Brain Injury," J Trauma (2008) 65(4):778-782.
Lyeth et al., "Effects of anticholinergic treatment on transient behavioral suppression and physiological responses following concussive brain injury to the rat," Brain Res (1988) 448:88-97.
Lyeth et al., "Effects of scopolamine treatment on long-term behavioral deficits following concussive brain injury to the rat," Brain Res (1988) 452:39-48.
Leyth et al., "Cholinergic and opioid mediation of traumatic brain injury," J Neurotrauma (1992) 9(Suppl 2): S463-474.
Lyeth et al., "Hypothermia blunts acetylcholine increase in CSF of traumatically brain injured rats," Mol Chem Neuropathol (1993) 18(3):247-256.
Lyeth et al., "Combined scopolamine and morphine treatment of traumatic brain injury in the rat," Brain Res (1993) 617:69-75.
Mao et al., "The value of serum myelin basic protein in assessment of severity of acute closed head trauma," Hua Xi Yi Ke Da Xue Bao (1995) 26(2):135-137 (Abstract).
Martinez et al., Granulomatous Amebic Encephalitis in a Patient with AIDS: Isolation of *Acanthamoeba* sp. Group II from Brain Tissue and Successful Treatment with Sulfadiazine and Fluconazole, J Clin Microbiol (2000) 38(10):3892-3895.
McCraken et al., "Calpain activation and cytoskeletal protein breakdown in the corpus callosum of head-injured patients," J Neurotrauma (1999) 16(9):749-761.
McGinnis et al., "Procaspase-3 and poly(ADP)ribose polymerase (PARP) are calpain substrates," Biochem Biophys Res Commun (1999) 263(1):94-99.
Mcintosh et al., "Neuropathological sequelae of traumatic brain injury: relationship to neurochemical and biomechanical mechanisms," Lab Invest (1996) 74:315-341.
Mckee et al., "Chronic traumatic encephalopathy in athletes: progressive tauopathy following repetitive head injury," J Neuropathol Exp Neurol (2009) 68(7):709-735.
Mclendon et al., "Immunohistochemistry of the glial fibrillary acidic protein: basic and applied considerations," Brain Pathol (1994) 4(3):221-228.

(56) References Cited

OTHER PUBLICATIONS

Medana et al., "Axonal damage: a key predictor of outcome in human CNS diseases," Brain (2003) 126(3):515-530.
Menke et al., "Improved Conditions for Isolation and Quantification of RNA in Urine Specimens," Annals of the New York Academy of Sciences (2004) 1022:185-189.
Missler et al., "Measurement of Glial Fibrillary Acidic Protein in Human Blood: Analytical Method and Preliminary Clinical Results," Clin Chem (1999) 45(1):138-141.
Mizuno et al., "Mitochondrial dysfunction in parkinson's disease," Annals of Neurology (1998) 44(S1):S99-S109.
Morozov et al., "Autoantibodies against nerve tissue proteins long after cranio-cerebral injury," Vopr Med Khim (1996) 42(2):147-152 (Abstract).
Mouser et al., "Caspase-Mediated Cleavage of Glial Fibrillary Acidic Protein within Degenerating Astrocytes of the Alzheimer's Disease Brain," Am J Pathol (2003 168(3):936-946.
Muller et. al., "Methylated DNA as a possible screening marker for neoplastic disease in several body fluids," Expert Review of Molecular Diagnostics (2003) 3(4):443-458.
Nath et al., "Effects of ICE-like protease and calpain inhibitors on neuronal apoptosis," Neuroreport (1996) 8(1):249-255.
Nath et al., "Evidence for Activation ofCaspase-3-Like Protease in Excitotoxin- and Hypoxia/Hypoglycemia- Injured Neurons," J Neurochem (1998) 71:186-195.
Nawashiro et al., "Selective vulnerability of hippocampal CA3 neurons to hypoxia after mild concussion in the rat," Neurol Res (1995) 17(6):455-460.
Newcomb et al., "Immunohistochemical study of calpain-mediated breakdown products to alpha-spectrin following controlled cortical impact injury in the rat," J Neurotrauma (1997) 14(6):369-383.
Ng et al., "The pathological spectrum of diffuse axonal injury in blunt head trauma: assessment with axon and myelin strains," Clin Neurol Neurosurg (1994) 96:24-31.
Nylen et al., "Increased serum-GFAP in patients with severe traumatic brain injury is related to outcome," J Neurol Sci (2006) 240(1-2):85-91.
Oka et al., "Amelioration of retinal degeneration and proteolysis in acute ocular hypertensive rats by calpain inhibitor ((1S)-1-((((1S)-1-benzyl-3-cyclopropylamino-2,3-di-oxopropyl)amino)carbonyl)-3-methylbutyl)carbamic acid 5-methoxy-3-oxapentyl ester," Neuroscience (2006) 141(4):2139-2145.
Olney et al., "Seizure-related brain damage induced by cholinergic agents," Nature (1983) 301,:520-522.
Papa et al., "Use of biomarkers for diagnosis and management of traumatic brain injury patients," Expert Opin Med Diagn (2008) 2(8):937-945.
Papa et al., "Elevated Levels of Serum Glial Fibrillary Acidic Protein Breakdown Products in Mild and Moderate Traumatic Brain Injury are Associated With Intracranial Lesions and Neurosurgical Intervention," Ann Emerg Med (2011) 59(6):471-483.
Park et al., "The generation of a 17 kDa neurotoxic fragment: an alternative mechanism by which tau mediates beta-amyloid-induced neurodegeneration," J Neurosci (2005) 25(22):5365-5375.
Pattyn et al., "RTPrimerDB: the Real-Time PCR primer and probe database," Nucleic Acids Res (2003) 31(1):122-123.
Pelinka et al., "Glial Fibrillary Acidic Protein in Serum After Traumatic Brain Injury and Multiple Trauma," J Trauma (2004) 57(5):1006-1012.
Petricoin et al., "Clinical proteomics: translating benchside promise into bedside reality," Nat Rev Drug Discov (2002) 1(9):683-695.
Pettus et al., "Traumatically induced altered membrane permeability: its relationship to traumatically induced reactive axonal change," J Neurotrauma (1994) 11(5):507-522.
Pike et. al., "Temporal relationships between de nova protein synthesis, calpain and caspase 3-like protease activation, and DNA fragmentation during apoptosis," J. Neurosci Res (1998) 52(5):505-520.
Pike et al., "Regional calpain and caspase-3 proteolysis of alpha-spectrin after traumatic brain injury," NeuroReport (1998) 9(11):2437-2442.
Pike et al., "Accumulation of Calpain and Caspase-3 Proteolytic Fragments of Brain-Derived alpha-II-Spectrin in Cerebral Spinal Fluid After Middle Cerebral Artery Occlusion in Rats," J Cereb Blood Flow Metab (2004) 24(1):98-106.
Pogue et al., "Micro RNA-125b (miRNA-125b) function in astrogliosis and glial cell proliferation," Neurosci Lett (2010) 476(1):18-22.
Posmantur et al. "A calpain inhibitor attenuates cortical cytoskeletal protein loss after experimental traumatic brain injury in the rat," Neuroscience (1997) 77(3):875-888.
Rainer et al., "Effects of Filtration on Glyceraldehyde-3-Phosphate Dehydrogenase mRNA in the Plasma of Trauma Patients and Healthy Individuals," Clinical Chemistry (2004) 50(1):206-208.
Rainer et al., "Prognostic Use of Circulating Plasma Nucleic Acid Concentrations in Patients with Acute Stroke," Clin Chem (2003) 49(4):562-569.
Rao et al., "Marked calpastatin (CAST) depletion in Alzheimer's disease accelerates cytoskeleton disruption and neurodegeneration: neuroprotection by CAST overexpression," J Neurosci (2008) 28(47):12241-12254.
Redell et al., "Traumatic brain injury alters expression of hippocampal microRNAs: Potential regulators of multiple pathophysiological processes," J Neurosci Res (2009) 87(6):1435-1448.
Rissman et al., "Caspase-cleavage of tau is an early event in Alzheimer disease tangle pathology," J Clin Invest (2004) 114:121-130.
Robinson et al., "The effect of $M_1$ muscarinic blockade on behavior and physiological responses following traumatic brain injury in the rat," Brain Res (1990) 511:141-148.
Rohn et al., "Caspase-9 Activation and Caspase Cleavage of tau in the Alzheimer's Disease Brain," Neurobiol Dis (2002) 11(2):341-354.
Rudehill et al., "Autoreactive antibodies against neurons and basal lamina found in serum following experimental brain contusion in rats," Acta Neurochirurgica (2006) 148(2):199-205.
Saatman et al., "Prolonged calpain-mediated spectrin breakdown occurs regionally following experimental brain injury in the rat," J Neuropathol Exp Neurol (1996) 55:850-860.
Saatman et al., "Calpain inhibitor AK295 attenuates motor and cognitive deficits following experimental brain injury in the rat," Proc Natl Acad Sci USA (1996) 93(8):3428-3433.
Saatman et al., "Behavioral efficacy of posttraumatic calpain inhibition is not accompanied by reduced spectrin proteolysis, cortical lesion, or apoptosis," J Cereb Blood Flow Metab (2000) 20(1):66-73.
Shimohama et al., "Changes in caspase expression in Alzheimer's disease: comparison with development and aging," Biochem Biophys Res Commun (1999) 256(2):381-384.
Shirasaki et al., "Exploration of orally available calpain inhibitors: peptidyl alpha-ketoamides containing an amphiphile at P3 site," Bioorg Med Chem (2005) 13(14):4473-4484.
Silva et al., "Presence of Tumor DNA in Plasma of Breast Cancer Patients: Clinicopathological Correlations," Cancer Research (1999) 59:3251-3256.
Siman et al., "Proteins released from degenerating neurons are surrogate markers for acute brain damage," Neurobiol Dis (2004) 16(2):311-320.
Singh et al., "Detection of brain autoantibodies in the serum of patients with Alzheimer's disease but not Down's syndrome," Immunol Lett (1986) 12(5-6):277-280.
Sinjoanu et al., "The novel calpain inhibitor A-705253 potently inhibits oligomeric beta-amyloid-induced dyanmin 1 and tau cleavage in hippocampal neurons," Neurochem Int (2008) 53(3-4):79-88.
Skoda et al., "Antibody formation against beta-tubulin class III in response to brain trauma," Brain Research Bulletin (2006) 68(4):213-216.
Sorokina et al., "Autoantibodies to glutamate receptors and metabolic products of nitric oxide in blood serum of children in the acute period of brain trauma," Zh Nevrol Psikhiatr Im S S Korsakova (2008) 108(3):67-72.

(56) References Cited

OTHER PUBLICATIONS

Taback et al., "Circulating Nucleic Acids and Proteomics of Plasma/Serum Clinical Utility," Annals of the New York Academy of Sciences (2004) 1022:1-8.
Tan et al., "Deoxyribonucleic Acid (DNA) and Antibodies to DNA in the Serum of Patients with Systemic Lupus Erythematosus," Journal of Clinical Investigation (1966) 45(11):1732-1740.
Tanriverdi et al., "Antipituitary antibodies after traumatic brain injury: is head trauma-induced pituitary dysfunction associated with autoimmunity?" Eur J of Endocrinol (2008) 159(1):7-13.
Terryberry et al., "Autoantibodies in Neurodegenerative Diseases: Antigen-Specific Frequencies and Intrathecal Analysis," Neurobiology of Aging (1998) 19(3):205-216.
Terryberry et al., "Clinical Utility of Autoantibodies in Guillain-Barre Syndrome and Its Variants," Clinical Reviews in Allergy and Immunology (1998) 16:265-273.
Turski et al., "Cholinomimetics produce seizures and brain damage in rats," Experientia (1983) 39(12):1408-1411.
Uryu et. al., "Multiple proteins implicated in neurodegenerative diseases accumulate in axons after brain trauma in humans", Exp Neurol (2007) 208(2):185-192.
Van Den Heuvel et al., "Traumatic brain injury and Alzheimer's disease: a review," Prog Brain Res (2007) 161:303-316.
Van Geel et al., "Measurement of glial fibrillary acidic protein in blood: an analytical method," Clin Chim Acta (2002) 326(1-2):151-154.
Vissers et al., "Rapid immunoassay for the determination of glial fibrillary acidic protein (GFAP) in serum," Clin Chim Acta (2006) 366(1-2):336-340.
Vos et al., "Glial and neuronal proteins in serum predict outcome after severe traumatic brain injury," Neurology (2004) 62(8):1303-1310.
Wang et al., "Calpain and caspase: can you tell the difference?" Trends Neurosci (2000) 23(1):20-26.
Wang et al.," A study of HSP70 and NF in brain contusion timing," Fa Yi Xue Za Zhi (2000) 16(3):132-134 (Abstract).
Warren et al., "Concurrent calpain and caspase-3 mediated proteolysis of alphaII-spectrin and tau in rat brain after methamphetamine exposure: A similar profile to traumatic brain injury," Life Sciences (2005) 78(3):301-309.
Warren et al., "Calpain-and caspase-mediated all-spectrin and tau proteolysis in rat cerebrocortical neuronal cultures after ecstasy or methamphetamine exposure," Intl J Neuro-Psychopharmacology (2007) 10(4):479-490.
Waterhouse et al., "Heteronuclear ribonucleoproteins C1 and C2, components of the spliceosome, are specific targets of interleukin 1 beta-converting enzyme-like proteases in apoptosis," J Biol Chem (1996) 271(46):29335-29341.
Watts et al., "A human fetal monoclonal DNA-binding antibody shares idiotypes with fetal and adult murine monoclonal DNA-binding antibodies," Immunology (1990) 69(3):348-354.
Yang et al., "Calpain-Induced Proteolysis of Normal Human Tau and Tau Associated with Paired Helical Filaments," Eur J Biochem (1995) 223(1):9-17.
Ye et al., "Synthetic antibodies for specific recognition and crystallization of structured RNA," Proc Natl Acad Sci U S A (2008) 105(1):82-7.
Yen et al., "FTDP-17 tau mutations decrease the susceptibility of tau to calpain I digestion," FEBS Lett (1999) 461(1):91-95.
Yoshiyama et al., "Enhanced neurofibrillary tangle formation, cerebral atrophy, and cognitive deficits induced by repetitive mild brain injury in a transgenic tauopathy mouse model" J Neurotrama (2005) 22(10):1134-1141.
Zemlan et al., "C-tau biomarker of neuronal damage in severe brain injured patients: association with elevated intracranial pressure and clinical outcome," Brain Res (2002) 947(1):131-139.
Zemlan et al., "Quantification and localization of kainic acid-induced neurotoxicity employing a new biomarker of cell death: cleaved microtubule associated protein-tau (C-tau)," Neuroscience (2003) 121(2):399-409.
Zhang et al., "Inhibition of autophagy causes tau proteolysis by activating calpain in rat brain," J Alzheimers Dis (2009)16(1):39-47.
Zhang et al., "Multiple alphaII-spectrin breakdown products distinguish calpain and caspase dominated necrotic and apoptotic cell death pathways," Apoptosis (2009) 14(11):1289-1298.

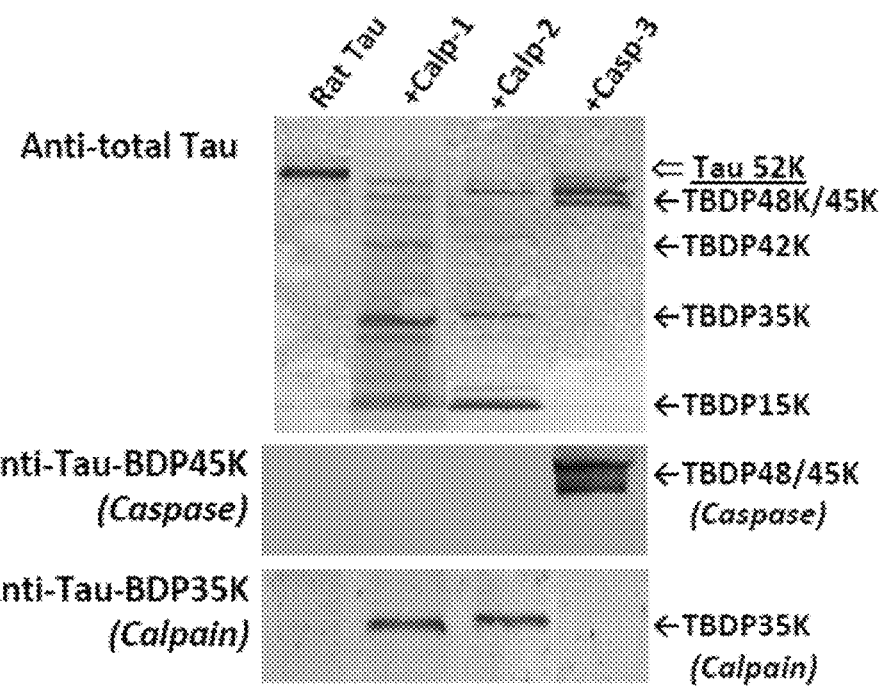

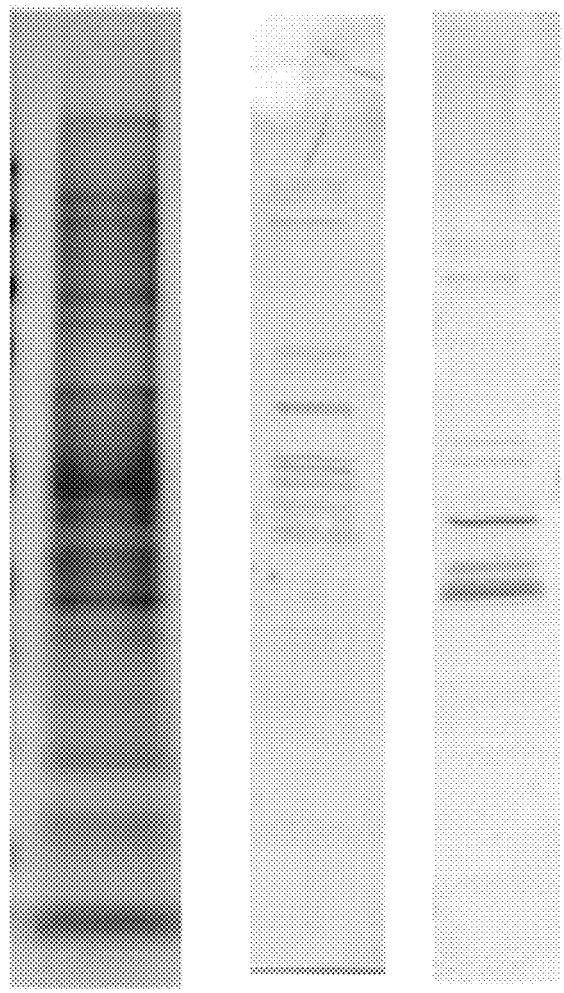

Autoantibody to human brain proteins: Yes (Y) or No (N)

SEQUENCE LISTING

```
<160> NUMBER OF SEQ ID NOS: 153

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ile Asp Met Val Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Asp Arg Thr Gly Asn
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ala Leu Asn Ala Gly Phe Lys Glu Thr Arg Ala Ser Glu Arg Ala
1               5                   10                  15

Glu

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Ile Pro Val Gln Thr Phe Ser Asn Leu Gln Ile Arg Glu Thr
```

<210> SEQ ID NO 5
<211> LENGTH: 432
<212> TYPE: PRT
<213> ORGANISM: Rattus norvegicus

<400> SEQUENCE: 5

```
Met Ala Glu Pro Arg Gln Glu Phe Asp Thr Met Glu Asp Gln Ala Gly
1               5                   10                  15

Asp Tyr Thr Met Leu Gln Asp Gln Glu Gly Asp Met Asp His Gly Leu
                20                  25                  30

Lys Glu Ser Pro Pro Gln Pro Ala Asp Asp Gly Ser Glu Glu Pro
                35                  40                  45

Gly Ser Glu Thr Ser Asp Ala Lys Ser Thr Pro Thr Ala Glu Asp Val
    50                  55                  60

Thr Ala Pro Leu Val Glu Glu Arg Ala Pro Asp Lys Gln Ala Thr Ala
65                  70                  75                  80

Gln Ser His Thr Glu Ile Pro Glu Gly Thr Thr Ala Glu Glu Ala Gly
                85                  90                  95

Ile Gly Asp Thr Pro Asn Met Glu Asp Gln Ala Ala Gly His Val Thr
                100                 105                 110

Gln Ala Arg Val Ala Gly Val Ser Lys Asp Arg Thr Gly Asn Asp Glu
            115                 120                 125

Lys Lys Ala Lys Gly Ala Asp Gly Lys Thr Gly Ala Lys Ile Ala Thr
130                 135                 140

Pro Arg Gly Ala Ala Thr Pro Gly Gln Lys Gly Thr Ser Asn Ala Thr
145                 150                 155                 160

Arg Ile Pro Ala Lys Thr Thr Pro Ser Pro Lys Thr Pro Pro Gly Ser
                165                 170                 175

Gly Glu Pro Pro Lys Ser Gly Glu Arg Ser Gly Tyr Ser Ser Pro Gly
                180                 185                 190

Ser Pro Gly Thr Pro Gly Ser Arg Ser Arg Thr Pro Ser Leu Pro Thr
            195                 200                 205

Pro Pro Thr Arg Glu Pro Lys Lys Val Ala Val Arg Thr Pro Pro
210                 215                 220

Lys Ser Pro Ser Ala Ser Lys Ser Arg Leu Gln Thr Ala Pro Val Pro
225                 230                 235                 240

Met Pro Asp Leu Lys Asn Val Arg Ser Lys Ile Gly Ser Thr Glu Asn
                245                 250                 255

Leu Lys His Gln Pro Gly Gly Gly Lys Val Gln Ile Ile Asn Lys Lys
                260                 265                 270

Leu Asp Leu Ser Asn Val Gln Ser Lys Cys Gly Ser Lys Asp Asn Ile
            275                 280                 285

Lys His Val Pro Gly Gly Gly Ser Val Gln Ile Val Tyr Lys Pro Val
        290                 295                 300

Asp Leu Ser Lys Val Thr Ser Lys Cys Gly Ser Leu Gly Asn Ile His
305                 310                 315                 320

His Lys Pro Gly Gly Gly Gln Val Glu Val Lys Ser Glu Lys Leu Asp
                325                 330                 335

Phe Lys Asp Arg Val Gln Ser Lys Ile Gly Ser Leu Asp Asn Ile Thr
            340                 345                 350

His Val Pro Gly Gly Gly Asn Lys Lys Ile Glu Thr His Lys Leu Thr
        355                 360                 365
```

```
Phe Arg Glu Asn Ala Lys Ala Lys Thr Asp His Gly Ala Glu Ile Val
            370                 375                 380

Tyr Lys Ser Pro Val Val Ser Gly Asp Thr Ser Pro Arg His Leu Ser
385                 390                 395                 400

Asn Val Ser Ser Thr Gly Ser Ile Asp Met Val Asp Ser Pro Gln Leu
                405                 410                 415

Ala Thr Leu Ala Asp Glu Val Ser Ala Ser Leu Ala Lys Gln Gly Leu
            420                 425                 430

<210> SEQ ID NO 6
<211> LENGTH: 12
<212> TYPE: PRT
<213> ORGANISM: Rattus norvegicus

<400> SEQUENCE: 6

Leu Lys Glu Ser Pro Pro Gln Pro Pro Ala Asp Asp
1               5                   10

<210> SEQ ID NO 7
<211> LENGTH: 20
<212> TYPE: PRT
<213> ORGANISM: Rattus norvegicus

<400> SEQUENCE: 7

Ala Gly His Val Thr Gln Ala Arg Met Val Ser Lys Asp Arg Thr Gly
1               5                   10                  15

Asn Asp Glu Lys
            20

<210> SEQ ID NO 8
<211> LENGTH: 21
<212> TYPE: PRT
<213> ORGANISM: Rattus norvegicus

<400> SEQUENCE: 8

Pro Thr Arg Glu Pro Lys Lys Val Ala Val Val Arg Thr Pro Pro Lys
1               5                   10                  15

Ser Pro Ser Ala Ser
            20

<210> SEQ ID NO 9
<211> LENGTH: 23
<212> TYPE: PRT
<213> ORGANISM: Rattus norvegicus

<400> SEQUENCE: 9

Lys Ile Glu Thr His Lys Leu Thr Phe Arg Glu Asn Ala Lys Ala Lys
1               5                   10                  15

Thr Asp His Gly Ala Glu Ile
            20

<210> SEQ ID NO 10
<211> LENGTH: 18
<212> TYPE: PRT
<213> ORGANISM: Rattus norvegicus

<400> SEQUENCE: 10

Ser Ser Thr Gly Ser Ile Asp Met Val Asp Ser Pro Gln Leu Ala Thr
1               5                   10                  15

Leu Ala
```

-continued

```
<210> SEQ ID NO 11
<211> LENGTH: 441
<212> TYPE: PRT
<213> ORGANISM: Homo sapiens

<400> SEQUENCE: 11

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380
```

```
Lys Thr Asp His Gly Ala Glu Ile Val Tyr Lys Ser Pro Val Ser
385                 390                 395                 400

Gly Asp Thr Ser Pro Arg His Leu Ser Asn Val Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 12
<211> LENGTH: 21
<212> TYPE: PRT
<213> ORGANISM: Homo sapiens

<400> SEQUENCE: 12

Ala Gly His Val Thr Gln Ala Arg Met Val Ser Lys Ser Lys Asp Gly
1               5                   10                  15

Thr Gly Ser Asp Asp
            20

<210> SEQ ID NO 13
<211> LENGTH: 21
<212> TYPE: PRT
<213> ORGANISM: Homo sapiens

<400> SEQUENCE: 13

Pro Thr Arg Glu Pro Lys Lys Val Ala Val Val Arg Thr Pro Pro Lys
1               5                   10                  15

Ser Pro Ser Ser Ala
            20

<210> SEQ ID NO 14
<211> LENGTH: 27
<212> TYPE: PRT
<213> ORGANISM: Homo sapiens

<400> SEQUENCE: 14

Gly Lys Thr Lys Ile Ala Thr Pro Arg Gly Ala Ala Pro Pro Gly Gln
1               5                   10                  15

Lys Gly Gln Ala Asn Ala Thr Arg Ile Thr Ala
            20                  25

<210> SEQ ID NO 15
<211> LENGTH: 12
<212> TYPE: PRT
<213> ORGANISM: Homo sapiens

<400> SEQUENCE: 15

Leu Lys Glu Ser Pro Leu Gln Thr Pro Thr Glu Asp
1               5                   10

<210> SEQ ID NO 16
<211> LENGTH: 23
<212> TYPE: PRT
<213> ORGANISM: Homo sapiens

<400> SEQUENCE: 16

Lys Ile Glu Thr His Lys Leu Thr Phe Arg Glu Asn Ala Lys Ala Lys
1               5                   10                  15

Thr Asp His Gly Ala Glu Ile
            20
```

<210> SEQ ID NO 17
<211> LENGTH: 14
<212> TYPE: PRT
<213> ORGANISM: Homo sapiens

<400> SEQUENCE: 17

Gly Asp Arg Lys Asp Gln Gly Gly Tyr Thr Met His Gln Asp
1               5                   10

<210> SEQ ID NO 18
<211> LENGTH: 18
<212> TYPE: PRT
<213> ORGANISM: Homo sapiens

<400> SEQUENCE: 18

Ser Ser Thr Gly Ser Ile Asp Met Val Asp Ser Pro Gln Leu Ala Thr
1               5                   10                  15

Leu Ala

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Asp Arg Thr Gly Asn Asp Glu Lys
1               5

<210> SEQ ID NO 20
<211> LENGTH: 10
<212> TYPE: PRT
<213> ORGANISM: Homo sapiens

<400> SEQUENCE: 20

Ser Ser Thr Gly Ser Ile Asp Met Val Asp
1               5                   10

<210> SEQ ID NO 21
<211> LENGTH: 8
<212> TYPE: PRT
<213> ORGANISM: Homo sapiens

<400> SEQUENCE: 21

Ser Pro Gln Leu Ala Thr Leu Ala
1               5

<210> SEQ ID NO 22
<211> LENGTH: 13
<212> TYPE: PRT
<213> ORGANISM: Rattus norvegicus

<400> SEQUENCE: 22

Ala Gly His Val Thr Gln Ala Arg Val Ala Gly Val Ser
1               5                   10

<210> SEQ ID NO 23
<211> LENGTH: 9
<212> TYPE: PRT
<213> ORGANISM: Rattus norvegicus

<400> SEQUENCE: 23

```
Lys Asp Arg Thr Gly Asn Asp Glu Lys
1               5

<210> SEQ ID NO 24
<211> LENGTH: 11
<212> TYPE: PRT
<213> ORGANISM: Homo sapiens

<400> SEQUENCE: 24

Pro Thr Arg Glu Pro Lys Lys Val Ala Val Val
1               5                   10

<210> SEQ ID NO 25
<211> LENGTH: 10
<212> TYPE: PRT
<213> ORGANISM: Homo sapiens

<400> SEQUENCE: 25

Arg Thr Pro Pro Lys Ser Pro Ser Ala Ser
1               5                   10

<210> SEQ ID NO 26
<211> LENGTH: 10
<212> TYPE: PRT
<213> ORGANISM: Homo sapiens

<400> SEQUENCE: 26

Lys Ile Glu Thr His Lys Leu Thr Phe Arg
1               5                   10

<210> SEQ ID NO 27
<211> LENGTH: 13
<212> TYPE: PRT
<213> ORGANISM: Homo sapiens

<400> SEQUENCE: 27

Glu Asn Ala Lys Ala Lys Thr Asp His Gly Ala Glu Ile
1               5                   10

<210> SEQ ID NO 28
<211> LENGTH: 10
<212> TYPE: PRT
<213> ORGANISM: Rattus norvegicus

<400> SEQUENCE: 28

Gln Glu Gly Asp Met Asp His Gly Leu Lys
1               5                   10

<210> SEQ ID NO 29
<211> LENGTH: 10
<212> TYPE: PRT
<213> ORGANISM: Rattus norvegicus

<400> SEQUENCE: 29

Glu Ser Pro Pro Gln Pro Pro Ala Asp Asp
1               5                   10

<210> SEQ ID NO 30
<211> LENGTH: 10
<212> TYPE: PRT
<213> ORGANISM: Homo sapiens

<400> SEQUENCE: 30

Gln Glu Gly Asp Thr Asp Ala Gly Leu Lys
1               5                   10
```

```
<210> SEQ ID NO 31
<211> LENGTH: 10
<212> TYPE: PRT
<213> ORGANISM: Homo sapiens

<400> SEQUENCE: 31

Glu Ser Pro Leu Gln Thr Pro Thr Glu Asp
1               5                   10

<210> SEQ ID NO 32
<211> LENGTH: 10
<212> TYPE: PRT
<213> ORGANISM: Homo sapiens

<400> SEQUENCE: 32

Gly Thr Tyr Gly Leu Gly Asp Arg Lys Asp
1               5                   10

<210> SEQ ID NO 33
<211> LENGTH: 9
<212> TYPE: PRT
<213> ORGANISM: Homo sapiens

<400> SEQUENCE: 33

Gln Gly Gly Tyr Thr Met His Gln Asp
1               5

<210> SEQ ID NO 34
<211> LENGTH: 10
<212> TYPE: PRT
<213> ORGANISM: Homo sapiens

<400> SEQUENCE: 34

Gly Lys Thr Lys Ile Ala Thr Pro Arg Gly
1               5                   10

<210> SEQ ID NO 35
<211> LENGTH: 10
<212> TYPE: PRT
<213> ORGANISM: Homo sapiens

<400> SEQUENCE: 35

Ala Ala Pro Pro Gly Gln Lys Gly Gln Ala
1               5                   10

<210> SEQ ID NO 36
<211> LENGTH: 11
<212> TYPE: PRT
<213> ORGANISM: Homo sapiens

<400> SEQUENCE: 36

Ala Gly His Val Thr Gln Ala Arg Met Val Ser
1               5                   10

<210> SEQ ID NO 37
<211> LENGTH: 10
<212> TYPE: PRT
<213> ORGANISM: Homo sapiens

<400> SEQUENCE: 37

Lys Ser Lys Asp Gly Thr Gly Ser Asp Asp
1               5                   10
```

```
<210> SEQ ID NO 38
<211> LENGTH: 7
<212> TYPE: PRT
<213> ORGANISM: Homo sapiens

<400> SEQUENCE: 38

Ser His Glu Arg Ala Ile Lys
1               5

<210> SEQ ID NO 39
<211> LENGTH: 7
<212> TYPE: PRT
<213> ORGANISM: Homo sapiens

<400> SEQUENCE: 39

Leu Gly Arg His Glu Asn Ala
1               5

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: eAhx

<400> SEQUENCE: 40

Cys Xaa Ser Ser Thr Gly Ser Ile Asp Met Val Asp
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Thr Arg Glu Pro Lys Lys Val Ala Val Val
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Ser Lys Asp Gly Thr Gly Ser Asp Asp
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Ser Pro Leu Gln Thr Pro Thr Glu Asp
```

```
1               5                   10
```

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

His Val Thr Gln Ala Arg Met Val Ser
1               5

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acatcgagat cgccacctac a                                                   21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtctgcacgg gaatggtgat                                                     20

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
agctgctaga gggcgaggag aaccg                                               25

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
actgggattt gaggatggat cag                                                 23

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

```
gccttcctgt gccacgg                                              17

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
aatgaggcca tacaggcagc ccatg                                     25

<210> SEQ ID NO 51
<211> LENGTH: 22
<212> TYPE: RNA
<213> ORGANISM: Homo sapiens

<400> SEQUENCE: 51
ugcggggcua gggcuaacag ca                                        22

<210> SEQ ID NO 52
<211> LENGTH: 22
<212> TYPE: RNA
<213> ORGANISM: Homo sapiens

<400> SEQUENCE: 52
ggggcugggg ccggggccga gc                                        22

<210> SEQ ID NO 53
<211> LENGTH: 22
<212> TYPE: RNA
<213> ORGANISM: Homo sapiens

<400> SEQUENCE: 53
gggacccagg gagagacgua ag                                        22

<210> SEQ ID NO 54
<211> LENGTH: 22
<212> TYPE: RNA
<213> ORGANISM: Homo sapiens

<400> SEQUENCE: 54
ucaggcucag uccccucccg au                                        22

<210> SEQ ID NO 55
<211> LENGTH: 21
<212> TYPE: RNA
<213> ORGANISM: Homo sapiens

<400> SEQUENCE: 55
uggaggagaa ggaaggugau g                                         21

<210> SEQ ID NO 56
<211> LENGTH: 22
<212> TYPE: RNA
<213> ORGANISM: Homo sapiens

<400> SEQUENCE: 56
ugagguagua gguugugugg uu                                        22

<210> SEQ ID NO 57
<211> LENGTH: 22
<212> TYPE: RNA
```

<213> ORGANISM: Homo sapiens

<400> SEQUENCE: 57
aggcggggcg ccgcgggacc gc             22

<210> SEQ ID NO 58
<211> LENGTH: 22
<212> TYPE: RNA
<213> ORGANISM: Homo sapiens

<400> SEQUENCE: 58
cugggagagg guuguuuacu cc             22

<210> SEQ ID NO 59
<211> LENGTH: 22
<212> TYPE: RNA
<213> ORGANISM: Homo sapiens

<400> SEQUENCE: 59
ugagguagua guuugugcug uu             22

<210> SEQ ID NO 60
<211> LENGTH: 19
<212> TYPE: RNA
<213> ORGANISM: Homo sapiens

<400> SEQUENCE: 60
aauggauuuu uggagcagg                 19

<210> SEQ ID NO 61
<211> LENGTH: 17
<212> TYPE: RNA
<213> ORGANISM: Homo sapiens

<400> SEQUENCE: 61 guggggaga ggcuguc                    17

<210> SEQ ID NO 62
<211> LENGTH: 19
<212> TYPE: RNA
<213> ORGANISM: Homo sapiens

<400> SEQUENCE: 62
uggauuuuug gaucaggga                 19

<210> SEQ ID NO 63
<211> LENGTH: 23
<212> TYPE: RNA
<213> ORGANISM: Homo sapiens

<400> SEQUENCE: 63 caaagucug uucgugcagg uag             23

<210> SEQ ID NO 64
<211> LENGTH: 23
<212> TYPE: RNA
<213> ORGANISM: Homo sapiens

<400> SEQUENCE: 64
ugaggggcag agagcgagac uuu            23

<210> SEQ ID NO 65
<211> LENGTH: 21

```
<212> TYPE: RNA
<213> ORGANISM: Homo sapiens

<400> SEQUENCE: 65
gugccagcug cagugggga g                                              21

<210> SEQ ID NO 66
<211> LENGTH: 22
<212> TYPE: RNA
<213> ORGANISM: Homo sapiens

<400> SEQUENCE: 66
gguccagagg ggagauaggu uc                                            22

<210> SEQ ID NO 67
<211> LENGTH: 20
<212> TYPE: RNA
<213> ORGANISM: Homo sapiens

<400> SEQUENCE: 67
aaaagcuggg uugagagggu                                               20

<210> SEQ ID NO 68
<211> LENGTH: 22
<212> TYPE: RNA
<213> ORGANISM: Homo sapiens

<400> SEQUENCE: 68
aaaagcuggg uugagagggc ga                                            22

<210> SEQ ID NO 69
<211> LENGTH: 22
<212> TYPE: RNA
<213> ORGANISM: Homo sapiens

<400> SEQUENCE: 69
aaaagcuggg uugagagggc aa                                            22

<210> SEQ ID NO 70
<211> LENGTH: 22
<212> TYPE: RNA
<213> ORGANISM: Homo sapiens

<400> SEQUENCE: 70
ugagguagua gguuguaugg uu                                            22

<210> SEQ ID NO 71
<211> LENGTH: 22
<212> TYPE: RNA
<213> ORGANISM: Homo sapiens

<400> SEQUENCE: 71
uggcucaguu cagcaggaac ag                                            22

<210> SEQ ID NO 72
<211> LENGTH: 19
<212> TYPE: RNA
<213> ORGANISM: Homo sapiens

<400> SEQUENCE: 72
aaaagcuggg uugagagga                                                19

<210> SEQ ID NO 73
```

```
<211> LENGTH: 22
<212> TYPE: RNA
<213> ORGANISM: Homo sapiens

<400> SEQUENCE: 73
uccuguacug agcugccccg ag                                              22

<210> SEQ ID NO 74
<211> LENGTH: 23
<212> TYPE: RNA
<213> ORGANISM: Homo sapiens

<400> SEQUENCE: 74
aaugacacga ucacucccgu uga                                             23

<210> SEQ ID NO 75
<211> LENGTH: 22
<212> TYPE: RNA
<213> ORGANISM: Homo sapiens

<400> SEQUENCE: 75
uauugcacuu gucccggccu gu                                              22

<210> SEQ ID NO 76
<211> LENGTH: 22
<212> TYPE: RNA
<213> ORGANISM: Homo sapiens

<400> SEQUENCE: 76
ugagguagua gguuguauag uu                                              22

<210> SEQ ID NO 77
<211> LENGTH: 22
<212> TYPE: RNA
<213> ORGANISM: Homo sapiens

<400> SEQUENCE: 77
cauugcacuu gucucggucu ga                                              22

<210> SEQ ID NO 78
<211> LENGTH: 22
<212> TYPE: RNA
<213> ORGANISM: Homo sapiens

<400> SEQUENCE: 78
aagacgggag gaaagaaggg ag                                              22

<210> SEQ ID NO 79
<211> LENGTH: 22
<212> TYPE: RNA
<213> ORGANISM: Homo sapiens

<400> SEQUENCE: 79
uguaaacauc cccgacugga ag                                              22

<210> SEQ ID NO 80
<211> LENGTH: 22
<212> TYPE: RNA
<213> ORGANISM: Homo sapiens

<400> SEQUENCE: 80
uggagagaaa ggcaguuccu ga                                              22
```

```
<210> SEQ ID NO 81
<211> LENGTH: 22
<212> TYPE: RNA
<213> ORGANISM: Homo sapiens

<400> SEQUENCE: 81
ugucaguuug ucaaauaccc ca                                              22

<210> SEQ ID NO 82
<211> LENGTH: 22
<212> TYPE: RNA
<213> ORGANISM: Homo sapiens

<400> SEQUENCE: 82
aaaccguuac cauuacugag uu                                              22

<210> SEQ ID NO 83
<211> LENGTH: 22
<212> TYPE: RNA
<213> ORGANISM: Homo sapiens

<400> SEQUENCE: 83
uagcagcacg uaaauauugg cg                                              22

<210> SEQ ID NO 84
<211> LENGTH: 20
<212> TYPE: RNA
<213> ORGANISM: Homo sapiens

<400> SEQUENCE: 84
cuguaugccc ucaccgcuca                                                 20

<210> SEQ ID NO 85
<211> LENGTH: 21
<212> TYPE: RNA
<213> ORGANISM: Homo sapiens

<400> SEQUENCE: 85
ccaguccugu gccugccgcc u                                               21

<210> SEQ ID NO 86
<211> LENGTH: 21
<212> TYPE: RNA
<213> ORGANISM: Homo sapiens

<400> SEQUENCE: 86
ccgucgccgc cacccgagcc g                                               21

<210> SEQ ID NO 87
<211> LENGTH: 22
<212> TYPE: RNA
<213> ORGANISM: Homo sapiens

<400> SEQUENCE: 87
ucaggccagg cacaguggcu ca                                              22

<210> SEQ ID NO 88
<211> LENGTH: 23
<212> TYPE: RNA
<213> ORGANISM: Homo sapiens

<400> SEQUENCE: 88
cucucaccac ugcccuccca cag                                             23
```

-continued

```
<210> SEQ ID NO 89
<211> LENGTH: 22
<212> TYPE: RNA
<213> ORGANISM: Homo sapiens

<400> SEQUENCE: 89
aaccagcacc ccaacuuugg ac                                              22

<210> SEQ ID NO 90
<211> LENGTH: 22
<212> TYPE: RNA
<213> ORGANISM: Homo sapiens

<400> SEQUENCE: 90
cagccacaac uacccugcca cu                                              22

<210> SEQ ID NO 91
<211> LENGTH: 22
<212> TYPE: RNA
<213> ORGANISM: Homo sapiens

<400> SEQUENCE: 91
uccauuacac uacccugccu cu                                              22

<210> SEQ ID NO 92
<211> LENGTH: 18
<212> TYPE: RNA
<213> ORGANISM: Homo sapiens

<400> SEQUENCE: 92
uccagugccc uccucucc                                                   18

<210> SEQ ID NO 93
<211> LENGTH: 22
<212> TYPE: RNA
<213> ORGANISM: Homo sapiens

<400> SEQUENCE: 93
ccucccacac ccaaggcuug ca                                              22

<210> SEQ ID NO 94
<211> LENGTH: 21
<212> TYPE: RNA
<213> ORGANISM: Homo sapiens

<400> SEQUENCE: 94
ccccaccucc ucucuccuca g                                               21

<210> SEQ ID NO 95
<211> LENGTH: 18
<212> TYPE: RNA
<213> ORGANISM: Homo sapiens

<400> SEQUENCE: 95
aucccaccuc ugccacca                                                   18

<210> SEQ ID NO 96
<211> LENGTH: 22
<212> TYPE: RNA
<213> ORGANISM: Homo sapiens

<400> SEQUENCE: 96
ucggauccgu cugagcuugg cu                                              22
```

```
<210> SEQ ID NO 97
<211> LENGTH: 20
<212> TYPE: RNA
<213> ORGANISM: Homo sapiens

<400> SEQUENCE: 97
ugagcccugu cucccgcag                                                    20

<210> SEQ ID NO 98
<211> LENGTH: 23
<212> TYPE: RNA
<213> ORGANISM: Homo sapiens

<400> SEQUENCE: 98
ugugcuugcu cgucccgccc gca                                               23

<210> SEQ ID NO 99
<211> LENGTH: 20
<212> TYPE: RNA
<213> ORGANISM: Homo sapiens

<400> SEQUENCE: 99
ucacaccugc cucgccccc                                                    20

<210> SEQ ID NO 100
<211> LENGTH: 22
<212> TYPE: RNA
<213> ORGANISM: Homo sapiens

<400> SEQUENCE: 100
uucaccaccu ucuccaccca gc                                                22

<210> SEQ ID NO 101
<211> LENGTH: 22
<212> TYPE: RNA
<213> ORGANISM: Homo sapiens

<400> SEQUENCE: 101
ucaccagccc uguguucccu ag                                                22

<210> SEQ ID NO 102
<211> LENGTH: 22
<212> TYPE: RNA
<213> ORGANISM: Homo sapiens

<400> SEQUENCE: 102
uuagggcccu ggcuccaucu cc                                                22

<210> SEQ ID NO 103
<211> LENGTH: 22
<212> TYPE: RNA
<213> ORGANISM: Homo sapiens

<400> SEQUENCE: 103
cuggcccucu cugcccuucc gu                                                22

<210> SEQ ID NO 104
<211> LENGTH: 20
<212> TYPE: RNA
<213> ORGANISM: Homo sapiens

<400> SEQUENCE: 104
```
ccuccugccc uccuugcugu                                          20

<210> SEQ ID NO 105
<211> LENGTH: 22
<212> TYPE: RNA
<213> ORGANISM: Homo sapiens

<400> SEQUENCE: 105
cacgcucaug cacacaccca ca                                       22

<210> SEQ ID NO 106
<211> LENGTH: 22
<212> TYPE: RNA
<213> ORGANISM: Homo sapiens

<400> SEQUENCE: 106
acuccagccc cacagccuca gc                                       22

<210> SEQ ID NO 107
<211> LENGTH: 17
<212> TYPE: RNA
<213> ORGANISM: Homo sapiens

<400> SEQUENCE: 107
ucccaccgcu gccaccc                                             17

<210> SEQ ID NO 108
<211> LENGTH: 21
<212> TYPE: RNA
<213> ORGANISM: Homo sapiens

<400> SEQUENCE: 108
gcccuccgcc cgugcacccc g                                        21

<210> SEQ ID NO 109
<211> LENGTH: 22
<212> TYPE: RNA
<213> ORGANISM: Homo sapiens

<400> SEQUENCE: 109
acggguuagg cucuugggag cu                                       22

<210> SEQ ID NO 110
<211> LENGTH: 20
<212> TYPE: RNA
<213> ORGANISM: Homo sapiens

<400> SEQUENCE: 110
cgugccaccc uuuucccag                                           20

<210> SEQ ID NO 111
<211> LENGTH: 22
<212> TYPE: RNA
<213> ORGANISM: Homo sapiens

<400> SEQUENCE: 111
uccgagccug ggucucccuc uu                                       22

<210> SEQ ID NO 112
<211> LENGTH: 22
<212> TYPE: RNA
<213> ORGANISM: Homo sapiens

<400> SEQUENCE: 112
ugagccccug ugccgcccc ag                                                     22

<210> SEQ ID NO 113
<211> LENGTH: 22
<212> TYPE: RNA
<213> ORGANISM: Homo sapiens

<400> SEQUENCE: 113
ucugggcaac aaagugagac cu                                                    22

<210> SEQ ID NO 114
<211> LENGTH: 432
<212> TYPE: PRT
<213> ORGANISM: Homo sapiens

<400> SEQUENCE: 114

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
            20                  25                  30

Pro Gly Thr Arg Leu Ser Leu Ala Arg Met Pro Pro Pro Leu Pro Thr
        35                  40                  45

Arg Val Asp Phe Ser Leu Ala Gly Ala Leu Asn Ala Gly Phe Lys Glu
    50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
        115                 120                 125

Gln Leu Thr Ala Asn Ser Ala Arg Leu Glu Val Glu Arg Asp Asn Leu
    130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
        195                 200                 205

Arg Glu Leu Gln Glu Gln Leu Ala Arg Gln Gln Val His Val Glu Leu
    210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
        275                 280                 285

Leu Gln Ser Leu Thr Cys Asp Leu Glu Ser Leu Arg Gly Thr Asn Glu
    290                 295                 300

Ser Leu Glu Arg Gln Met Arg Glu Gln Glu Glu Arg His Val Arg Glu

```
            305                 310                 315                 320
Ala Ala Ser Tyr Gln Glu Ala Leu Ala Arg Leu Glu Glu Gly Gln
                325                 330                 335

Ser Leu Lys Asp Glu Met Ala Arg His Leu Gln Glu Tyr Gln Asp Leu
                340                 345                 350

Leu Asn Val Lys Leu Ala Leu Asp Ile Glu Ile Ala Thr Tyr Arg Lys
                355                 360                 365

Leu Leu Glu Gly Glu Glu Asn Arg Ile Thr Ile Pro Val Gln Thr Phe
            370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
                405                 410                 415

Asp Gly Glu Val Ile Lys Glu Ser Lys Gln Glu His Lys Asp Val Met
                420                 425                 430

<210> SEQ ID NO 115
<211> LENGTH: 10
<212> TYPE: PRT
<213> ORGANISM: Rattus norvegicus

<400> SEQUENCE: 115

Gln Glu Gly Asp Met Asp His Gly Leu Lys
1               5                   10

<210> SEQ ID NO 116
<211> LENGTH: 10
<212> TYPE: PRT
<213> ORGANISM: Rattus norvegicus

<400> SEQUENCE: 116

Gln Glu Gly Asp Met Asp His Gly Leu Lys
1               5                   10

<210> SEQ ID NO 117
<211> LENGTH: 10
<212> TYPE: PRT
<213> ORGANISM: Rattus norvegicus

<400> SEQUENCE: 117

Val Thr Gln Ala Arg Val Ala Gly Val Ser
1               5                   10

<210> SEQ ID NO 118
<211> LENGTH: 10
<212> TYPE: PRT
<213> ORGANISM: Rattus norvegicus

<400> SEQUENCE: 118

Lys Asp Arg Thr Gly Asn Asp Glu Lys Lys
1               5                   10

<210> SEQ ID NO 119
<211> LENGTH: 10
<212> TYPE: PRT
<213> ORGANISM: Rattus norvegicus

<400> SEQUENCE: 119

Thr Arg Glu Pro Lys Lys Val Ala Val Val
1               5                   10
```

```
<210> SEQ ID NO 120
<211> LENGTH: 10
<212> TYPE: PRT
<213> ORGANISM: Rattus norvegicus

<400> SEQUENCE: 120

Arg Thr Pro Pro Lys Ser Pro Ser Ala Ser
1               5                   10

<210> SEQ ID NO 121
<211> LENGTH: 10
<212> TYPE: PRT
<213> ORGANISM: Rattus norvegicus

<400> SEQUENCE: 121

Lys Ile Glu Thr His Lys Leu Thr Phe Arg
1               5                   10

<210> SEQ ID NO 122
<211> LENGTH: 10
<212> TYPE: PRT
<213> ORGANISM: Rattus norvegicus

<400> SEQUENCE: 122

Glu Asn Ala Lys Ala Lys Thr Asp His Gly
1               5                   10

<210> SEQ ID NO 123
<211> LENGTH: 10
<212> TYPE: PRT
<213> ORGANISM: Rattus norvegicus

<400> SEQUENCE: 123

Ser Ser Thr Gly Ser Ile Asp Met Val Asp
1               5                   10

<210> SEQ ID NO 124
<211> LENGTH: 10
<212> TYPE: PRT
<213> ORGANISM: Rattus norvegicus

<400> SEQUENCE: 124

Ser Pro Gln Leu Ala Thr Leu Ala Asp Glu
1               5                   10

<210> SEQ ID NO 125
<211> LENGTH: 10
<212> TYPE: PRT
<213> ORGANISM: Homo sapiens

<400> SEQUENCE: 125

Gly His Val Thr Gln Ala Arg Met Val Ser
1               5                   10

<210> SEQ ID NO 126
<211> LENGTH: 10
<212> TYPE: PRT
<213> ORGANISM: Homo sapiens

<400> SEQUENCE: 126

Lys Ser Lys Asp Gly Thr Gly Ser Asp Asp
1               5                   10

<210> SEQ ID NO 127
<211> LENGTH: 10
```

<212> TYPE: PRT
<213> ORGANISM: Homo sapiens

<400> SEQUENCE: 127

Thr Arg Glu Pro Lys Lys Val Ala Val Val
1               5                   10

<210> SEQ ID NO 128
<211> LENGTH: 10
<212> TYPE: PRT
<213> ORGANISM: Homo sapiens

<400> SEQUENCE: 128

Arg Thr Pro Pro Lys Ser Pro Ser Ser Ala
1               5                   10

<210> SEQ ID NO 129
<211> LENGTH: 10
<212> TYPE: PRT
<213> ORGANISM: Homo sapiens

<400> SEQUENCE: 129

Gly Lys Thr Lys Ile Ala Thr Pro Arg Gly
1               5                   10

<210> SEQ ID NO 130
<211> LENGTH: 10
<212> TYPE: PRT
<213> ORGANISM: Homo sapiens

<400> SEQUENCE: 130

Ala Ala Pro Pro Gly Gln Lys Gly Gln Ala
1               5                   10

<210> SEQ ID NO 131
<211> LENGTH: 10
<212> TYPE: PRT
<213> ORGANISM: Homo sapiens

<400> SEQUENCE: 131

Gln Glu Gly Asp Thr Asp Ala Gly Leu Lys
1               5                   10

<210> SEQ ID NO 132
<211> LENGTH: 10
<212> TYPE: PRT
<213> ORGANISM: Homo sapiens

<400> SEQUENCE: 132

Glu Ser Pro Leu Gln Thr Pro Thr Glu Asp
1               5                   10

<210> SEQ ID NO 133
<211> LENGTH: 10
<212> TYPE: PRT
<213> ORGANISM: Homo sapiens

<400> SEQUENCE: 133

Lys Ile Glu Thr His Lys Leu Thr Phe Arg
1               5                   10

<210> SEQ ID NO 134
<211> LENGTH: 10
<212> TYPE: PRT
<213> ORGANISM: Homo sapiens

<400> SEQUENCE: 134

Glu Asn Ala Lys Ala Lys Thr Asp His Gly
1               5                   10

<210> SEQ ID NO 135
<211> LENGTH: 10
<212> TYPE: PRT
<213> ORGANISM: Homo sapiens

<400> SEQUENCE: 135

Gly Thr Tyr Gly Leu Gly Asp Arg Lys Asp
1               5                   10

<210> SEQ ID NO 136
<211> LENGTH: 10
<212> TYPE: PRT
<213> ORGANISM: Homo sapiens

<400> SEQUENCE: 136

Gln Gly Gly Tyr Thr Met His Gln Asp Gln
1               5                   10

<210> SEQ ID NO 137
<211> LENGTH: 10
<212> TYPE: PRT
<213> ORGANISM: Homo sapiens

<400> SEQUENCE: 137

Ser Ser Thr Gly Ser Ile Asp Met Val Asp
1               5                   10

<210> SEQ ID NO 138
<211> LENGTH: 10
<212> TYPE: PRT
<213> ORGANISM: Homo sapiens

<400> SEQUENCE: 138

Ser Pro Gln Leu Ala Thr Leu Ala Asp Glu
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Val Asp Phe Ser Leu Ala Gly Ala Leu Asn
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Gly Phe Lys Glu Thr Arg Ala Ser Glu
1               5                   10

```
<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Glu Asn Arg Ile Thr Ile Pro Val Gln Thr
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Phe Ser Asn Leu Gln Ile Arg Glu Thr Ser
1               5                   10

<210> SEQ ID NO 143
<211> LENGTH: 8
<212> TYPE: PRT
<213> ORGANISM: Rattus norvegicus

<400> SEQUENCE: 143

Ser Pro Gln Leu Ala Thr Leu Ala
1               5

<210> SEQ ID NO 144
<211> LENGTH: 11
<212> TYPE: PRT
<213> ORGANISM: Rattus norvegicus

<400> SEQUENCE: 144

Pro Thr Arg Glu Pro Lys Lys Val Ala Val Val
1               5                   10

<210> SEQ ID NO 145
<211> LENGTH: 10
<212> TYPE: PRT
<213> ORGANISM: Mus sp.

<400> SEQUENCE: 145

Lys Ile Glu Thr His Lys Leu Thr Phe Arg
1               5                   10

<210> SEQ ID NO 146
<211> LENGTH: 13
<212> TYPE: PRT
<213> ORGANISM: Rattus norvegicus

<400> SEQUENCE: 146

Glu Asn Ala Lys Ala Lys Thr Asp His Gly Ala Glu Ile
1               5                   10

<210> SEQ ID NO 147
<211> LENGTH: 13
<212> TYPE: PRT
<213> ORGANISM: Mus sp.

<400> SEQUENCE: 147
```

```
Glu Asn Ala Lys Ala Lys Thr Asp His Gly Ala Glu Ile
1               5                   10
```

<210> SEQ ID NO 148
<211> LENGTH: 7
<212> TYPE: PRT
<213> ORGANISM: Rattus norvegicus

<400> SEQUENCE: 148

```
Ser His Glu Arg Ala Ile Lys
1               5
```

<210> SEQ ID NO 149
<211> LENGTH: 7
<212> TYPE: PRT
<213> ORGANISM: Rattus norvegicus

<400> SEQUENCE: 149

```
Leu Gly Arg His Glu Asn Ala
1               5
```

<210> SEQ ID NO 150
<211> LENGTH: 8
<212> TYPE: PRT
<213> ORGANISM: Homo sapiens

<400> SEQUENCE: 150

```
Gln Gly Gly Tyr Thr Met His Gln
1               5
```

<210> SEQ ID NO 151
<211> LENGTH: 11
<212> TYPE: PRT
<213> ORGANISM: Homo sapiens

<400> SEQUENCE: 151

```
Lys Ser Lys Asp Gly Thr Gly Ser Asp Asp Lys
1               5                   10
```

<210> SEQ ID NO 152
<211> LENGTH: 7
<212> TYPE: PRT
<213> ORGANISM: Homo sapiens

<400> SEQUENCE: 152

```
Thr His Lys Leu Thr Phe Arg
1               5
```

<210> SEQ ID NO 153
<211> LENGTH: 8
<212> TYPE: PRT
<213> ORGANISM: Homo sapiens

<400> SEQUENCE: 153

```
Glu Asn Ala Lys Ala Lys Thr Asp
1               5
```

MICRO-RNA, AUTOANTIBODY AND PROTEIN MARKERS FOR DIAGNOSIS OF NEURONAL INJURY

CROSS REFERENCE TO RELATED APPLICATIONS

This application is a continuation of U.S. patent application Ser. No. 13/395,931, filed Jul. 12, 2012, which in turn is a national stage entry of Patent Cooperation Treaty Application Serial No. PCT/US2010/048789, filed Sep. 14, 2010, which claims priority to U.S. Provisional Application Nos. 61/242,123 filed Sep. 14, 2009, 61/354,504 filed Jun. 14, 2010, 61/355,779 filed Jun. 17, 2010, and 61/380,158 filed Sep. 3, 2010, the contents of each of which are incorporated herein in their entirety.

INCORPORATION BY REFERENCE OF SEQUENCE LISTING

The present application is being filed along with a Sequence Listing in electronic format. The Sequence Listing is provided as a file entitled 750582001101SeqList.TXT, created Dec. 27, 2016, which is 36,869 bytes in size. The information in the electronic format of the Sequence Listing is incorporated by reference in its entirety.

FIELD OF THE INVENTION

The present invention relates to the identification of markers of traumatic brain injury (TBI) or other neurological conditions including stroke, Alzeimer's disease, Parkinson disease and Chronic Traumatic Encephalopathy (CTE). Inventive markers include auto-antibodies, DNA, RNA, or miRNA that may play a role in central nervous system function and therapy. The invention also relates to diagnostic and therapeutic materials and methods, including methods for detecting biomarkers in brain injury, and the diagnostic method for aiding and monitoring the propensity or progression of brain injury.

BACKGROUND OF THE INVENTION

The field of clinical neurology remains frustrated by the recognition that secondary injury to a central nervous system tissue associated with physiologic response to the initial insult could be lessened if only the initial insult could be rapidly diagnosed or in the case of a progressive disorder before stress on central nervous system tissues reached a preselected threshold. Traumatic, ischemic, and neurotoxic chemical insult, along with generic disorders, all present the prospect of brain damage. While the diagnosis of severe forms of each of these causes of brain damage is straightforward through clinical response testing, computed tomography (CT), and magnetic resonance imaging (MRI), the imaging diagnostics are limited by both the high cost of spectroscopic imaging and long diagnostic time. The clinical response testing of incapacitated individuals is of limited value and often precludes a nuanced diagnosis. Additionally, owing to the limitations of existing diagnostics, situations arise wherein a subject experiences a stress to their neurological condition but are often unaware that damage has occurred or fail seek treatment as the subtle symptoms often quickly resolve. The lack of treatment of these mild to moderate challenges to neurologic condition of a subject can have a cumulative effect or otherwise result in a severe brain damage event, either of which have a poor clinical prognosis.

In order to overcome the limitations associated with spectroscopic and clinical response diagnosis of neurological condition, there is increasing attention on the use of biomarkers as internal indicators of change to molecular or cellular level health condition of a subject. As biomarker detection uses a sample obtained from a subject, typically cerebrospinal fluid, blood, or plasma, and detects the biomarkers in that sample, biomarker detection holds the prospect of inexpensive, rapid, and objective measurement of neurological condition. The attainment of rapid and objective indicators of neurological condition allows one to determine severity of a non-normal brain condition with a previously unrealized degree of objectivity, predict outcome, guide therapy of the condition, as well as monitor subject responsiveness and recovery. Additionally, such information as obtained from numerous subjects allows one to gain a degree of insight into the mechanism of brain injury.

Biomarkers of central nervous system (CNS) injury could provide physicians and laboratory studies with quantifiable neurochemical markers to help determine not only the severity and cellular pathology of injury, but also provide a surrogate marker of therapeutic interventions. While a number of potential biochemical markers for TBI have been proposed, no definitive marker or process has been shown capable of diagnosing TBI, distinguishing between MTBI and TBI, or of demonstrating successful or therapeutic advantage of therapeutic administration. This shortcoming is further apparent should an individual also suffer from multiple organ injury. Brain injuries are commonly difficult to treat effectively, and successful outcome commonly depends on how rapidly an individual is diagnosed with a particular injury subtype. Thus, a need exists for a sensitive and specific biochemical marker(s) of TBI with the diagnostic ability to evaluate post-concussion intracranial pathology to improve patient management and facilitate therapeutic evaluation.

SUMMARY OF THE INVENTION

Materials and processes for detecting a neurological condition in a subject are provided that include measuring a quantity of one or more neuron specific biomarkers in a biological sample, wherein the synthesis or production of the biomarker is altered following an injury and detecting a neurological condition based on a ratio of the quantity one or more of the biomarkers in said biological sample. A neuron specific biomarker is optionally a protein, a protein breakdown product, nucleic acid molecule (e.g. oligonucleotide such as DNA, RNA, or miRNA), or an autoantibody to any thereof. Optionally combinations of multiple biomarkers are measured in one or more biological samples. Illustrative examples of biomarkers include an autoantibody directed toward a protein, wherein said protein is: GFAP; Tau; S100β; βIII-tubulin; Neurofilament light, medium or heavy polypeptide (NF-L, -M and -H); V-type proton ATPase; Gamma-enolase (NSE); vimentin; endophilin-A1; Microtubule-associated protein 2 (MAP-2); alpha-internexin; neuroserpin; neuromodulin; synaptotagmin-1; Voltage-gated potassium channel; collapsin response mediator proteins (CRMP-1 to 5); αII-spectrin; neurofascin; MBP; ubiquitin carboxyl-terminal esterase; Poly (ADP-ribose) polymerase (PARP); breakdown products thereof; derivatives thereof; or combinations thereof. In some embodiments a biomarker is a nucleic acid encoding at least a portion of a protein such as a DNA or RNA oligonucleotide, wherein the protein is GFAP; αII-spectrin; an αII-spectrin breakdown product; neurofascin; MBP; MAP2; ubiquitin carboxyl-terminal esterase; a ubiquitin carboxyl-terminal hydrolase; a neuronally-localized intracellular protein; MAP-tau; C-tau; Poly (ADP-ribose) polymerase (PARP); a collapsin response mediator protein; breakdown products thereof, derivatives thereof, or combinations thereof. A biomarker is optionally a miRNA. A miRNA is optionally brain enriched or brain specific. A miRNA optionally is a at least a portion of a miRNA that regulates the expression of a protein, wherein the protein is GFAP; αII-spectrin; an αII-spectrin breakdown product; neurofascin; MBP; MAP2; ubiquitin carboxyl-terminal esterase; a ubiquitin carboxyl-terminal hydrolase; a neuronally-localized intracellular protein; MAP-tau; p53; SYTL1; calpastatin; Poly (ADP-ribose) polymerase (PARP); CAPN1, 2, or 6; IRS-1; SMAD5; a collapsin response mediator protein; synaptotagmin-1 or -9; Rho kinase; synapsin 1; syntaphilin; ATXN1; derivatives thereof; or combinations thereof. A miRNA optionally is one of SEQ ID NOs: 51-113, optionally one of SEQ ID NOs: 51-60 or 84-93, or optionally miR-9, miR-34, miR-92b, miR-124a, miR-124b, miR-135, miR-153, miR-183, miR-219, miR-222, miR-125a, miR-125b, miR-128, miR-132, miR-135, miR-137, miR-139, miR-218a, or combinations thereof.

In some embodiments, a biomarker is a breakdown product of a neuronally localized or protein. Optionally a breakdown product is a breakdown product of GFAP such as GBDPs or a breakdown product of Tau such as TBDPs. A GFAP breakdown product is optionally produced by cleavage at Asn59, Thr383, or both, in SEQ ID NO: 114. A TBDP is optionally produced by cleavage C-terminal to amino acid 25, 44, 129, 157, 229, 421, or combinations thereof, each in SEQ ID NO: 11. Alternatively, or additionally, a TBDP is a breakdown product of rat Tau (SEQ ID NO: 5) from cleavage C-terminal to amino acid 43, 120, 220, 370, 412, or combinations thereof.

The measured concentration of one or more biomarkers is optionally compared to the level of the biomarker in a similar biological sample from one or more control subjects to provide a ratio of concentrations. The ratio is optionally positive where the level of biomarker in a biological sample from a subject is higher than that of a control subject, or negative where the level of biomarker in a biological sample from a subject is lower than that of a control subject.

It is appreciated that any suitable biological sample is operable. Illustrative examples include blood, plasma, serum, CSF, urine, saliva, or tissue. A biological sample is optionally cell free plasma or cell free serum.

An injury is optionally induced by a compound. Illustratively, a compound is administered to a subject as a therapeutic, or as a candidate therapeutic such as in drug discovery or development.

The materials and processes detect, diagnose, or measure the level of one or more conditions such as brain injury (e.g. traumatic brain injury), multiple-organ injury, stroke, neurodegenerative disease, or combinations thereof.

Also provided is a detection agent for detecting and optionally quantifying a biomarker in a biological sample. A detection agent optionally binds to a portion of GFAP within 10 amino acids of the cleavage site at amino acid position 59 or 383 in SEQ ID NO: 114 or variants thereof. A detection agent optionally binds human Tau (SEQ ID NO: 11) amino sequence within ten amino acids of the cleavage site at amino acid position 25, 44, 129, 157, 229, or 421. Optionally, a detection agent binds an amino acid sequence SEQ ID NO: 11 or variants thereof within 10 amino acids C-terminal to Ser129, within 10 amino acids N-terminal to Val229, within 10 amino acids N-terminal to Asp421, within 10 amino acids C-terminal to Lys44, within 10 amino acids N-terminal to Ser129. It is appreciated that a detection agent optionally binds an amino acid sequence that is at least a portion of SEQ ID NOs: 20, 21, 24, 25, 26, 27, 30, 31, 32, 33, 34, 35, 36, 37, 38, 39, 40, 41, 42, 43, or 44.'

In some embodiments, a detection agent binds an amino acid sequence that is SEQ ID NO: 5 or a variant thereof within: ten amino acids of the cleavage site at amino acid position 43, 121, 229, 38, or 412; optionally within 10 amino acids N-terminal to Asp421, within 10 amino acids N-terminal to Val220, within 10 amino acids C-terminal to Ser120, within 10 amino acids C-terminal to Lys43, or within 10 amino acids C-terminal to Arg370. A detection agent optionally binds at least a portion of SEQ ID NOs: 20, 21, 22, 23, 24, 25, 26, 27, 28, 29, 38, 39, 40, or 41.

DETAILED DESCRIPTION OF THE DRAWINGS

FIG. 7A illustrates TBDP specific antibodies by western blot using anti-total Tau, FIG. 7B illustrates TBDP specific antibodies by western blot using anti-TauBDP-45K, and FIG. 7C illustrates TBDP specific antibodies by western blot using anti-TauBDP-35K;

Figure 11A:
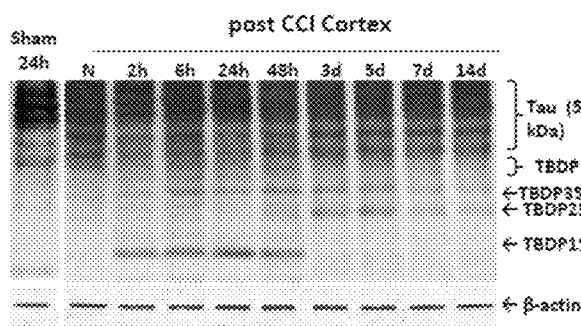
Figure 11B:
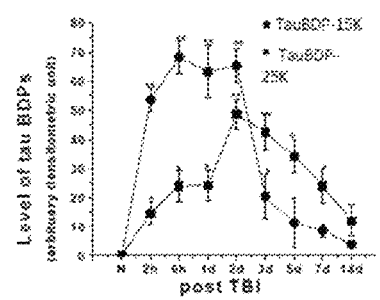
Figure 11C:
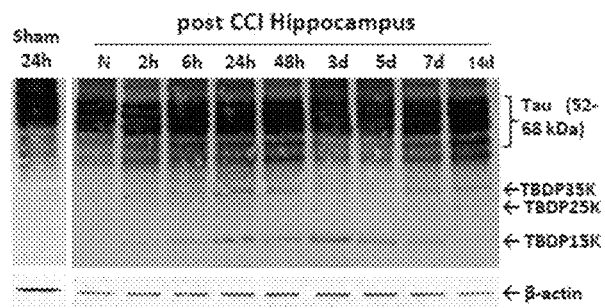
Figure 11D:
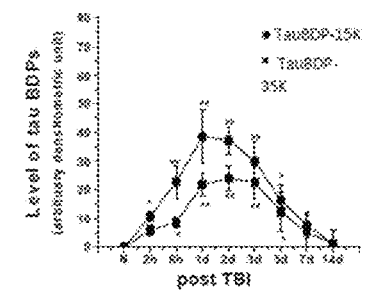
Figure 12A:
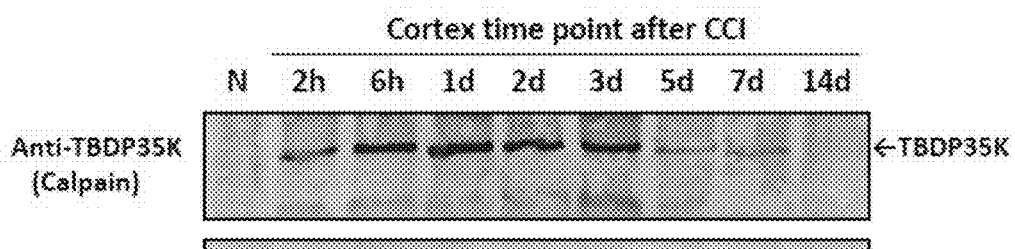
Figure 12B:
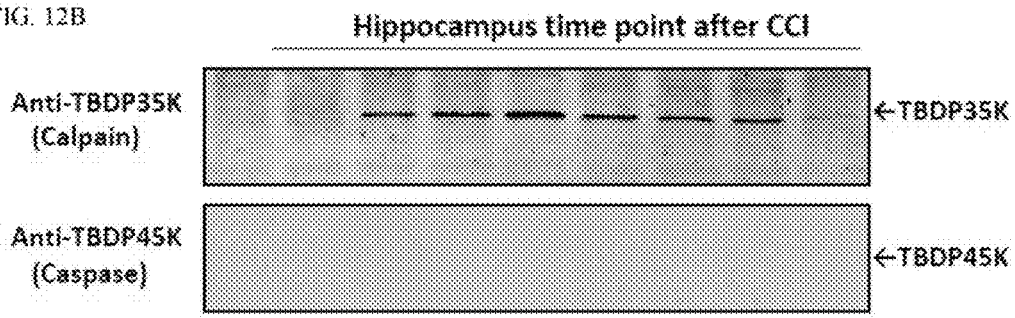
Figure 13A:
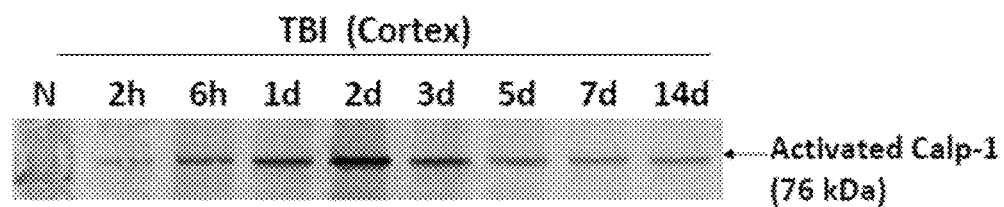
Figure 13B:
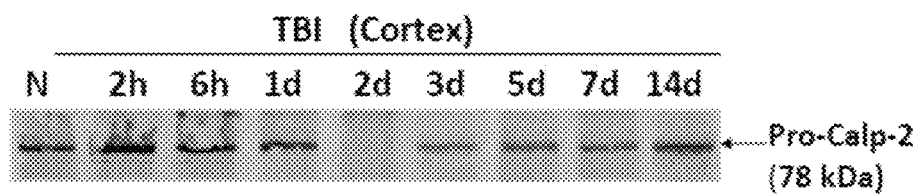
Figure 14A:
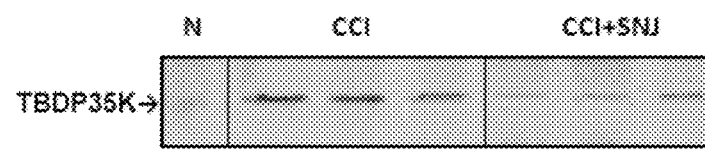
Figure 14B:
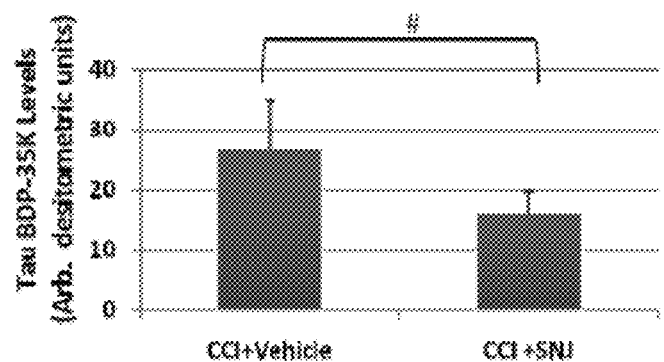
Figure 15A:
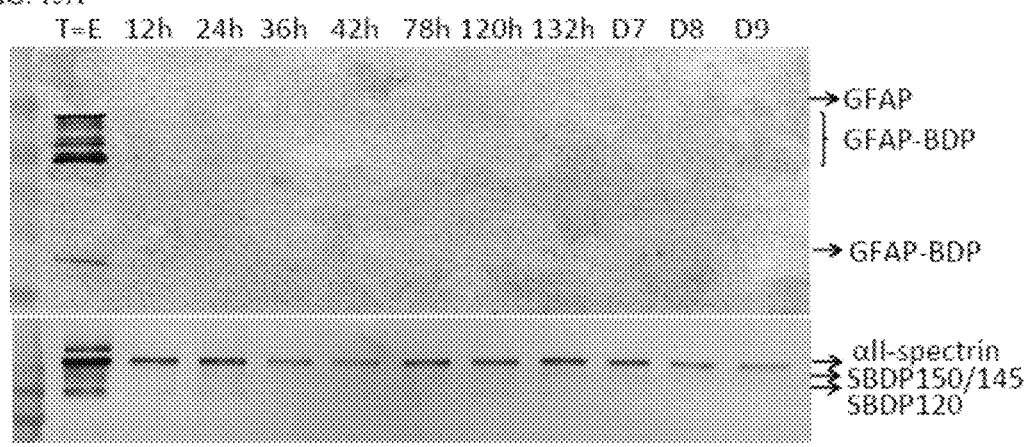
Figure 15B:
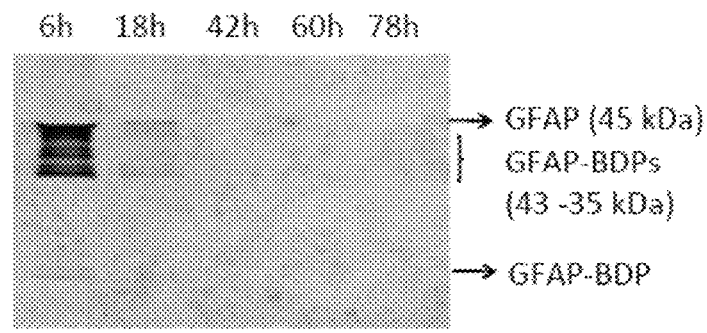
Figure 17:
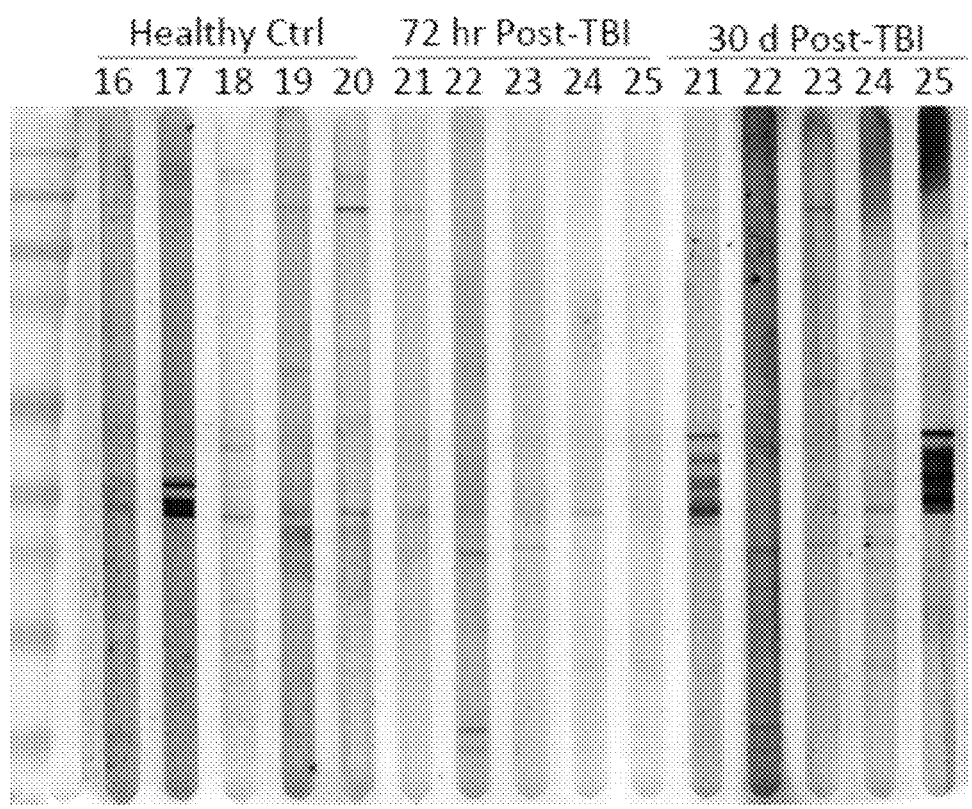
Figure 18A:
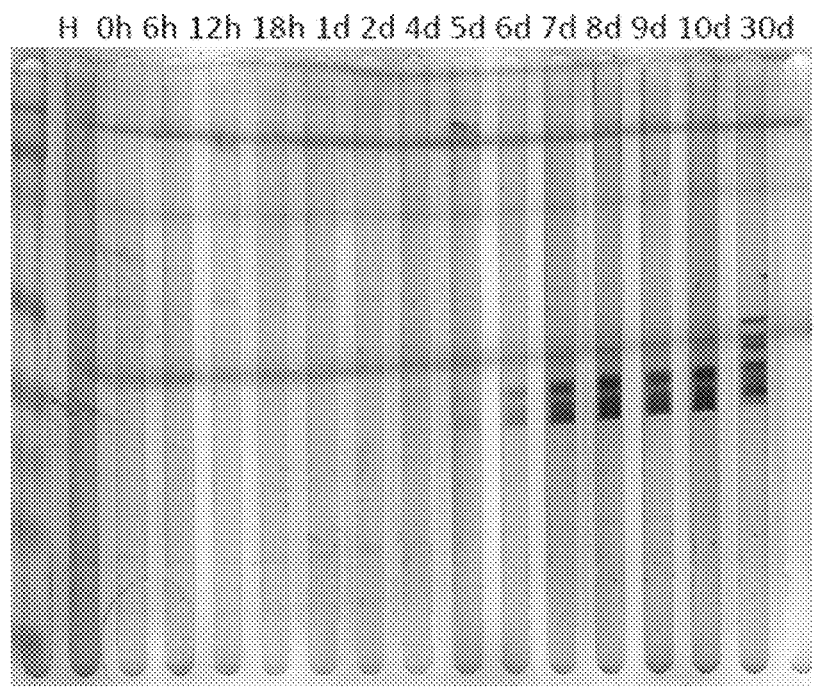
Figure 18B:
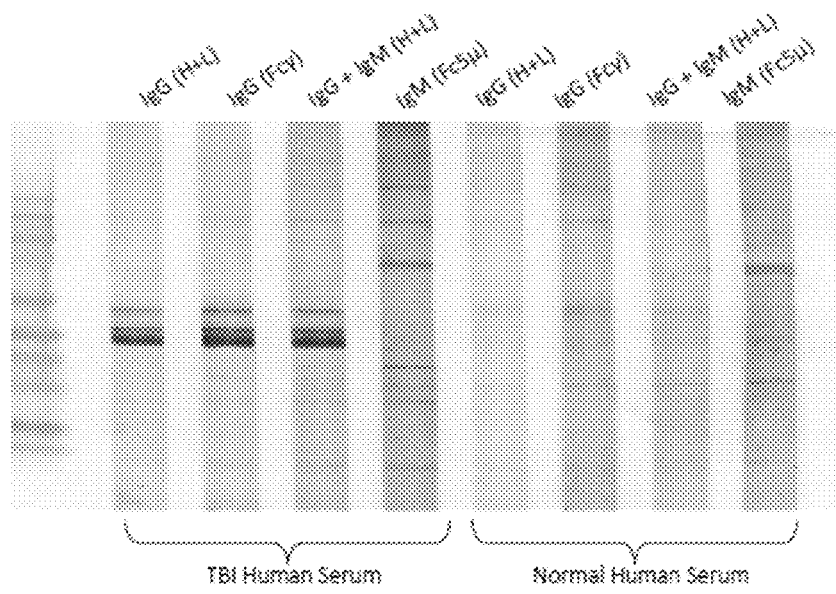
Figure 19:
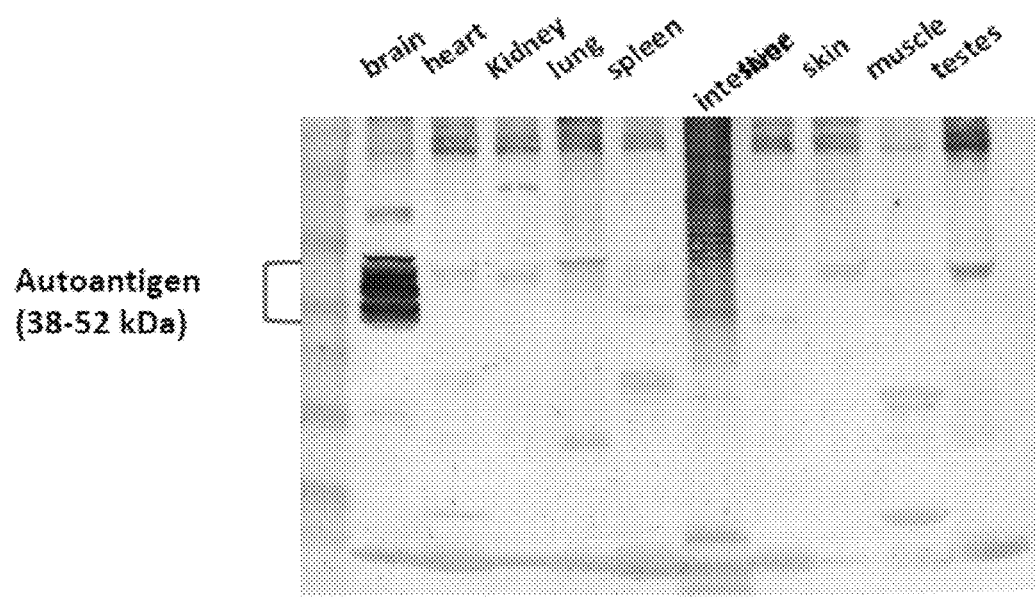
Figure 20:
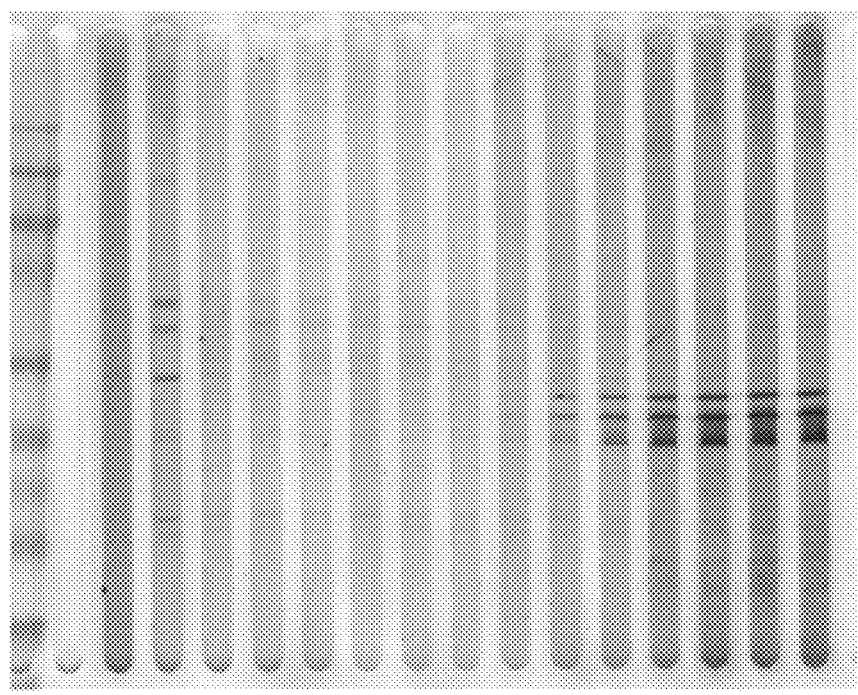
Figure 21:
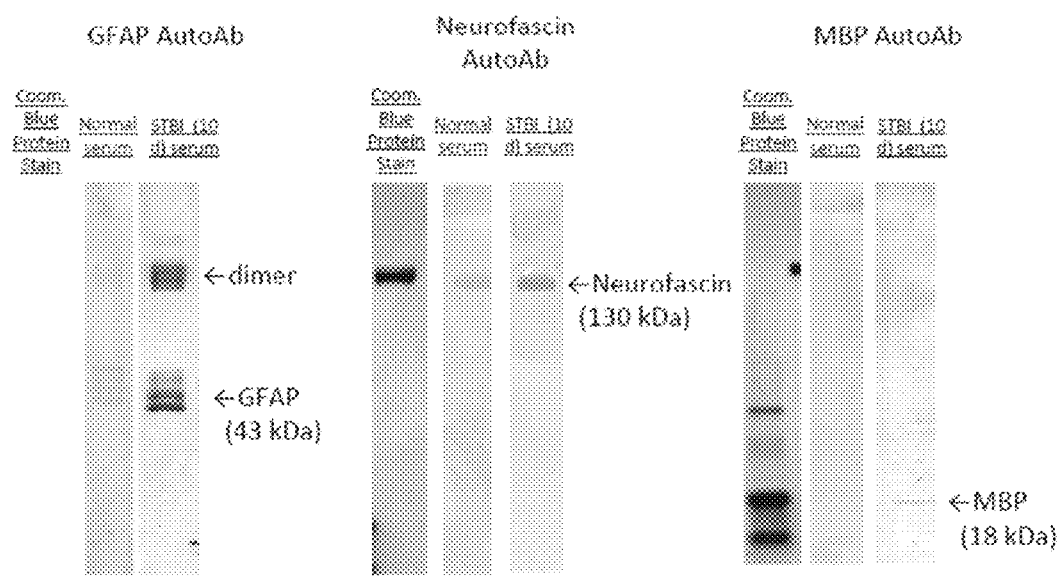
Figure 22A:
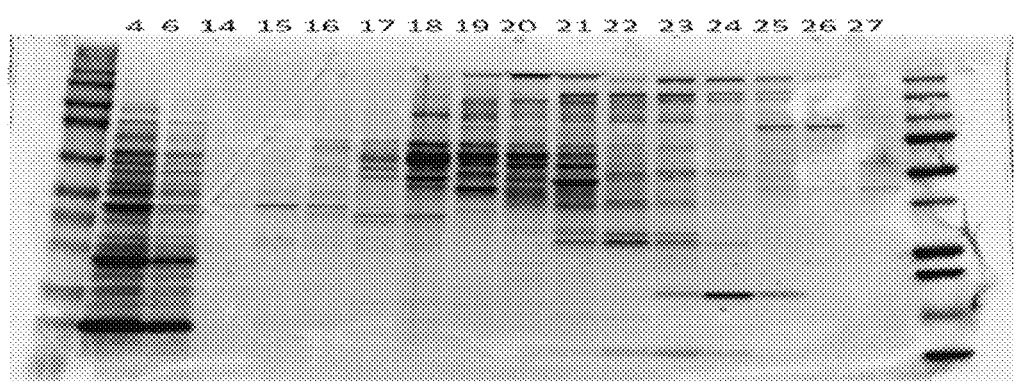
Figure 22B:
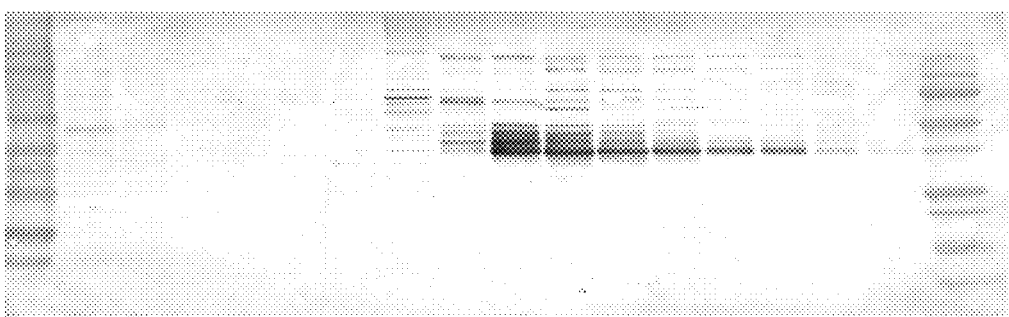
Figure 23:
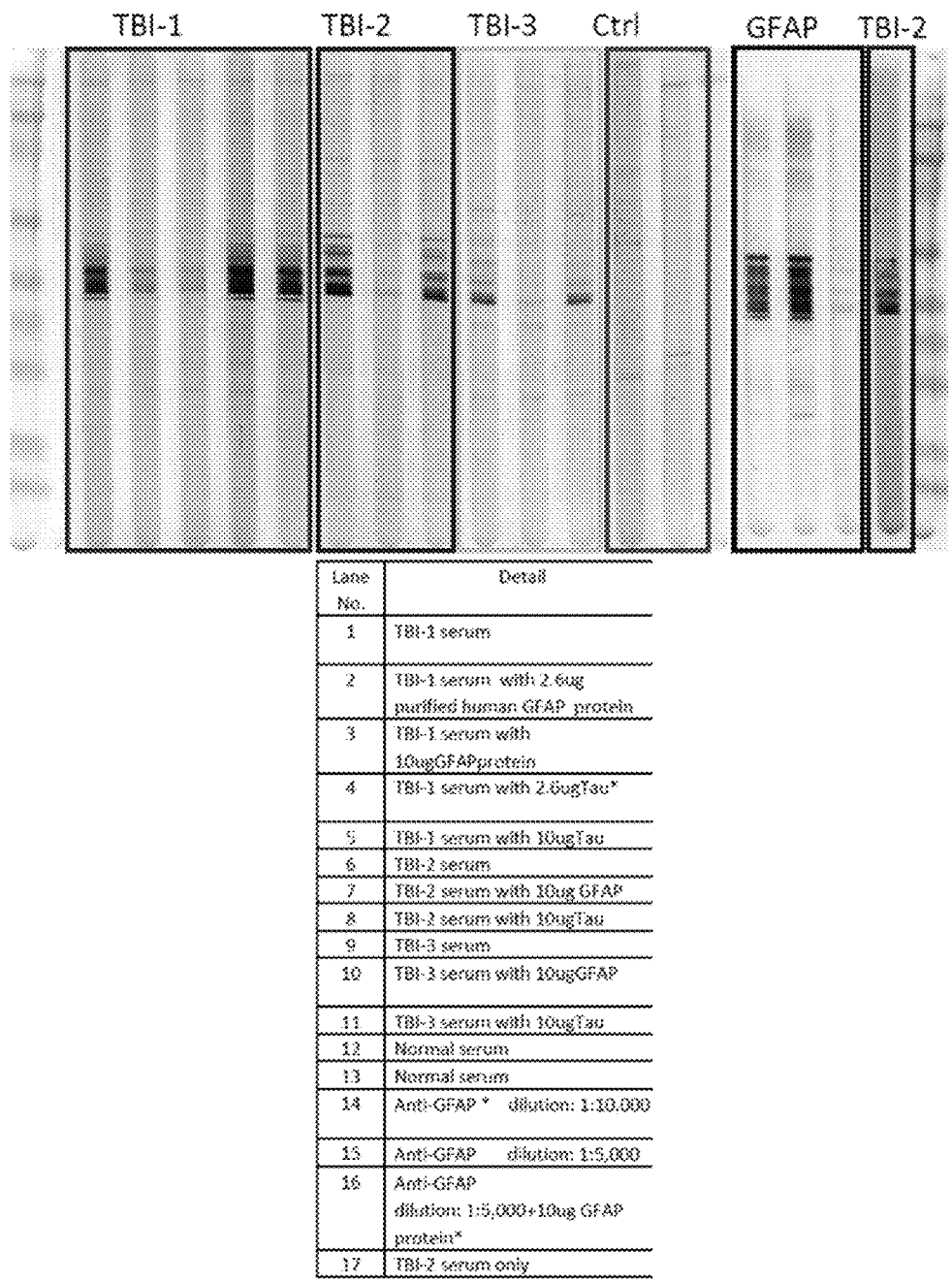
Figures 24A, 24B, 24C:
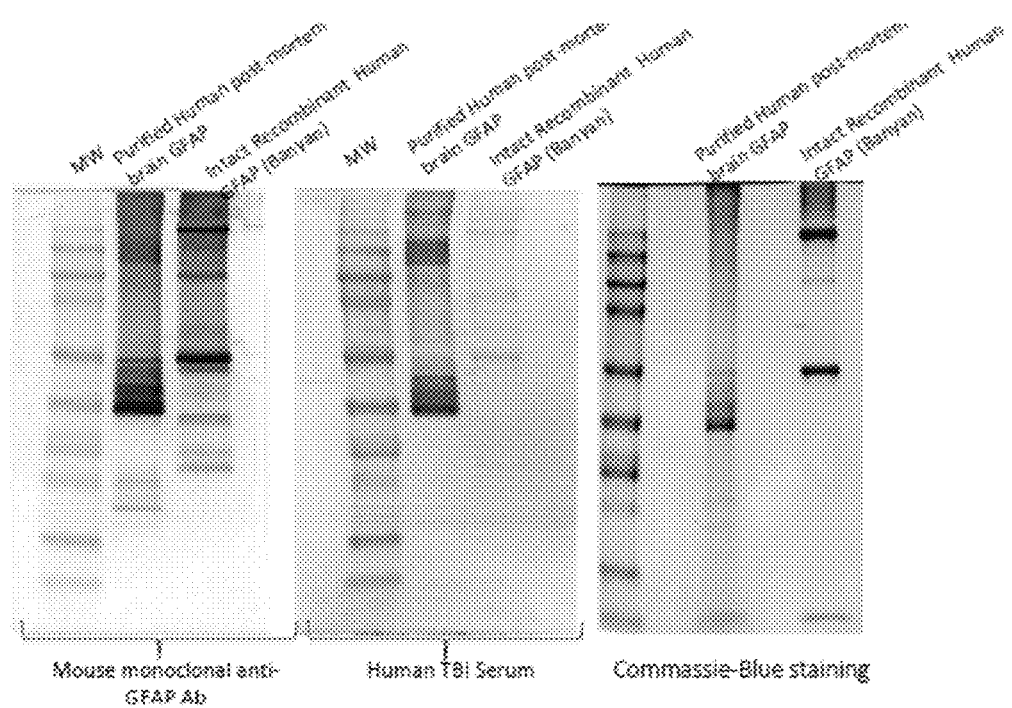
Figure 25:
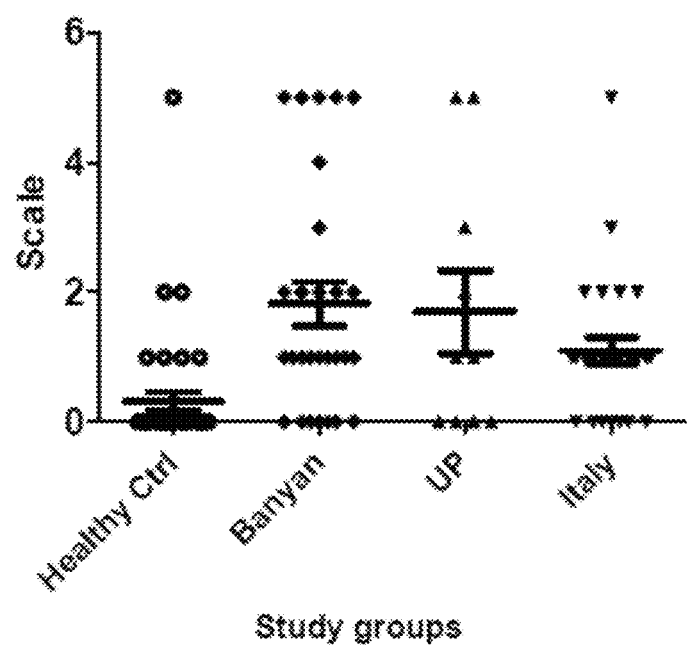
Figure 27:
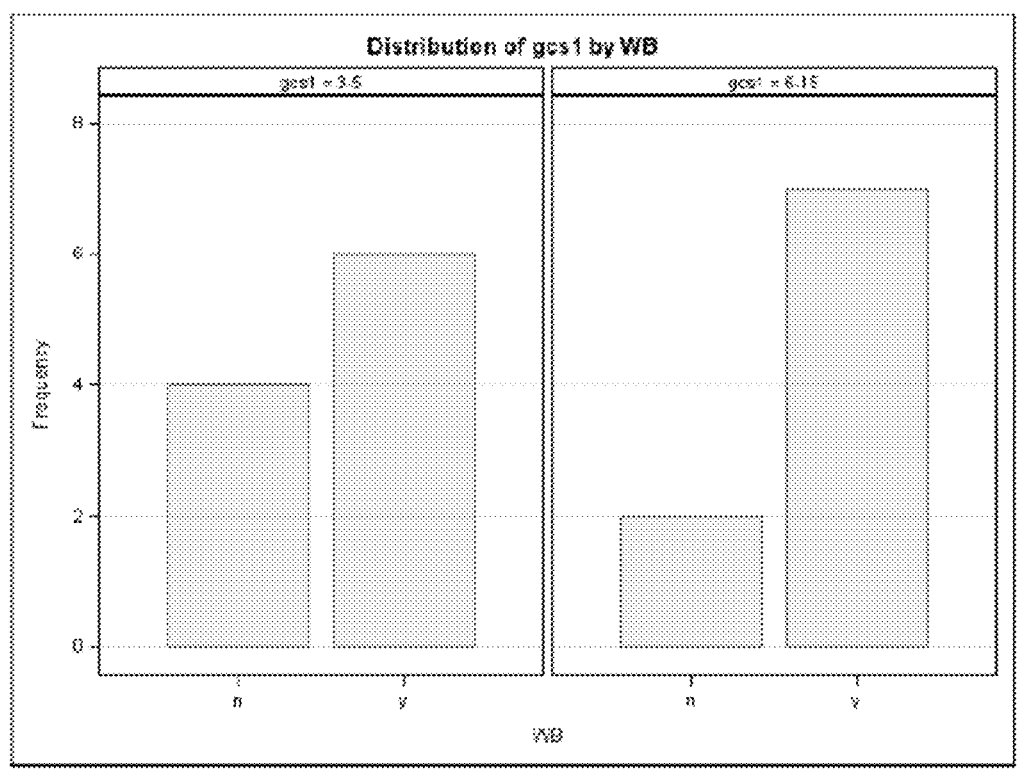
Figure 28:
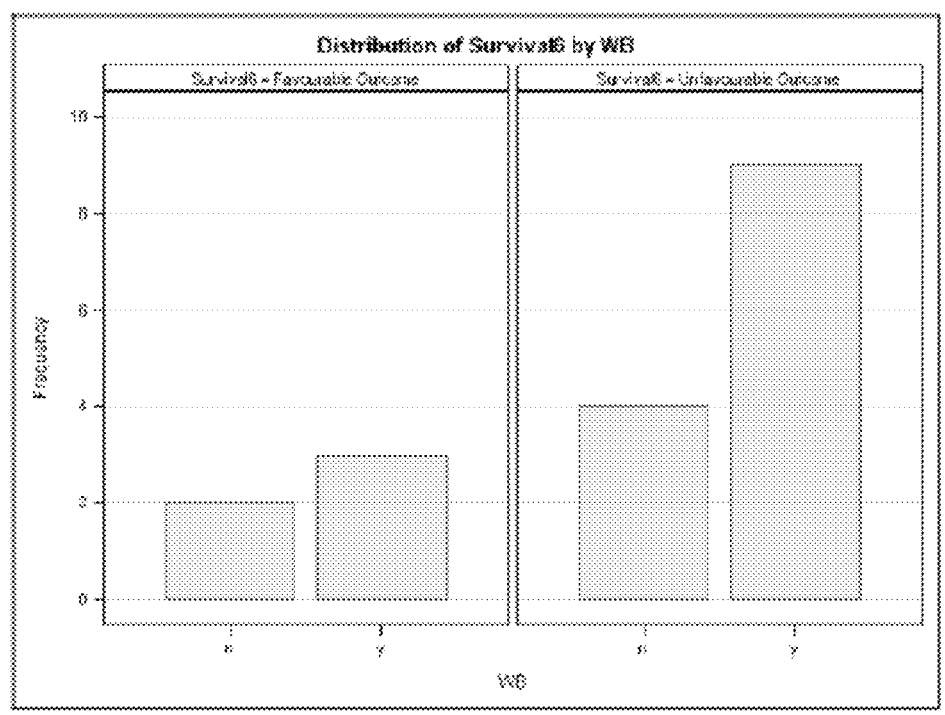
Figure 29A:
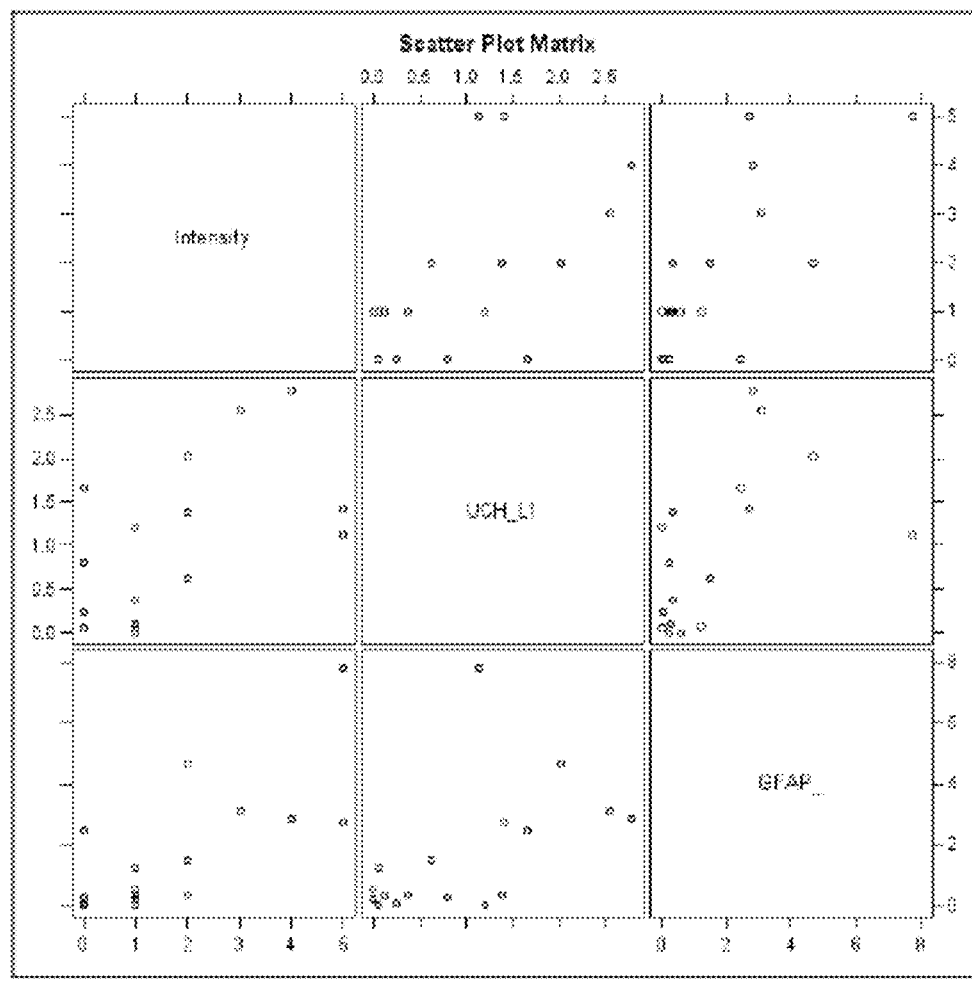
Figure 29B:
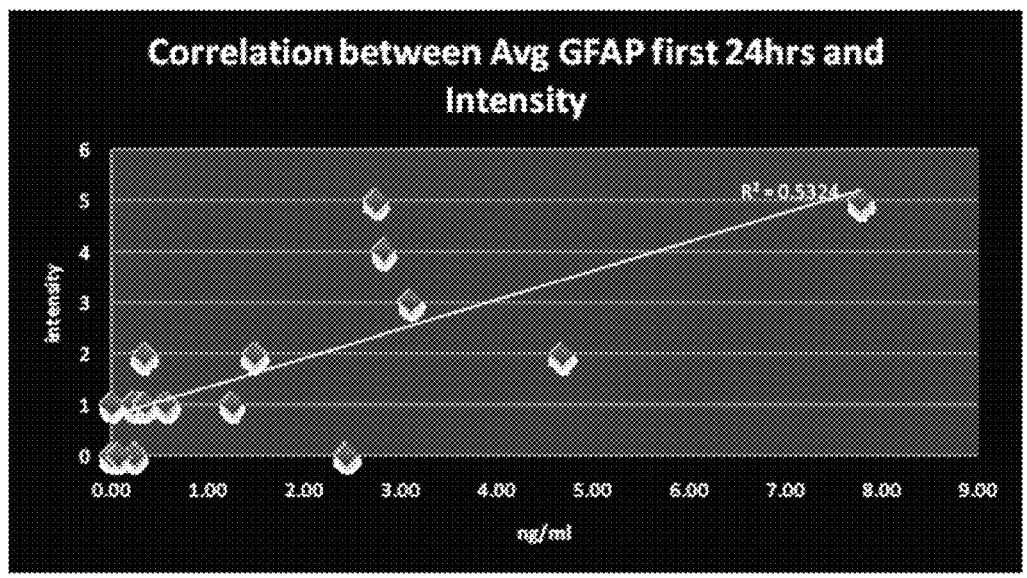
Figure 30:
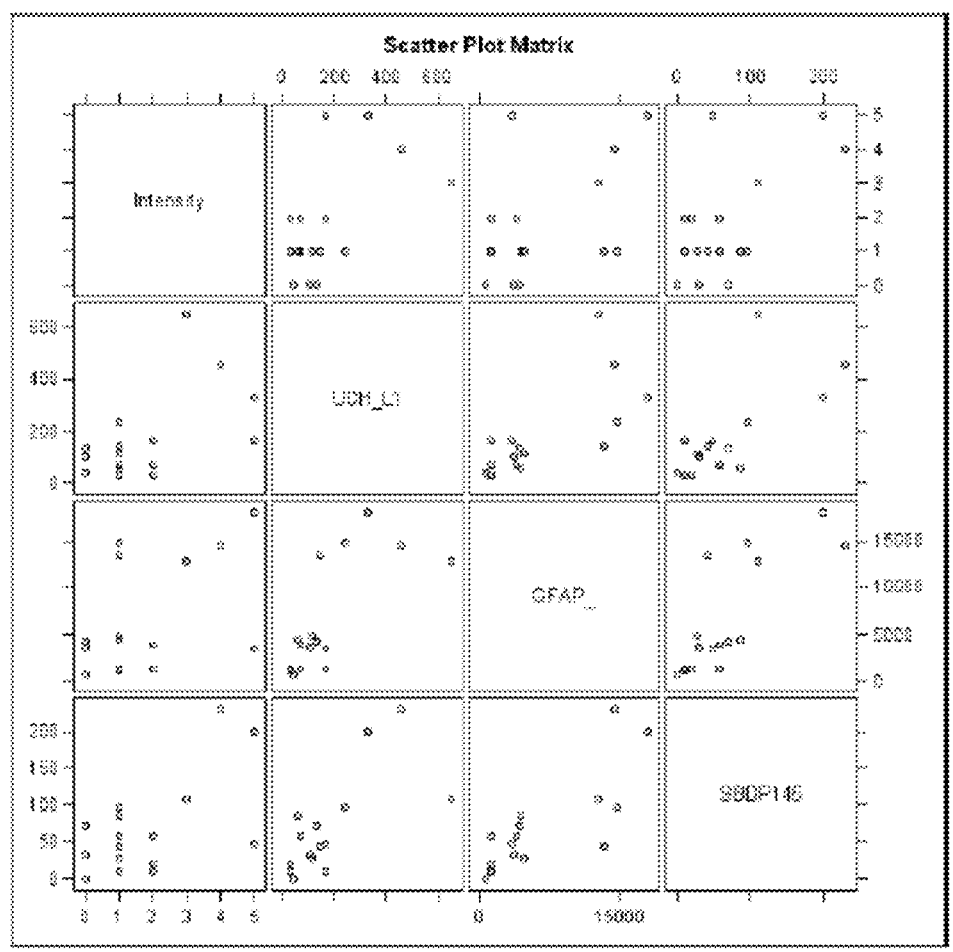
Figure 31A:
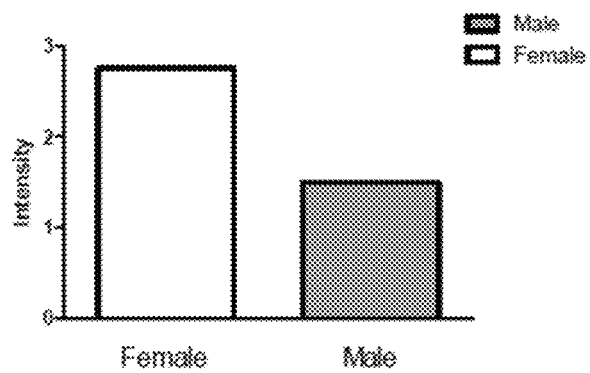
Figure 31B:
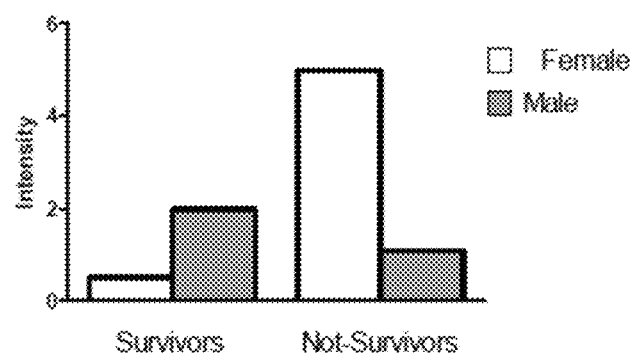
Figure 31C:
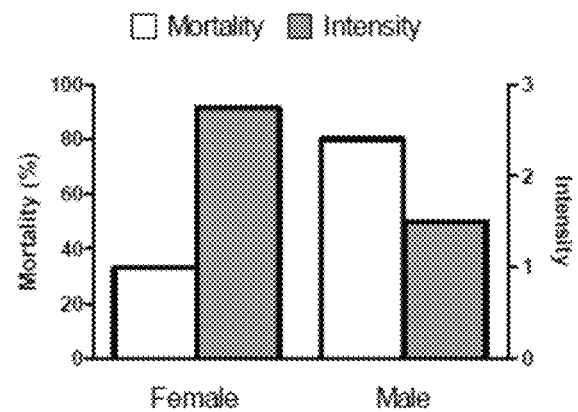
Figure 32A:
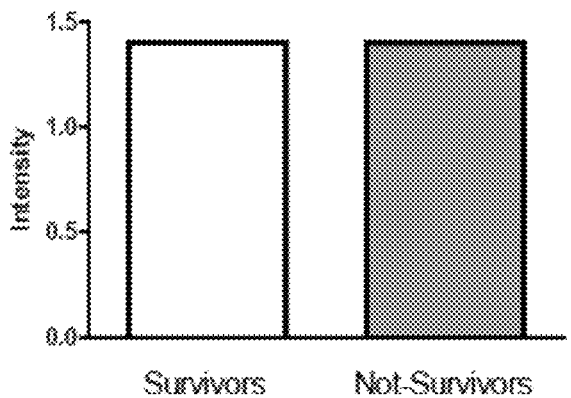
Figure 32B:
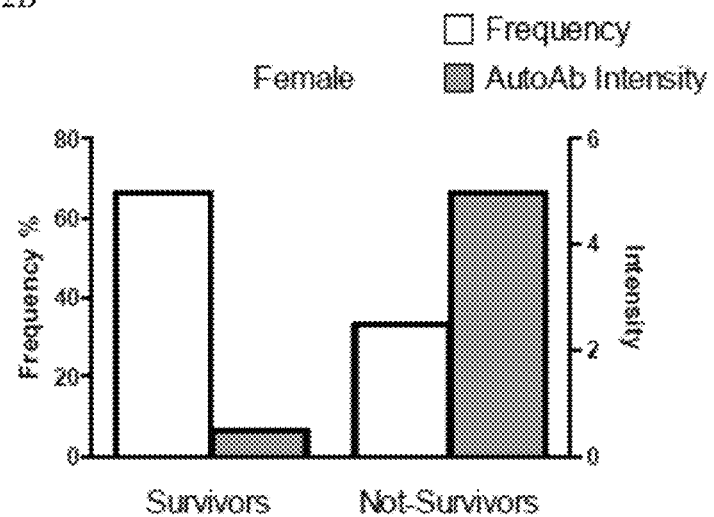
Figure 32C:
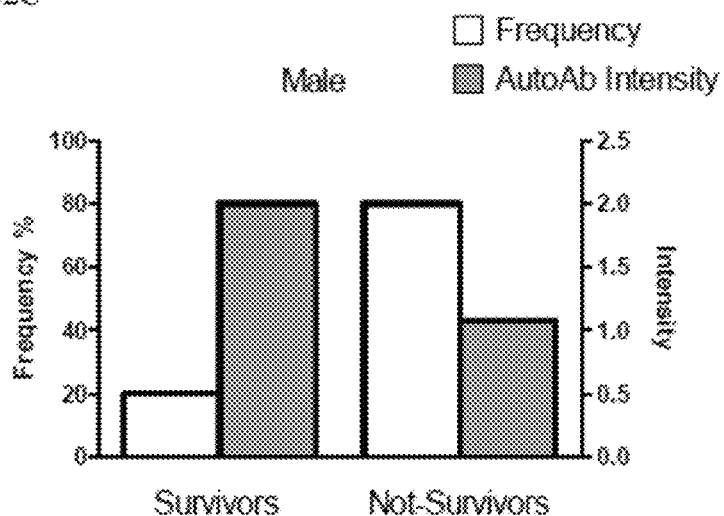
Figure 33:
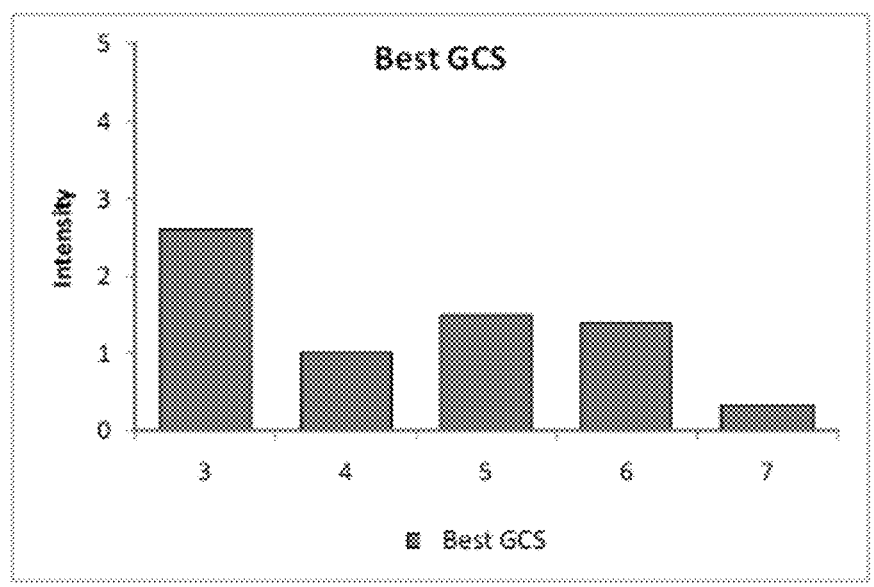
Figure 34:
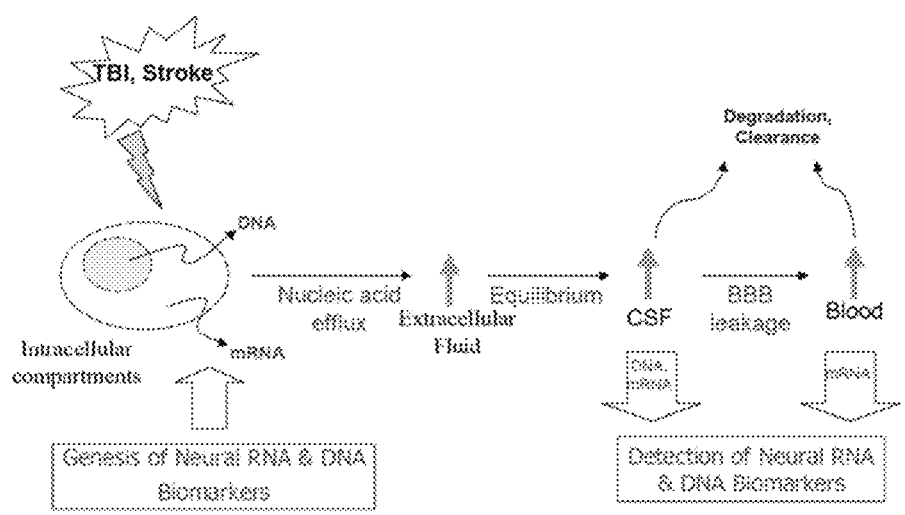
Figure 35:
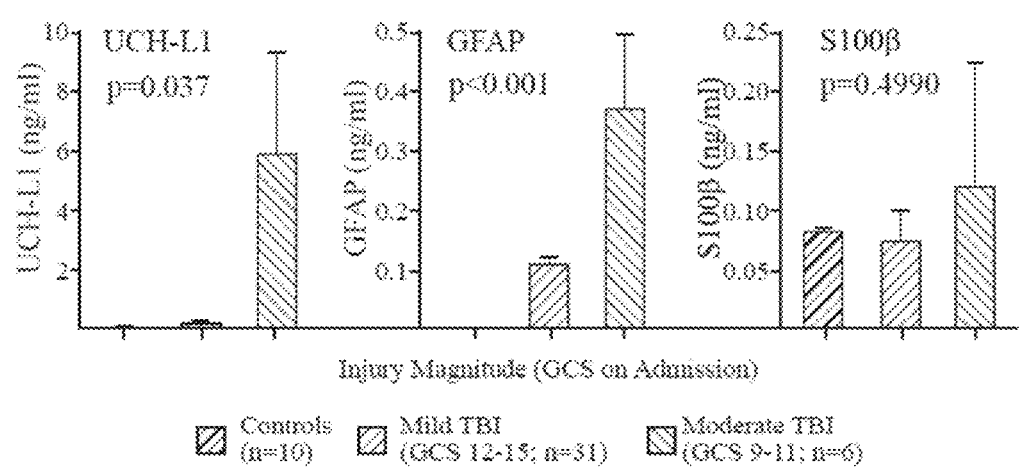
Figure 36:
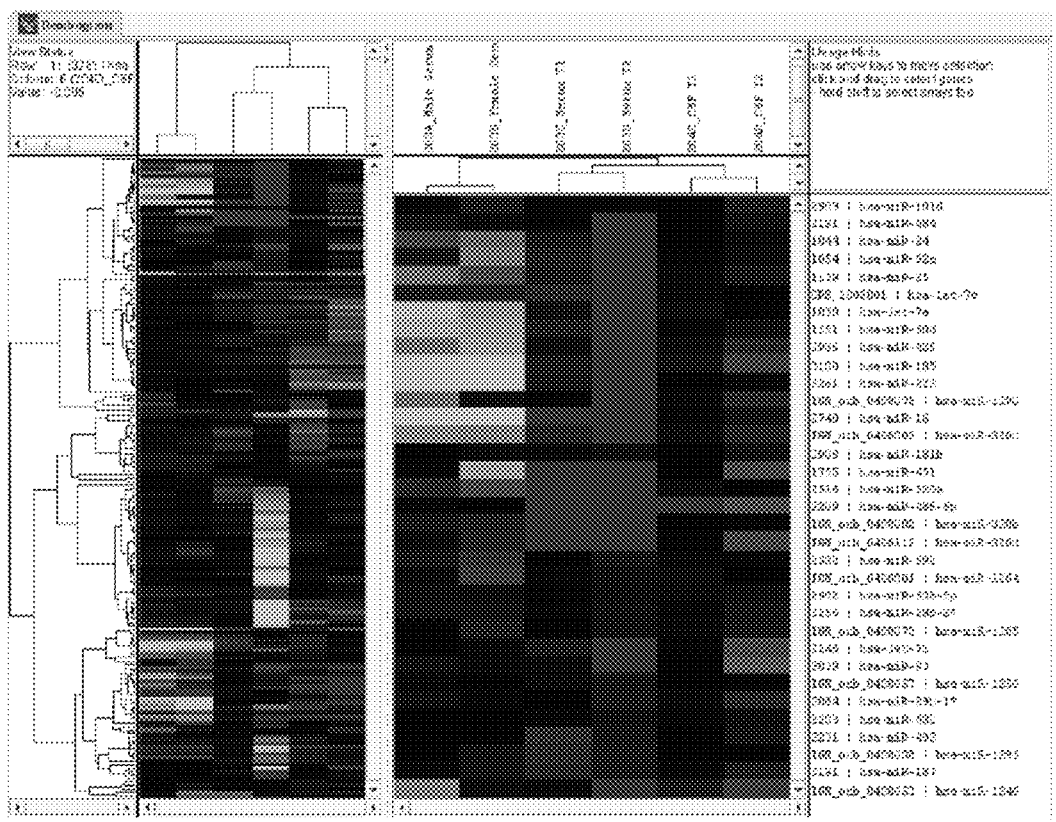
Figure 37:
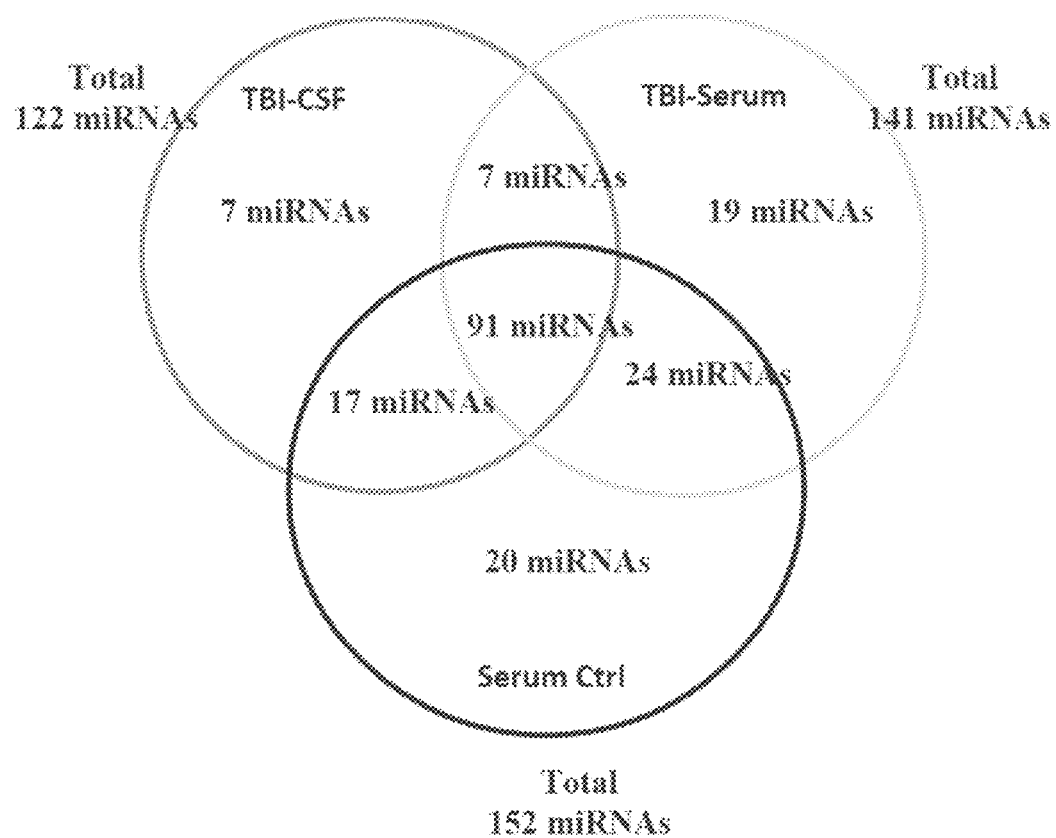

FIG. 11A-B illustrates Tau and TBDPs following CCI challenge in rats in cortex, FIG. 11C-D illustrates Tau and TBDPs following CCI challenge in rats in hippocampus;

FIG. 12A-B illustrates calpain-1 specific cleavage in rat cortex following experimental CCI;

FIG. 13A-B illustrates activation of calpain-1 and calpain-2 in rat cortex following CCI;

FIG. 14A illustrates the calpain specificity of Tau-BDP35K by administration of SNJ-1945 in vivo immediately after CCI as observed by western blot and FIG. 14B illustrates the calpain specificity of Tau-BDP35K by administration of SNJ-1945 in vivo immediately after CCI as observed by densitometric analyses thereof;

FIG. 15A-B are western blots of human CSF for GFAP and GBDPs in two patients at various time points following injury;

FIG. 16A illustrates the presence of human serum autoantibodies directed to brain specific proteins found in post-mortem human brain protein lysate where total protein load is measured by Coomassie brilliant blue stain, FIG. 16B shows western blot probing with control serum, or FIG. 16C shows western blot probing with pooled post-TBI patient serum;

FIG. 17 illustrates the presence of autoantibodies in serum from human subjects at 72 hours and 30 days post-TBI;

FIG. 18A illustrates the presence of autoantibody in the serum from a human subject detectable within 5 days following TBI and FIG. 18B illustrates their IgG specificity is confirmed;

FIG. 19 illustrates that the TBI induced autoantigens are brain specific;

FIG. 20 illustrates that autoantibodies in human serum recognize calpain specific cleavage products of rat brain;

FIG. 21 illustrates the presence of autoantibodies to GFAP, neurofascin, and MBP in serum from a human TBI subject obtained 10 days following injury;

FIG. 22A illustrates ion exchange fractions of human brain lysate stained by Coomassie blue and FIG. 22B illustrates ion exchange fractions of human brain lysate probed by western blot using serum from a human subject obtained 10 days following TBI where sequencing of overlapping bands indicates that autoantibodies are directed to GFAP and other proteins listed in Table 2;

FIG. 23 illustrates antigen competition experiments indicating the presence of autoantibodies to GFAP in human serum post-TBI;

FIG. 24A-C illustrates autoantibody preferential recognition of calpain mediated GFAP breakdown products instead of intact GFAP;

FIG. 25 illustrates the presence of autoantibodies in serum from human TBI patients across several study groups;

FIG. 26 illustrates gender and age differences with respect to the levels of autoantibodies in serum following TBI in a human study;

FIG. 27 illustrates increased levels of autoantibodies in TBI diagnosed subjects broken down by GCS score;

FIG. 28 illustrates the correlation of autoantibodies with survival at 6 months;

FIG. 29 illustrates the correlation between serum GFAP and UCHL1 levels and autoantibody intensity (A) illustrates scatter plots and (B) illustrates correlations;

FIG. 30 illustrates the correlation between CSF GFAP, UCHL1, and SBDP145 and autoantibody intensity;

FIG. 31A illustrates autoantibody intensity as a function of gender; FIG. 31B illustrates autoantibody intensity as a function of outcome; and FIG. 31C illustrates autoantibody intensity and mortality as a function of gender;

FIG. 32A illustrates the intensity of autoantibodies as a function of survival and FIG. 32B-C illustrates the intensity and propensity of autoantibodies as a function of survival for females and males;

FIG. 33 illustrates the intensity of autoantibodies as a function of GCS score;

FIG. 34 is a schematic of nucleic release by neuronal cells during neuronal injury;

FIG. 35 illustrates the level of GFAP, UCHL1 and S100β in serum from TBI human subjects with mild and moderate injury magnitude;

FIG. 36 depicts the results of miRNA cluster analyses;

FIG. 37 is a schematic of the number of identified miRNAs in biological samples.

DESCRIPTION OF THE INVENTION

Injury to the brain tissue or the BBB leads to the release of intracellular molecules such as proteins, degraded protein fragments, DNA and RNA (including miRNA) into the cerebrospinal fluid (CSF) or the blood stream. The leakage of these antigens may lead to formation of the autoantibodies against them. The present invention capitalizes on measurement the increased or decreased quantity of these inventive neuron specific biomarkers in a biological sample, and as such, has utility in the diagnosis and management of abnormal neurological condition. Specifically, the invention has utility as a diagnostic to identify or classify neuronal injury including injury related to disease, illustratively a traumatic brain injury (TBI) and subtypes thereof, as well as for identifying potential therapeutics effective for the particular brain injury type the subject has endured.

The processes have utility to detect a neurological trauma or condition that is predictive or indicative of future disease or injury. Illustratively, the processes have utility as a safety or efficacy screening protocol for in vivo or in vitro drug development. Drug development is not limited to drugs directed to neurological conditions. The inventive biomarkers also have utility to detect expected or unexpected neurological side effects in in vivo animal studies as a means of selecting a lead compound for analyses or as a means of assessing safety of a previously identified drug candidate.

As used herein an "injury" is an alteration in cellular or molecular integrity, activity, level, robustness, state, or other alteration that is traceable to a singular or continuing event, optionally a plurality of events. An injury illustratively includes an event that is physical, mechanical, chemical, biological, functional, infectious, or other modulator of cellular or molecular characteristics. An injury is illustratively the result of a physical trauma such as an impact (e.g. percussive) or a biological abnormality such as a stroke resulting from either blockade or leakage of a blood vessel. An exemplary impact injury is traumatic brain injury (TBI). An injury is optionally an infection by an infectious agent. In some embodiments, an injury is exposure to a chemical compound. A person of skill in the art recognizes numerous equivalent injuries that are encompassed by the terms injury or event.

An injury is optionally a physical event such as a percussive impact. An impact is the like of a percussive injury such as resulting from a blow to the head that either leaves the cranial structure intact or results in breach thereof. Experimentally, several impact methods are used illustratively including controlled cortical impact (CCI) such as at a 1.6 mm depression depth, equivalent to severe TBI in humans. This method is described in detail by Dixon, C E, et al., *J Neurotrauma*, 1999; 16(2):109-22. It is appreciated that other experimental methods producing impact injury are similarly operable.

TBI may also result from stroke. Ischemic stroke is optionally modeled by middle cerebral artery occlusion (MCAO) in rodents. UCHL1 protein levels, for example, are increased following mild MCAO, which is further increased following severe MCAO challenge. Mild MCAO challenge may result in an increase of biomarker levels within two hours that is transient and returns to control levels within 24 hours. In contrast, severe MCAO challenge results in an increase in biomarker levels within two hours following injury and may be much more persistent demonstrating statistically significant levels out to 72 hours or more.

Without being restricted to one theory or model, one proposed delineation between mild-traumatic brain injury (mTBI) and TBI are the recognizable increase or decrease in molecular biomarkers in biological fluids following injury. Illustrative examples of molecular markers include those described by Kobeissy F H, et al., *Mol Cell Proteomics*, 2006; 5:1887-1898. An exemplary definition of TBI is the presence of at least one recognizable biomarker with at least two-fold increased or decreased biomarker levels.

The term "biomarker" as used herein is a protein, nucleic acid, or other differentiator useful for measurement of biological activity or response. A neuron specific biomarker is a biomarker with relevance to neuronal or glial structure, function, or activity. A protein is illustratively an antibody or a breakdown product of a physiological protein. A "nucleic acid" or "oligonucleotide" is defined herein as a macromolecule composed of two or more nucleotides such as deoxyribonucleotides, or ribonucleotides. Biomarkers used herein are illustratively neuron specific or enriched biomarkers, that is to say that biomarkers are molecules that are not normally found at appreciable levels outside of one or more neuron types. Biomarkers illustratively include: one or more breakdown products of a protein, illustratively GFAP, αII-spectrin, UCHL1, among others; antibodies; DNA; RNA; miRNA; or one or more fragments of RNA, DNA, peptides, proteins, or other biological material whose presence, absence, level or activity is correlative of or predictive of neurological damage or disease.

In some embodiments, a biomarker is an antibody, illustratively, an autoantibody. An autoantibody is an antibody that recognizes, binds, or otherwise interacts with an antigen normally found in a subject, or a tissue or cell of a subject. An antigen is illustratively GFAP; αII-spectrin; neurofascin; MBP; MAP2; a ubiquitin carboxyl-terminal esterase; a ubiquitin carboxyl-terminal hydrolase; a neuronally-localized intracellular protein; microtubule associated protein tau (MAP-tau); Poly (ADP-ribose) polymerase (PARP); collapsin response mediator proteins (CRMP-1 to 5); breakdown products thereof, any other biomarker listed in one or more tables or references herein, and combinations thereof.

Alternatively or in addition, a biomarker is a portion of a protein that is GFAP, neuron specific enolase (NSE), ubiquitin C-terminal hydrolase L1 (UCHL1), Neuronal Nuclei protein (NeuN), 2',3'-cyclic nucleotide 3'-phosphodiesterase (CNPase), Soluble Intercellular Adhesion Molecule-1 (sICAM-1), inducible nitric oxide synthase (iNOS), any other biomarker listed in one or more tables or references herein, and combinations thereof. Illustratively, neuron specific enolase (NSE) is found primarily in neurons; GFAP is found in astrocytes; and CNPase is found in the myelin of the central nervous system. As such, a biomarker is illustratively a breakdown product (BDP) of a protein. Numerous methods of producing breakdown products are known in the art. Illustratively, calpain or caspase proteolytic cleavage of a neuronal specific protein produce one or more BDPs of that protein.

A biomarker is optionally a nucleic acid. Nucleic acids illustratively are oligoribonucleotides or oligodeoxyribonucleotides. As such a nucleic acid biomarker is optionally DNA or RNA that encodes at least a portion of a protein expressed in a neuron. Circulating DNA has been used for studies in systemic lupus and rheumatoid arthritis because in these diseases the amount of DNA in the blood is rather high (Tan et al, 1966). Free DNA in serum has also been suggested as a biomarker for specific cancers (Leon et al., 1977). Methylated DNA (Muller et al., 2003) and free DNA with specific mutations (Silva et al, 1999) have been found in plasma and linked to cancer. It has also been possible to find fetal DNA in maternal plasma and serum (Lo et al., 1997). Circulating DNA has been found in the plasma of patients with acute stroke (Rainer et al., 2003). Thus, circulating levels of DNA may correlate with disease. The inventors have discovered that neuronal injury leads to increases in the levels of circulating DNA of neuronal origin. Measuring increased DNA levels in the CSF or serum is an indicator of neuronal injury and injury severity.

It has been believed that RNA would not function as a marker of disease or injury due to RNA being easily degraded in the blood. While this is the case for exogenously added RNA, the endogenous RNA from tissues that have suffered trauma may show greater stability and thus be useful as a biomarker. Without being limited to one particular theory, endogenous RNA may be complexed with proteins and protected from degradation when in apoptotic bodies (Hasselman et al., 2001). Moreover, RNA may be more specific to site of injury and type of disease due to the ability to readily identify its sequence and correlate this sequence with a cell type specific expression of the RNA. As such, a biomarker is optionally an RNA molecule. RNA molecules include mRNA, rRNA, miRNA, tRNA, and miRNA.

A biomarker is optionally a miRNA. MicroRNAs (miRNAs) are non-coding RNA molecules that are able to regulate gene expression post-transcriptionally through degradation of the messenger RNA hence reducing protein expression. A miRNA biomarker is a miRNA that regulates the expression of a gene encoding one or more neuron specific proteins such as any of those listed in the tables or otherwise herein.

A process includes measuring the quantity of one or more biomarkers in a biological sample. A biomarker is measured by any method or process known in the art or described herein for determining an absolute quantity, relative quantity, or value representative of quantity e.g. increased or decreased fluorescence relative to background or other comparator. Optionally, one, two, three, four, or more biomarkers are measured simultaneously or sequentially from one or more biological samples. A second or additional biomarker is optionally different from a first biomarker.

A biomarker illustratively is a breakdown product of a protein, binds to a protein or portion thereof, encodes a protein or portion thereof, or regulates the expression of a protein, where the protein is: ubiquitin carboxyl-terminal esterase L1 (UCHL1); neuron specific enolase (NSE); a spectrin breakdown product (SBDP), illustratively SBDP150, SBDP150i SBDP145, or SBDP120; S100 calcium binding protein B (S100β); microtubule associated protein (MAP), optionally MAP2, MAP1, MAP3, MAP4, MAP5; myelin basic protein (MBP); Tau, illustratively MAP-tau or tau BDPs; Neurofilament protein (NF); Cannabinoid Receptor (CB); CAM proteins; synaptic protein; collapsin response mediator proteins (CRMP-1 to 5); inducible nitric oxide synthase (iNOS); neuronal nuclei protein (NeuN); cysteinyl-specific peptidase (CSPase); neuroserpin; alpha-internexin; light chain 3 protein (LC3); neurofascin; the glutamate transporters (EAAT); nestin; cortin-1, 2',3'-cyclic nucleotide 3'-phosphodiesterase (CNPase); βIII-tubulin, or any biomarker listed in Table 1, or other table herein, or combinations thereof.

TABLE 1

| Glycogen phosphorylase, (BB-form)GP- | | |
|---|---|---|
| UCHL1 | BB | Precerebellin |
| MBP isoforms | CRMP-2 | Cortexin |
| SBDP150 (calpain) | NP25, NP22; Transgelin-3 | EMAP-II |
| SBDP120 (caspase) | SBDP150i (caspase) | Calcineurin-BDP |
| MBP-fragment (10/8K) | CaMPK-IIα | MAP2 |
| SBDP145 | MOG | N-Cadherin |
| Synaptophysin | PLP | N-CAM |
| βIII-Tubulin | PTPase (CD45) | Synaptobrevin |
| Tau-BDP-35K (calpain) | Nesprin-BDP | MAP1A (MAP1) |
| NF-L-BDP1 | OX-42 | MAP1B (MAP5) |
| NF-M-BDP1 | OX-8 | Prion-protein |
| NF-H-BDP1 | OX-6 | PEP19; PCP4 |
| Synaptotagmin | CaMPKIV | Synaptotagmin-BDP1 |
| PSD93-BDP1 | Dynamin | BDNF |
| AMPA-R-BDP1 | Clathrin HC | Nestin |
| NMDA-R-BDP | SNAP25 | IL-6 |
| SBDP150i (caspase) | Profilin (BDP?) | IL-10 |
| MAP2-BDP1 (calpain) | Cofilin (BDP?) | αII-spectrin SBDP 150 + 145 |
| MAP2-BDP2 (caspase) | APP -BDP (Calpain) | NG2; Phosphacan, neruocan; versican |
| alpha-synuclein | NSF | Ach Receptor fragment (Nicotinic, Muscarinic) |
| Synapsin 1 | IL-6 | I-CAM |
| Synapsin 2-BDP | MMP-9 | V-CAM |
| NeuN | S100β | AL-CAM |
| GFAP | Neuroglobin | CNPase |
| p24; VMP | UCHL1 autoantibody | Neurofascins |
| PSD95 | Tau-BDP-35K (calpain) | Neuroserpin |
| α1,2-Tubulin | Tau-BDP-45K (caspase) | EAAT(1 and 2) |
| β1,2-Tubulin | Huntingtin-BDP-1 (calpain) | Nestin |
| Stathmin-2,3,4 (Dendritic) | Huntingtin-BDP-2 (caspase) | Synaptopodin |
| Striatin-BDP1 | Prion-protein BDP | β-synuclein |
| Snaptojanin-1,2-BDP1 | MBP (N-term half) | Resistin |
| betaIII-Spectrin | Calbindin-9K | Neuropilins |
| betaII-Spectrin-BDP110 (calpain) | Tau-Total | Orexin |
| betaII-Spectrin-BDP85 (caspase) | NSE | Fracktalkine |
| Cannabinoid-receptor1(CB1) | CRMP-1 | β-NGF |
| Cannabinoid-receptor2(CB2) | CRMP-3 | L-selectin |
| MBP isoforms 14K + 17K | CRMP-4 | iNOS |
| Neurocalcin-delta (Glia) | CRMP-5 | DAT |
| Iba1 (Microglia) | Crerbellin 3 | Vimentin |
| Peripherin (PNS) | | Beclin-1 |
| LC3 | | |

A biomarker is optionally a breakdown product of GFAP or Tau. The amino acid sequence of human GFAP is found at GenBank Accession Nos. NP_002046 and NP_001124491 for isoforms 1 and 2 respectively. The amino acid sequence human tau is found at GenBank Accession Nos. NP_005901 and NP_776088. The amino acid sequence rat tau is found at GenBank Accession No. NP_058908 for the 374 amino acid version. The sequences found at each of these accession numbers and other accession numbers found herein are incorporated herein by reference as if each sequence were fully and explicitly listed.

A biomarker is optionally any protein or portion thereof, nucleic acid, or antibody that shows either increased expression or decreased expression during or following an injury or event. Expression is recognized as synthesis whereby increased expression is increased synthesis of the biomarker. Optionally, synthesis is generation of a cleavage product where the protease, e.g. calpain or caspase, cleaves a protein to synthesize or produce a breakdown product. Illustratively, neuronal injury may activate a calpain or caspase that in turn enzymatically cleaves GFAP to produce one or more GBDPs. Thus, the GBDPs are understood to be produced, i.e. synthesized, during or following injury or event. Similarly, autoantibodies are produced over the course of time following or during an injury or event. As such, autoantibodies are understood to be synthesized. Nucleic acids are typically expressed at no or certain levels within a cell. Injury or event may alter the rate at which RNA such as miRNAs are translated from genomic DNA. Thus, it is understood that nucleic acids show either increase or decrease in synthesis during or following an injury or event.

Any number of biomarkers can be detected or measured such as 2, 3, 4, 5, 6, 7, 8, 9, 10, or more. Detection can be either simultaneous or sequential and may be from the same biological sample or from multiple samples from the same or different subjects. Detection of multiple biomarkers is optionally in the same assay chamber. The inventive process optionally further includes comparing the quantity of a first biomarker and the quantity of the at least one additional neuroactive biomarker to normal levels of each of the first biomarker and the one additional neuroactive biomarker to determine the neurological condition of the subject.

The present invention is optionally described with respect to UCHL1 or GFAP. It is appreciated that these biomarkers are presented for illustrative purposes only and are not meant to imply expressly or otherwise that the scope of the present invention is limited to UCHL1 or GFAP.

In some embodiments a biomarker is a breakdown product of GFAP (GBDP). GFAP is associated with glial cells such as astrocytes. A biomarker is optionally one or more GBDP. GDBPs optionally have a migratory molecular weight between 38 to 52 kDa. A GDBP is optionally a product of proteolytic digestion of GFAP. Illustrative proteases include calpain and caspase.

In some embodiments a biomarker is a nucleic acid such as an oligonucleotide. An oligonucleotide is a DNA or RNA molecule. Preferred examples of RNA molecules are mRNA and miRNA molecules.

RNA molecules were historically believed to have short half-lives in plasma. More recently, studies indicated that RNA molecules may be protected in plasma by protein or lipid vesicles. As such, RNA molecules released following or during an injury, for example, can be detected in whole blood, plasma, serum, CSF, or other biological material and be associated with the presence of injury in the inventive processes. Numerous methods are known in the art for isolating RNA from a biological sample. Illustratively, the methods described by El-Hefnaway, T, et al., *Clinical Chem.*, 2004; 50(3); 564-573, the contents of which are incorporated herein by reference, are operable in the present invention. A biological sample is optionally filtered prior to detecting or measuring a nucleic acid. Filtering removes additional cellular material producing more accurate measurements of biomarker nucleic acids. Methods of filtering a biological sample are known in the art, illustratively as described by Rainer, T H, *Clin. Chem.*, 2004; 50:206-208, the contents of which are incorporated herein by reference.

In some embodiments, RNA encoding or regulating the expression of UCHL1 or GFAP is detected or measured. Human UCHL1 RNA or cDNA derived therefrom is of known sequence and can be found in the NCBI database at accession number NM_004181. A person of ordinary skill in the art knows that other TBI relevant RNA sequences can similarly be found in the NCBI database such as those encoding proteins listed in the tables herein. As further examples, mRNA sequence for GFAP is found at accession number NM_001131019.1 and NM_002055.3 for two isoforms of GFAP.

Exemplary methods of detecting or measuring nucleic acids include methods based on the polymerase chain reaction (PCR), illustratively, PCR or RT-PCR. Nucleic acids can be measured using PCR independent methodologies illustratively, mass spectrometry, fluorescence, staining, other method known in the art. The use of microarrays are optionally employed to detect or measure the level of one or many nucleic acid biomarkers in a sample. Creating and using microarrays for the detection and measurement of nucleic acids is known in the art. Primer and probe designs are also within the level of skill in the art. Any suitable primer and probe as well as labels thereon are operable for the detection of nucleic acid biomarkers in the subject invention. Illustratively, primer and probe design can be performed using automated programs available from commercial sources. Alternatively, numerous commercial suppliers provide primer and probe design services including Applied Biosystems (Foster City, Calif.).

A process of detecting a neurological condition optionally includes obtaining a biological sample from a subject that may be suspected of having a neurological condition; measuring a quantity of a neuron specific biomarker in the sample; comparing the level of the biomarker detected with the level of the same or different biomarker from a subject without a neurological condition to obtain a ratio; and diagnosing or detecting the presence or absence of a neurological condition in the subject based on the ratio.

Optionally, a process involves analyzing the biological sample for the presence of a plurality of biomarkers. A plurality can be any number greater than one. Optionally, two biomarkers are analyzed. Illustratively, the biomarkers are UCHL1 and GFAP related biomarkers. More biomarkers may be simultaneously or sequentially assayed for in the inventive processes illustratively including three, four, five, six, seven, eight, nine, 10, 20, 50, 100, 1000, or any number between or greater.

Illustrative methods for the detection and quantification of biomarkers include real-time PCR (RT-PCR). RT-PCR allows for the simultaneous amplification and quantitation of a plurality of biomarkers simultaneously. Alternatively, mass spectrometry such as electrospray ionization mass spectrometry coupled with time of flight detection and high performance liquid chromatography are similarly operable. It is appreciated that other methods are similarly operable for detection as will be appreciated by one of ordinary skill in the art.

Numerous miRNA molecules are operable as biomarkers in the subject invention. The term "miRNA" is used according to its ordinary and plain meaning and refers to a microRNA molecule found in eukaryotes that is involved in RNA-based gene regulation. Examples include miRNA molecules that regulate the expression of one or more proteins listed in Table 1. Several miRNA molecules have been identified and are operable as biomarkers in the inventive methods. Illustratively, miRNA molecules described by Redell, J B, et al., *J. Neurosci. Res.*, 2009; 87:1435-48; Lei, P., et al., *Brain Res.*, doi:10.1016/j.brainres.2009.05.074; Liu, N, et al., *Exp. Neurology*, 2009; doi:10.1016/j.expneurol.2009.06.015; and Jeyaseelan, K, et al., *Stroke*, 2008; 39:959-966, the contents of each are incorporated herein by reference for the miRNAs defined therein, but also specifically for methods of isolation and quantitation of miRNA described in each reference. These methods, or modifications thereof, are recognized by one of ordinary skill in the art and may be used in the present inventive method.

A process of determining a neurological condition optionally includes detection or measurement of one or more antibodies in a biological sample. An antibody is optionally an autoantibody. Autoantibodies are directed to antigens released from a site of neurological trauma such as TBI, disease, injury or other abnormality. Without being limited to a particular theory, a TBI causes cellular damage that releases intracellular or cell membrane contents into the CSF or bloodstream. The levels of many of these proteins such as those listed in Table 1, and other tables herein, or nucleic acids that encode the proteins or regulate their expression, are not normally present in biological fluids other than the cytoplasm or cell membrane of neuronal tissue such as brain tissue. The presence of these antigens leads to the production of autoantibodies to these antigens within a subject. Detection of an autoantibody as a biomarker is optionally used to diagnose the presence of an abnormal neurological condition in a subject.

U.S. Pat. No. 6,010,854 describes methods of producing antigens and methods of screening for autoantibodies to neuronal glutamate receptors. These methods are equally applicable to the subject invention. As such, U.S. Pat. No. 6,010,854 is incorporated herein by reference for its teaching of methods of producing screening antigens that are operable for screening for autoantibodies. U.S. Pat. No. 6,010,854 is similarly incorporated herein by reference for its teaching of methods of detecting autoantibodies. It is appreciated that other methods of detecting antibodies illustratively including ELISA, western blotting, mass spectrometry, chromatography, staining, and others known in the art are similarly operable.

Several antigens have been discovered as producing autoantibodies following onset of a neurological condition. Such antigens are those illustratively listed in Table 2.

TABLE 2

Exemplary protein autoantigens identified by MS/MS in FIG. 22

GFAP and GBDP
Neurofilament light polypeptide (NF-L)
Neurofilament Medium polypeptide (NF-M)
Neurofilament heavy polypeptide (NF-H)
V-type proton ATPase
Endophilin-A1
Vimentin
Gamma-enolase (NSE)
Microtubule-associated protein 2
Dihydropyrimidinase-related protein 2
Alpha-internexin
Neuroserpin
Neuromodulin
Synaptotagmin-1
Voltage-gated potassium channel In addition several of these and other antigens are associated with brain injury. Illustrative specific examples of autoantigens related to brain injury are listed in Table 3.

TABLE 3

Exemplary autoantigens related to brain injury

αII-spectrin
SBDPs
NSE
UCHL1
MAP2
MBP
Tau
NF-L, M, H
S100B
βIII-tubulin

TABLE 4

Exemplary brain injury-induced autoantigens based on reported antigenicity.

Voltage-gated calcium channel VGCC (P/Q-type)
(as in Lambert-Eaton myasthenic syndrome)
Voltage-gated potassium channel (VGKC)
(as in Limbic encephalitis, Isaac's Syndrome.
Autoimmune Neuromyotonia)
Ri (Anti-neuronal nuclear antibody-2) (as in Opsoclonus)
Hu and Yo (cerebellar Purkinje Cells)
(as in Paraneoplastic cerebellar syndrome)
Amphiphysin (as in Paraneoplastic cerebellar syndrome)
Glutamic acid decarboxylase (GAD)
(as in Diabetes mellitus type 1, Stiff person syndrome)
Aquaporin-4 (Neuromyelitis optica; evic's syndrome)
Basal ganglia neurons (as in Sydenham's Chorea,
Paediatric Autoimmune Neuropsychiatric
Disease Associated with *Streptococcus* (PANDAS)
Homer 3 (subacute idiopathic cerebellar ataxia)
Zic proteins (zinc finger proteins)
(as in Joubert syndrome - cerebellum malformation)
ANNA 3 (brain autoantigen)
Purkinje cell antibody (PCA-2)
PKC γ (paraneoplastic cerebellar degeneration)
SOX1 (Myasthenic Syndrome Lambert-Eaton (LEMS))
Gephyrin (Stiff Man Syndrome)
Ma2
CV2 (=CRMP5)
N-methyl-D-aspartate (NMDA) - develop memory impairment
mGluR1 (Cerebellar ataxia)
Nicotinic acetylcholine receptor (as in Myasthenia gravis)
Recoverin
Enolase
TULIP-1 (tubby-like protein 1)

In some embodiments, full length protein such as any protein listed in Tables 1-4, or a breakdown product thereof, is operable as a screening antigen for autoantibodies. For example, UCHL1 is antigenic and produces autoantibodies in a subject. The sequence for human UCHL1 protein is found at NCBI accession number NP_004172.2. Similarly, the sequence for human GFAP is found at NCBI accession number NP_002046.1. Other illustrative antigens illustratively include αII-spectrin or breakdown products thereof, MAP, Tau, Neurofascin, CRMP-2, MAP2 crude sample, MBP, and human brain lysate or any subfraction thereof.

Any suitable method of producing peptides and proteins of Tables 1-4 is operable herein. Illustratively, cloning and protein expression systems used with or without purification tags are optionally used. Illustrative methods for production of immunogenic peptides include synthetic peptide synthesis by methods known in the art. Chemical methods of peptide synthesis are known in the art and include solid phase peptide synthesis and solution phase peptide synthesis or by the method of Hackeng, T M, et al., *Proc Natl Acad Sci USA*, 1997; 94(15):7845-50, the contents of which are incorporated herein by reference. Either method is operable for the production of antigens operable for screening biological samples for the presence of autoantibodies.

As used herein, "peptide" means peptides of any length and includes proteins. The terms "polypeptide" and "oligopeptide" are used herein without any particular intended size limitation, unless a particular size is otherwise stated.

It is appreciated that the patterns of biomarkers such as RNA, miRNA, DNA, and autoantibodies is operable to locate the site and severity of neuronal abnormality. Illustratively, damage to the brain reveals a different pattern of a plurality of biomarkers than does damage to other regions of the central nervous system. Also, damage to the hippocampus will produce a different pattern of biomarkers than damage to the frontal lobe. As such, localization of injury is achieved by comparative detection of a plurality of biomarkers. For example, miRNA levels within cells are altered in specific patterns in response to TBI. (See Redell, J, et al., *J. Neurosci. Res.*, 2009; 87:1435-1448.) The inventors have surprisingly discovered that the levels of miRNA biomarkers that regulate expression of the proteins in Table 1 are similarly altered by either upregulation or downregulation dependent on the severity of injury or the time since onset of injury. The pattern of miRNA and other biomarkers changes as injury or disease progresses. This may be a result of secondary injury events, delayed cell apoptosis, or other mechanism altering the release of RNA, DNA, or protein. Redell, J, incorporated herein by reference above, illustrates alteration of miRNA biomarkers within cells at 3 hours and 24 hours. Some miRNAs are upregulated at 3 hours whereas others are only upregulated at 24 hours. Similar results are observed for downregulation of miRNA. As such, the regulation of miRNA biomarkers, the method of their detection, and the temporal alteration in expression of Redell, J, et al., *J. Neurosci. Res.*, 2009; 87:1435-1448 are each incorporated herein by reference as equally applicable to the subject invention. Similarly, the temporal nature of miRNA expression in response to stroke as observed by Jeyaseelan, K, et al., *Stroke*, 2008; 39:959-966 is also incorporated herein by reference for the particular miRNAs taught therein as well as the methods of isolation, quantification, and detection taught therein. What was neither appreciated, nor contemplated by prior researchers is that nucleic acid and proteins migrate into the blood or CSF following injury. It was believed that the levels of biomarkers, RNA in particular, would remain localized to the nucleus or possibly the cytoplasm of a cell. The inventor's ability to detect levels of these biomarkers in non-cellular biological samples such as blood (or fraction thereof) or CSF provided a much more robust and simplified detection process for determining the neurological condition or risk of neurological condition in a subject.

As such, in some embodiments screens a biological sample for a first and a second biomarker. Greater numbers are similarly operable. GFAP biomarkers are preferred first biomarkers. As GFAP is associated with glial cells such as astrocytes, preferably the other biomarker is associated with the health of a different type of cell associated with neural function. More preferably, the other cell type is an axon, neuron, or dendrite. Through the use of an inventive assay inclusive of biomarkers associated with glial cells as well as at least one other type of neural cell, the type of neural cells being stressed or killed as well as quantification of neurological condition results. A synergistic measurement of GFAP biomarker optionally along with at least one additional biomarker and comparing the quantity of GFAP biomarker and the additional biomarker to normal levels of the markers provides a determination of subject neurological condition. Specific biomarker levels that when measured in concert with a GFAP biomarker afford superior evaluation of subject neurological condition illustratively include SBDP145 (calpain mediated acute neural necrosis), SBDP120 (caspase mediated delayed neural apoptosis), UCHL1 (neuronal cell body damage marker), and MAP-2.

The nature of a particular protein associated with an inventive biomarker allows tight determination of extent, location, and severity of injury. Table 5 represents biological locations of proteins related to inventive biomarkers. It is appreciated that increases in autoantibodies or RNA, for example, to peripherin equates to different abnormalities than increases in autoantibodies or RNA to UCHL1.

TABLE 5

| Class | Gen#1 | Gen#2 | Gen#3 |
|---|---|---|---|
| Axonal | SBDP145 | βII-SBDP110, | Tau-BDP-14K |
|  | SBDP120 | βII-SBDP-108, -85 | (calp) |
|  | αII-Spectrin | SBDP150 | Tau-BDP-40K |
|  |  |  | (casp) |
| Dendritic | MAP2 | P24 | MAP2-BDP |
|  | βIII-tubulin |  |  |
| Cell body | UCH-L1 | GP-BB | NP25 |
|  |  | Stathmin-2,3 | α-synuclein |
|  |  | PrionProtein | β-synuclein |
| Neuroregen. | CRMP-2 | Nestin |  |
| Nucleus | NeuN |  | Ox-GAPDH |
| Presynaptic | Synaptotagmin | Synaptophysin | Synapsin1,2 |
| Postsynaptic | CaMPKIIa | PSD-93 |  |
|  |  | PSD-95 |  |
| Myelin | MBP-fragment | MOG | MBP-frag |
|  | MBP |  | (New-C) |
| Glia | GFAP |  |  |
| Microglia | IL-6 | Iba1 | OX-8, OX-6 |
|  |  |  | OX-42 |
| Neurovascular. | N-CAM | N-Cadherin | I-CAM, L-CAM |
| PNS |  | Peripherin |  |

Detection of inventive biomarkers is also operable to screen potential drug candidates or analyze safety of previously identified drug candidates. These assays may be either in vitro or in vivo. In vivo screening or assay protocols illustratively include measurement of a biomarker in an animal illustratively including a mouse, rat, or human. Studies to determine or monitor levels such as UCHL1 or GFAP biomarkers are optionally combined with behavioral analyses or motor deficit analyses such as: motor coordination tests illustratively including Rotarod, beam walk test, gait analysis, grid test, hanging test and string test; sedation tests illustratively including those detecting spontaneous locomotor activity in the open-field test; sensitivity tests for allodynia—cold bath tests, hot plate tests at 38° C. and Von Frey tests; sensitivity tests for hyperalgesia—hot plate tests at 52° C. and Randall-Sellito tests; and EMG evaluations such as sensory and motor nerve conduction, Compound Muscle Action Potential (CMAP) and h-wave reflex.

The inventive biomarker analyses are illustratively operable to detect, diagnose, or treat a disease state or screen for chemical or other therapeutics to treat disease. Diseases or conditions illustratively include but are not limited to: neurodegenerative diseases; myelin involving diseases such as multiple sclerosis; stroke; amyotrophic lateral sclerosis (ALS); chemotherapy; cancer; Parkinson's disease; nerve conduction abnormalities stemming from chemical or physiological abnormalities such as ulnar neuritis and carpel tunnel syndrome; other peripheral neuropathies illustratively including sciatic nerve crush (traumatic neuropathy), streptozotozin (STZ) (diabetic neuropathy), and antimitotic-induced neuropathies (chemotherapy-induced neuropathy); experimental autoimmune encephalomyelitis (EAE); delayed-type hypersensitivity (DTH); rheumatoid arthritis; epilepsy; pain; neuropathic pain; and intra-uterine trauma.

Analyses of blast injury to a subject reveal several inventive correlations between biomarkers and neuronal injury. Neuronal injury is optionally the result of whole body blast, blast force to a particular portion of the body, or the result of other neuronal trauma or disease that produces detectable or differentiatable levels of biomarkers. Thus, identifying pathogenic pathways of primary blast brain injury (BBI) in reproducible experimental models is helpful to the development of diagnostic algorithms for differentiating severe, moderate and mild (mTBI) from posttraumatic stress disorder (PTSD). Accordingly, a number of experimental animal models have been implemented to study mechanisms of blast wave impact and include rodents and larger animals such as sheep. However, because of the rather generic nature of blast generators used in the different studies, the data on brain injury mechanisms and putative biomarkers have been difficult to analyze and compare.

To provide correlations between neurological condition and measured quantities of biomarkers, samples of CSF or serum, illustratively, are collected from subjects with the samples being subjected to measurement of biomarkers. A sample is optionally a biological sample. Detected levels of GFAP biomarkers are then optionally correlated with CT scan results as well as GCS scoring. Based on these results, an inventive assay is developed and validated (Lee et al., Pharmacological Research 23:312-328, 2006). It is appreciated that GFAP biomarkers, in addition to being obtained from CSF and serum, are also readily obtained from blood, plasma, saliva, urine, as well as solid tissue biopsy. While CSF is a commonly used sampling fluid owing to direct contact with the nervous system, it is appreciated that other biological fluids have advantages in being sampled for other purposes, and therefore, allow for inventive determination of neurological condition as part of a battery of tests performed on a single sample such as blood, plasma, serum, saliva or urine.

A biological sample is obtained from a subject by conventional techniques. For example, CSF is optionally obtained by lumbar puncture. Blood is optionally obtained by venipuncture, while plasma and serum are obtained by fractionating whole blood according to known methods. It is appreciated that CSF is optionally obtained by cannulation or other technique. Blood is optionally obtained by other technique, illustratively cardiac puncture. Surgical techniques for obtaining solid tissue samples are well known in the art. For example, methods for obtaining a nervous system tissue sample are described in standard neurosurgery texts such as Atlas of Neurosurgery: Basic Approaches to Cranial and Vascular Procedures, by F. Meyer, Churchill Livingstone, 1999; Stereotactic and Image Directed Surgery of Brain Tumors, 1st ed., by David G. T. Thomas, WB Saunders Co., 1993; and Cranial Microsurgery: Approaches and Techniques, by L. N. Sekhar and E. De Oliveira, 1st ed., Thieme Medical Publishing, 1999. Methods for obtaining and analyzing brain tissue are also described in Belay et al., Arch. Neurol. 58: 1673-1678 (2001); and Seijo et al., J. Clin. Microbiol. 38: 3892-3895 (2000).

Optionally, a biomarker is selective for detecting or diagnosing neurological conditions such as brain injury and the like. A biomarker is optionally both specific and effective for the detection and distinguishing levels of TBI. Such biomarkers are optionally termed neuro specific or neuroactive biomarkers.

It is appreciated that the temporal nature of biomarker presence or activity is operable as an indicator or distinguisher of TBI subtype. In a non-limiting example, the severity of experimental middle cerebral artery occlusion (MCAO) correlates with the temporal maintenance of UCHL1 biomarkers in CSF. MCAO of 30 minutes produces transient UCHL1 biomarker levels peaking at 6 hours and rapidly decreasing, whereas MCAO of 2 hours produces sustained UCHL1 biomarker levels for as many as three days. Similarly, the prevalence of other biomarkers at various timepoints following injury is operable to distinguish TBI subtype. GBDP appear in biological samples including human CSF following percussive blast injury within 24 hours after injury and increase in intensity out to as much as 7 days following injury. Similar results are observed for SBDPs such as SBDP 150/145. Autoantibodies are generally observed within five days following injury with increasing amounts to 30 days following injury.

Biomarker analyses are optionally performed using biological samples or fluids. Illustrative biological samples operable herein illustratively include, cells, tissues, cerebral spinal fluid (CSF), artificial CSF, whole blood, serum, plasma, cytosolic fluid, urine, feces, stomach fluids, digestive fluids, saliva, nasal or other airway fluid, vaginal fluids, semen, buffered saline, saline, water, or other biological fluid recognized in the art. In some embodiments, a biological sample is CSF or serum. It is appreciated that two or more separate biological samples are optionally assayed to elucidate the neurological condition of the subject. Optionally, a biological sample is not a cell or cell cytoplasmic or nucleoplasmic material.

In addition to increased cell expression, biomarkers also appear in biological fluids in communication with injured cells. Obtaining biological fluids such as cerebrospinal fluid (CSF), blood, plasma, serum, saliva and urine, from a subject is typically much less invasive and traumatizing than obtaining a solid tissue biopsy sample. CSF, in particular, is commonly used for detecting nerve damage in a subject as it is in immediate contact with the nervous system and is readily obtainable. Serum is a commonly used biological sample as it is easily obtainable and presents much less risk of further injury or side-effect to a donating subject.

To provide correlations between neurological condition and measured quantities of biomarkers, some embodiments of the invention collecting samples of CSF or serum as particular examples from subjects with the samples being subjected to measurement of GFAP related nucleic acids, GBDPs, or GFAP related autoantibodies. The subjects vary in neurological condition. Detected levels of biomarkers are optionally then correlated with CT scan results or GCS scoring. Based on these results, an inventive assay is developed and validated (Lee et al., Pharmacological Research 23:312-328, 2006). It is appreciated that biomarkers, in addition to being obtained from CSF and serum, are also readily obtained from blood, plasma, saliva, urine, as well as solid tissue biopsy. While CSF is a sampling fluid in many embodiments of the invention owing to direct contact with the nervous system, it is appreciated that other biological fluids have advantages in being sampled for other purposes and therefore allow for inventive determination of neurological condition optionally as part of a battery of tests performed on a single sample such as blood, plasma, serum, saliva or urine.

After insult, nerve cells in a subject express altered levels or activities of one or more proteins or nucleic acid molecules than do such cells not subjected to the insult. Thus, samples that contain nerve cells, e.g., a biopsy of a central nervous system or peripheral nervous system tissue are suitable biological samples for use in the invention in some embodiments. In addition to nerve cells, however, other cells expressing illustratively GFAP include, for example, cardiomyocytes, myocytes in skeletal muscles, hepatocytes, kidney cells and cells in testis. A biological sample including such cells or fluid secreted from these cells might also be used in an adaptation of the inventive methods to determine and/or characterize an injury to such non-nerve cells.

A subject illustratively includes a dog, a cat, a horse, a cow, a pig, a sheep, a goat, a chicken, non-human primate, a human, a rat, guinea pig, hamster, and a mouse. Because the present invention optionally relates to human subjects, a subject for the methods of the invention is optionally a human.

Subjects who most benefit from the present invention are those suspected of having or at risk for developing abnormal neurological conditions, such as victims of brain injury caused by traumatic insults (e.g., gunshot wounds, automobile accidents, sports accidents, shaken baby syndrome, other percussive injuries), ischemic events (e.g., stroke, cerebral hemorrhage, cardiac arrest), neurodegenerative disorders (such as Alzheimer's, Huntington's, and Parkinson's diseases; prion-related disease; other forms of dementia), epilepsy, substance abuse (e.g., from amphetamines, Ecstasy/MDMA, or ethanol), and peripheral nervous system pathologies such as diabetic neuropathy, chemotherapy-induced neuropathy and neuropathic pain.

Baseline levels of biomarkers are those levels obtained in the target biological sample in the species of desired subject in the absence of a known neurological condition. These levels need not be expressed in hard concentrations, but may instead be known from parallel control experiments and expressed in terms of fluorescent units, density units, and the like. Typically, in the absence of a neurological condition GBDPs are present in biological samples at a negligible amount. Illustratively, autoantibodies to GFAP or GBDPs are absent in a biological sample form a subject not suspected of having a neurological condition. However, GFAP and GBDPs are often highly abundant in neurons. Determining the baseline levels of GFAP, GBDPs, autoantibodies, and RNA in neurons, plasma, or CSF, for example, of particular species is well within the skill of the art. Similarly, determining the concentration of baseline levels of other biomarkers is well within the skill of the art.

As used herein the term "diagnosing" means recognizing the presence or absence of a neurological or other condition such as an injury or disease. Diagnosing is optionally referred to as the result of an assay wherein a particular ratio or level of a biomarker is detected or is absent.

As used herein a "ratio" is either a positive ratio wherein the level of the target biomarker is greater than the target biomarker in a second sample or relative to a known or recognized baseline level of the same target biomarker. A negative ratio describes the level of the target biomarker as lower than the target biomarker in a second sample or relative to a known or recognized baseline level of the same target biomarker. A neutral ratio describes no observed change in target biomarker. Thus, a quantity of biomarker measured in a biological sample is optionally compared to the level in a control subject to determine if the level in the subject is altered. As such, an altered quantity of a biomarker is a change in the level of biomarker in the biological fluid from a measured or expected value in a control subject. A control subject is a subject with no known neurological injury or disease.

As used herein the term "administering" is delivery of a therapeutic to a subject. The therapeutic is administered by a route determined to be appropriate for a particular subject by one skilled in the art. For example, the therapeutic is administered orally, parenterally (for example, intravenously, by intramuscular injection, by intraperitoneal injection, intratumorally, by inhalation, or transdermally. The exact amount of therapeutic required will vary from subject to subject, depending on the age, weight and general condition of the subject, the severity of the neurological condition that is being treated, the particular therapeutic used, its mode of administration, and the like. An appropriate amount may be determined by one of ordinary skill in the art using only routine experimentation given the teachings herein or by knowledge in the art without undue experimentation.

An exemplary process for detecting the presence or absence of one or more neuroactive biomarkers in a biological sample involves obtaining a biological sample from a subject, such as a human, contacting the biological sample with a compound or an agent capable of detecting of the biomarker being analyzed (i.e. a detection agent), illustratively including a primer, a probe, antibody, aptamer, or an antigen such as in the case of detection of autoantibody biomarkers, and analyzing binding of the compound or agent to the sample after washing. Those samples having specifically bound compound or agent express the marker being analyzed. It is appreciated that other detection methods are similarly operable illustratively contact with a protein or nucleic acid specific stain.

An inventive process can be used to detect biomarkers in a biological sample in vitro, as well as in vivo. The quantity of biomarker in a sample is compared with appropriate controls such as a first sample known to express detectable levels of the marker being analyzed (positive control) and a second sample known to not express detectable levels of the marker being analyzed (a negative control). For example, in vitro techniques for detection of a marker include enzyme linked immunosorbent assays (ELISAs), radioimmuno assay, radioassay, western blot, Southern blot, northern blot, immunoprecipitation, immunofluorescence, mass spectrometry, RT-PCR, PCR, liquid chromatography, high performance liquid chromatography, enzyme activity assay, cellular assay, positron emission tomography, mass spectroscopy, combinations thereof, or other technique known in the art. Furthermore, in vivo techniques for detection of a marker include introducing a labeled agent that specifically binds the marker into a biological sample or test subject. For example, the agent can be labeled with a radioactive marker whose presence and location in a biological sample or test subject can be detected by standard imaging techniques.

Any suitable molecule that can specifically bind or otherwise be used to recognize a biomarker is operative in the invention. An agent for detecting an autoantibody is illustratively an antigen capable of binding to an autoantibody or an antibody capable of binding a biomarker being analyzed. Optionally, an antibody is conjugated with a detectable label. Such antibodies can be polyclonal or monoclonal. An intact antibody, a fragment thereof (e.g., Fab or $F(ab')_2$), or an engineered variant thereof (e.g., sFv) can also be used. Such antibodies can be of any immunoglobulin class including IgG, IgM, IgE, IgA, IgD and any subclass thereof. Antibodies for numerous inventive biomarkers are available from vendors known to one of skill in the art. Illustratively, antibodies directed to inventive biomarkers are available from Santa Cruz Biotechnology (Santa Cruz, Calif.).

RNA and DNA binding antibodies are known in the art. Illustratively, an RNA binding antibody is synthesized from a series of antibody fragments from a phage display library. Illustrative examples of the methods used to synthesize RNA binding antibodies are found in Ye, J, et al., *PNAS USA*, 2008; 105:82-87 the contents of which are incorporated herein by reference as methods of generating RNA binding antibodies. As such, it is within the skill of the art to generate antibodies to RNA based biomarkers.

DNA binding antibodies are similarly well known in the art. Illustrative methods of generating DNA binding antibodies are found in Watts, R A, et al., *Immunology*, 1990; 69(3): 348-354 the contents of which are incorporated herein by reference as an exemplary method of generating anti-DNA antibodies.

An agent or compound for detecting or measuring a biomarker is optionally labeled. A person of ordinary skill in the art recognizes numerous labels operable herein. Labels and labeling kits are commercially available optionally from Invitrogen Corp, Carlsbad, Calif. Labels illustratively include, fluorescent labels, biotin, peroxidase, radionucleotides, or other label known in the art.

Antibody-based assays are useful for analyzing a biological sample for the presence of one or more biomarkers. Suitable western blotting methods are described below in the examples section or are known in the art. For more rapid analysis (as may be important in emergency medical situations), immunosorbent assays (e.g., ELISA and RIA) and immunoprecipitation assays may be used. As one example, the biological sample or a portion thereof is immobilized on a substrate, such as a membrane made of nitrocellulose or PVDF; or a rigid substrate made of polystyrene or other plastic polymer such as a microtiter plate, and the substrate is contacted with an antibody that specifically binds a GFAP biomarker, or one of the other biomarkers under conditions that allow binding of antibody to the biomarker being analyzed. After washing, the presence of the antibody on the substrate indicates that the sample contained the marker being assessed. If the antibody is directly conjugated with a detectable label, such as an enzyme, fluorophore, or radioisotope, the presence of the label is optionally detected by examining the substrate for the detectable label. Alternatively, a detectably labeled secondary antibody that binds the marker-specific antibody is added to the substrate. The presence of detectable label on the substrate after washing indicates that the sample contained the marker. Alternatively, a sandwich assay is used where a specific primary antibody directed to a biomarker is bound to a solid substrate. A biological sample is incubated with the plate and non-specifically bound material is washed away. A labeled or otherwise detectable secondary antibody is used to bind the biomarker affixed to the substrate by the primary antibody. Detection of secondary antibody binding indicates the presence of the biomarker in the biological sample.

Numerous permutations of these basic immunoassays are also operative in the invention. These include the biomarker-specific antibody, as opposed to the sample being immobilized on a substrate, and the substrate is contacted with a biomarker conjugated with a detectable label under conditions that cause binding of antibody to the labeled marker. The substrate is then contacted with a sample under conditions that allow binding of the marker being analyzed to the antibody. A reduction in the amount of detectable label on the substrate after washing indicates that the sample contained the marker.

Although antibodies are useful in the invention because of their extensive characterization, any other suitable agent (e.g., a peptide, an aptamer, or a small organic molecule) that specifically binds a biomarker is optionally used in place of the antibody in the above described immunoassays. For example, an aptamer might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

A myriad of detectable labels that are operative in a diagnostic assay for biomarker expression are known in the art. Agents used in methods for detecting GFAP related or other neuron specific protein related biomarkers are conjugated to a detectable label, e.g., an enzyme such as horseradish peroxidase. Agents labeled with horseradish peroxidase can be detected by adding an appropriate substrate that produces a color change in the presence of horseradish peroxidase. Several other detectable labels that may be used are known. Common examples of these include alkaline phosphatase, horseradish peroxidase, fluorescent compounds, luminescent compounds, colloidal gold, magnetic particles, biotin, radioisotopes, and other enzymes. It is appreciated that a primary/secondary antibody system is optionally used to detect one or more biomarkers. A primary antibody that specifically recognizes one or more biomarkers is exposed to a biological sample that may contain the biomarker of interest. A secondary antibody with an appropriate label that recognizes the species or isotype of the primary antibody is then contacted with the sample such that specific detection of the one or more biomarkers in the sample is achieved.

In some embodiments an antigen is used to detect an autoantibody. Illustratively, an antigen such as GFAP or one or more GBDPs are separated or placed on a substrate such as a PVDF membrane, the membrane is probed with a biological sample such as serum derived from a subject suspected of having a neurological condition, and the presence of an autoantibody is detected by contacting an autoantibody with an antibody type specific antibody such as an anti-IgG alone or combined with anti-IgM antibody that may or may not have a detectable label attached thereto.

A process optionally employs a step of correlating the presence or amount of biomarker such as, GBDPs, or autoantibodies thereto in a biological sample with the severity and/or type of nerve cell injury. The amount of biomarker in the biological sample is associated with a neurological condition such as traumatic brain injury. The results of an assay to measure biomarkers can help a physician or veterinarian determine the type and severity of injury with implications as to the types of cells that have been compromised. These results are in agreement with CT scan and GCS results, yet are quantitative, obtained more rapidly, and at far lower cost.

The present invention provides a step of comparing the quantity of one or more biomarkers to normal levels to determine the neurological condition of the subject. It is appreciated that selection of additional biomarkers allows one to identify the types of cells implicated in an abnormal neurological condition as well as the nature of cell death such as in the case of an axonal injury marker. The practice of an inventive process provides a test that can help a physician determine suitable therapeutics or treatments to administer for optimal benefit of the subject. While the data provided in the examples herein are provided with respect to a full spectrum of traumatic brain injury, it is appreciated that these results are applicable to ischemic events, neurodegenerative disorders, prion related disease, epilepsy, chemical etiology and peripheral nervous system pathologies. A gender difference is optionally considered.

An assay for analyzing cell damage in a subject is also provided. The assay optionally includes: (a) a substrate for holding a biological sample isolated from a subject suspected of having a damaged nerve cell, the sample being a fluid in communication with the nervous system of the subject prior to being isolated from the subject; (b) a biomarker specific binding agent; (c) optionally a binding agent specific for another biomarker; and (d) printed instructions for reacting: the agent with the biological sample or a portion of the biological sample to detect the presence or amount of biomarker, and optionally the agent specific for another biomarker with the biological sample or a portion of the biological sample to detect the presence or amount of the at least one biomarker in the biological sample. The inventive assay can be used to detect a neurological condition for financial renumeration.

The assay optionally includes a detectable label such as one conjugated to the agent, or one conjugated to a substance that specifically binds to the agent, such as a secondary antibody.

The present invention optionally includes the presence of one or more therapeutic agents such as compounds that may alter one or more characteristics of a target biomarker. A therapeutic optionally serves as an agonist or antagonist of a target biomarker or upstream effector of a biomarker. A therapeutic optionally affects a downstream function of a biomarker. For example, Acetylcholine (Ach) plays a role in pathological neuronal excitation and TBI-induced muscarinic cholinergic receptor activation may contribute to excitotoxic processes. As such, biomarkers optionally relate to levels or activity of Ach or muscarinic receptors. Optionally, an operable biomarker is a molecule, protein, nucleic acid or other that is effected by the activity of muscarinic receptor(s). As such, therapeutics operable in the subject invention illustratively include those that modulate various aspects of muscarinic cholinergic receptor activation.

Specific mucarinic receptors operable as therapeutic targets or modulators of therapeutic targets include the $M_1$, $M_2$, $M_3$, $M_4$, and $M_5$ muscarinic receptors.

The suitability of the muscarinic cholinergic receptor pathway in detecting and treating TBI arises from studies that demonstrated elevated ACh in brain cerebrospinal fluid (CSF) following experimental TBI (Gorman et al., 1989; Lyeth et al., 1993a) and ischemia (Kumagae and Matsui, 1991), as well as the injurious nature of high levels of muscarinic cholinergic receptor activation through application of cholinomimetics (Olney et al., 1983; Turski et al., 1983). Furthermore, acute administration of muscarinic antagonists improves behavioral recovery following experimental TBI (Lyeth et al., 1988a; Lyeth et al., 1988b; Lyeth and Hayes, 1992; Lyeth et al., 1993b; Robinson et al., 1990).

A therapeutic compound operable in the subject invention is illustratively any molecule, compound, family, extract, solution, drug, pro-drug, or other mechanism that is operable for changing, preferably improving, therapeutic outcome of a subject at risk for or victim of a neuronal injury such as TBI or MTBI. A therapeutic is optionally a muscarinic cholinergic receptor modulator such as an agonist or antagonist. An agonist or antagonist may by direct or indirect. An indirect agonist or antagonist is optionally a molecule that breaks down or synthesizes acetylcholine or other muscarinic receptor related molecule illustratively, molecules currently used for the treatment of Alzheimer's disease. Cholinic mimetics or similar molecules are operable herein. An exemplary list of therapeutics operable herein include: dicyclomine, scoplamine, milameline, N-methyl-4-piperidinyl-benzilate NMP, pilocarpine, pirenzepine, acetylcholine, methacholine, carbachol, bethanechol, muscarine, oxotremorine M, oxotremorine, thapsigargin, calcium channel blockers or agonists, nicotine, xanomeline, BuTAC, clozapine, olanzapine, cevimeline, aceclidine, arecoline, tolterodine, rociverine, IQNP, indole alkaloids, himbacine, cyclostellettamines, derivatives thereof, pro-drugs thereof, and combinations thereof. A therapeutic is optionally a molecule operable to alter the level of oractivity of a calpain or caspase. Such molecules and their administration are known in the art.

An inventive method illustratively includes a process for diagnosing a neurological condition in a subject, treating a subject with a neurological condition, or both. In some embodiments a process illustratively includes obtaining a biological sample from a subject. The biological sample is assayed by mechanisms known in the art for detecting or measuring the presence of one or more biomarkers present in the biological sample. Based on the amount or presence of a target biomarker in a biological sample, a ratio of one or more biomarkers is optionally calculated. The ratio is optionally the level of one or more biomarkers relative to the level of another biomarker in the same or a parallel sample, or the ratio of the quantity of the biomarker to a measured or previously established baseline level of the same biomarker in a subject known to be free of a pathological neurological condition. The ratio allows for the diagnosis of a neurological condition in the subject. An inventive process also optionally administers a therapeutic to the subject that will either directly or indirectly alter the ratio of one or more biomarkers.

A therapeutic is optionally designed to modulate the immune response in a subject. Illustratively, the levels, production of, breakdown of, or other related parameters of autoantibodies are altered by immunomodulatory therapy. Illustrative examples of immunomodulatory therapies are known in the art that are applicable to the presence of autoantibodies to illustratively GFAP or one or more GBDPs such as therapies used for multiple sclerosis. Such therapies illustratively include administration of glatiramer acetate (GA), beta-interferons, laquinimod, or other therapeutics known in the art. Optionally, combinations of therapeutics are administered as a form of immunomodulatory therapy. Illustrative combinations include IFNβ-1a and methotrexate, IFNβ-1a and azathioprine, and mitoxantrone plus methylprednisolone. Other suitable combinations are known in the art.

An inventive process is also provided for diagnosing and optionally treating a multiple-organ injury. Multiple organs illustratively include subsets of neurological tissue such as brain, spinal cord and the like, or specific regions of the brain such as cortex, hippocampus and the like. Multiple organ injuries illustratively include apoptotic cell death which is detectable by the presence of caspase induced GBDPs, and oncotic cell death which is detectable by the presence of calpain induced GBDPs. The inventive process illustratively includes assaying for a plurality of biomarkers in a biological sample obtained from a subject wherein the biological fluid sampled was optionally in fluidic contact with an organ suspected of having undergone injury or control organ when the biological sample was obtained from the subject. The inventive process determines a first subtype of organ injury based on a first ratio of a plurality of biomarkers. The inventive process also determines a second subtype of a second organ injury based on a second ratio of the plurality of biomarkers in the biological sample. The ratios are illustratively determined by processes described herein or known in the art.

Treatment of a multiple organ injury in the inventive process is illustratively achieved by administering to a subject at least one therapeutic antagonist or agonist effective to modulate the activity of a protein or nucleic acid whose activity or level is altered in response to the first organ injury, and administering at least one therapeutic agonist or antagonist effective to modulate the activity or level of a protein or nucleic acid whose activity is altered in response to a second organ injury.

The invention illustratively includes a composition for distinguishing the magnitude of a neurological condition in a subject. An inventive composition is either an agent entity or a mixture of multiple agents. In some embodiments a composition is a mixture. The mixture optionally contains a biological sample derived from a subject. The subject is optionally suspected of having a neurological condition. The biological sample in communication with the nervous system of the subject prior to being isolated from the subject. In inventive composition also optionally contains at least two primary agents, optionally antibodies or nucleic acids, that specifically and independently bind to at least two biomarkers that may be present in the biological sample. In some embodiments the first primary agent is in antibody that specifically binds GFAP or one or more GBDPs. A second primary agent is optionally an antibody that specifically binds a ubiquitin carboxyl-terminal hydrolase, preferably UCHL1, or a spectrin breakdown product.

The agents of the inventive composition are optionally immobilized or otherwise in contact with a substrate. The inventive agents are also optionally labeled with at least one detectable label. In some embodiments the detectable label on each agent is unique and independently detectable in either the same assay chamber or alternate chambers. Optionally, a secondary agent specific for detecting or binding to the primary agent is labeled with at least one detectable label. In the nonlimiting example the primary agent is a rabbit derived antibody. A secondary agent is optionally an antibody specific for a rabbit derived primary antibody. Mechanisms of detecting antibody binding to an antigen are well known in the art, and a person of ordinary skill in the art readily envisions numerous methods and agents suitable for detecting antigens or biomarkers in a biological sample.

A kit is also provided that encompasses a substrate suitable for associating with the target biomarker in a biological sample. The biological sample is optionally provided with the kit or is obtained by a practitioner for use with an inventive kit. An inventive kit optionally includes at least two antibodies that specifically and independently bind to at least two biomarkers. The antibodies may distinguish between the two biomarkers. Optionally, a first antibody is specific and independent for binding and detecting a first biomarker. A second antibody is specific and independent for binding and detecting a second biomarker. In this way the presence or absence of multiple biomarkers in a single biological sample can be determined or distinguished. Antibodies in the biological sample illustratively include those for biomarkers of αII-spectrin, an αII-spectrin breakdown product (SBDP), a ubiquitin carboxyl-terminal hydrolase, GFAP, GBDP, and a MAP2 protein. An inventive kit also includes instructions for reacting the antibodies with the biological sample or a portion of the biological sample so as to detect the presence of or amount of the biomarkers in the biological sample.

In the kit, the biological sample can be CSF, blood, urine or saliva, and the agent can be an antibody, aptamer, primer, probe, or other molecule that specifically binds at least one biomarker for a neurological condition. Suitable agents are described herein. The kit can also include a detectable label such as one conjugated to the agent, or one conjugated to a substance that specifically binds to the agent (e.g., a secondary antibody).

The invention optionally employs a step of correlating the presence or amount of a biomarker in a biological sample with the severity and/or type of nerve cell (or other biomarker-expressing cell) injury. The amount of biomarker(s) in the biological sample directly relates to severity of nerve tissue injury as a more severe injury damages a greater number of nerve cells which in turn causes a larger amount of biomarker(s) to accumulate in the biological sample (e.g., CSF; serum). Whether a nerve cell injury triggers an apoptotic and/or necrotic type of cell death can also be determined by examining illustratively the GBDPs present in the biological sample. Necrotic cell death preferentially activates calpain, whereas apoptotic cell death preferentially activates caspase-3. Because calpain and caspase-3 GBDPs can be distinguished, measurement of these markers indicates the type of cell damage in the subject. Also, the level of or kinetic extent of UCHL1, and or GFAP present in a biological sample may optionally distinguish mild injury from a more severe injury. In an illustrative example, severe MCAO (2 h) produces increased UCHL1 in both CSF and serum relative to mild challenge (30 min) while both produce UCHL1 levels in excess of uninjured subjects. Moreover, the persistence or kinetic extent of the markers in a biological sample is indicative of the severity of the injury with greater injury indicating increases persistence of illustratively GBDP, UCHL1, or SBDP in the subject that is measured by an inventive process in biological samples taken at several time points following injury.

The results of such a test can help a physician determine whether the administration a particular therapeutic such as calpain and/or caspase inhibitors or muscarinic cholinergic receptor antagonists or any immunomodulators might be of benefit to a patient. This method may be especially important in detecting age and gender difference in cell death mechanism.

It is appreciated that other reagents such as assay grade water, buffering agents, membranes, assay plates, secondary antibodies, salts, and other ancillary reagents are available from vendors known to those of skill in the art. Illustratively, assay plates are available from Corning, Inc. (Corning, N.Y.) and reagents are available from Sigma-Aldrich Co. (St. Louis, Mo.).

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Additional protocols such as PCR Protocols can be found in A Guide to Methods and Applications Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," Methods in Enzymology vol. 182, and other volumes in this series; Current Protocols in Protein Science, John Wiley and Sons, New York, N.Y.; and manufacturer's literature on use of protein purification products known to those of skill in the art.

Assays for neural cell biological activities are described, e.g., in Wouterlood (ed. 1995) Neuroscience Protocols modules 10, Elsevier; Methods in Neurosciences Academic Press; and Neuromethods Humana Press, Totowa, N.J.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to mammalian tissue, specifically, analyses of rat tissue, a person having ordinary skill in the art recognizes that similar techniques and other techniques known in the art readily translate the examples to other mammals such as humans. Reagents illustrated herein are commonly cross reactive between mammalian species or alternative reagents with similar properties are commercially available, and a person of ordinary skill in the art readily understands where such reagents may be obtained. Variations within the concepts of the invention are apparent to those skilled in the art.

EXAMPLE 1: Materials for Biomarker Analyses

Illustrative reagents used in performing the subject invention include Sodium bicarbonate (Sigma Cat #: C-3041), blocking buffer (Startingblock T20-TBS) (Pierce Cat#: 37543), Tris buffered saline with Tween 20 (TBST; Sigma Cat #: T-9039). Phosphate buffered saline (PBS; Sigma Cat #: P-3813); Tween 20 (Sigma Cat #: P5927); Ultra TMB ELISA (Pierce Cat #: 34028); and Nunc maxisorp ELISA plates (Fisher). Monoclonal and polyclonal GFAP and UCHL1 antibodies are made in-house or are obtained from Santa Cruz Biotechnology, Santa Cruz, Calif. Antibodies directed to α-II spectrin, GFAP, and breakdown products as well as to MAP2, MBP, neurofascin, IgG, and IgM are available from Santa Cruz Biotechnology, Santa Cruz, Calif.

The anti-tau antibody directed to full length tau is purchased from Santa Cruz Biotechnology, Santa Cruz, Calif. To generate antibodies specific to tau-BDPs, the synthetic peptide (Cys-$C_6$-SIDMVD$_{-COOH}$) (SEQ ID NO: 1) which is the sequence of the caspase-3 generated C-terminal tau breakdown product (tauBDP-45K) (Chung et al., 2001), and the second peptide ($_{NH2-}$KDRTGN-$C_6$-Cys) (SEQ ID NO: 2) representing the N-terminal of the calpain mediated TauBDP-35K are custom-made by peptide synthesis (California Peptide, Napa, Calif.). A $C_6$ linker and N-terminal cysteine are introduced for the subsequent coupling of the peptide to Keyhole Limpet Hemocyanin (KLH) protein using a sulfo-link crosslinking reagent (Pierce). After coupling efficiency determinations, peptides are dialyzed and concentrated. Rabbits are immunized with 2 mg of conjugated protein by injection. Serum samples are collected after three months and are affinity purified using the synthetic peptide against which they were raised coupled to sulfo-linked resins (Pierce). Affinity-purified antibody is then dialyzed against TBS (20 mM Tris-HCl, pH 7.4, 150 mM NaCl) and concentrated for storage in 50% glycerol at −20° C.

Labels for antibodies of numerous subtypes are available from Invitrogen, Corp., Carlsbad, Calif. Protein concentrations in biological samples are determined using bicinchoninic acid microprotein assays (Pierce Inc., Rockford, Ill., USA) with albumin standards. All other necessary reagents and materials are known to those of skill in the art and are readily ascertainable.

EXAMPLE 2: Biomarker Assay Development

Anti-biomarker specific rabbit polyclonal antibody and monoclonal antibodies as well as antigens are produced in the laboratory or purchased commercially. To determine reactivity specificity of the antibodies to detect a target biomarker a known quantity of isolated or partially isolated biomarker is analyzed or a tissue panel is probed by western blot. An indirect ELISA is used with the recombinant biomarker protein attached to the ELISA plate to determine optimal concentration of the antibodies used in the assay. Microplate wells are coated with rabbit polyclonal anti-human biomarker antibody. After determining the concentration of rabbit anti-human biomarker antibody for a maximum signal, the lower detection limit of the indirect ELISA for each antibody is determined. An appropriate diluted sample is incubated with a rabbit polyclonal antihuman biomarker antibody for 2 hours and then washed. Biotin labeled monoclonal anti-human biomarker antibody is then added and incubated with captured biomarker. After thorough wash, streptavidin horseradish peroxidase conjugate is added. After 1 hour incubation and the last washing step, the remaining conjugate is allowed to react with substrate of hydrogen peroxide tetramethyl benzadine. The reaction is stopped by addition of the acidic solution and absorbance of the resulting yellow reaction product is measured at 450 nanometers. The absorbance is proportional to the concentration of the biomarker. A standard curve is constructed by plotting absorbance values as a function of biomarker concentration using calibrator samples and concentrations of unknown samples are determined using the standard curve.

EXAMPLE 3: In Vivo Model of TBI

A controlled cortical impact (CCI) device is used to model TBI on rats as previously described (Pike et al, 1998). Adult male (280-300 g) Sprague-Dawley rats (Harlan: Indianapolis, Ind.) are anesthetized with 4% isoflurane in a carrier gas of 1:1 $O_2/N_2O$ (4 min.) and maintained in 2.5% isoflurane in the same carrier gas. Core body temperature is monitored continuously by a rectal thermistor probe and maintained at 37±1° C. by placing an adjustable temperature controlled heating pad beneath the rats. Animals are mounted in a stereotactic frame in a prone position and secured by ear and incisor bars. Following a midline cranial incision and reflection of the soft tissues, a unilateral (ipsilateral to site of impact) craniotomy (7 mm diameter) is performed adjacent to the central suture, midway between bregma and lambda. The dura mater is kept intact over the cortex. Brain trauma is produced by impacting the right (ipsilateral) cortex with a 5 mm diameter aluminum impactor tip (housed in a pneumatic cylinder) at a velocity of 3.5 m/s with a 1.6 mm compression and 150 ms dwell time. Sham-injured control animals are subjected to identical surgical procedures but do not receive the impact injury. Appropriate pre- and post-injury management is preformed to insure compliance with guidelines set forth by the University of Florida Institutional Animal Care and Use Committee and the National Institutes of Health guidelines detailed in the Guide for the Care and Use of Laboratory Animals. In addition, research is conducted in compliance with the Animal Welfare Act and other federal statutes and regulations relating to animals and experiments involving animals and adhered to principles stated in the "Guide for the Care and Use of Laboratory Animals, NRC Publication, 1996 edition."

EXAMPLE 4: Middle Cerebral Artery Occlusion (MCAO) Injury Model

Rats are incubated under isoflurane anesthesia (5% isoflurane via induction chamber followed by 2% isoflurane via nose cone), the right common carotid artery (CCA) of the rat is exposed at the external and internal carotid artery (ECA and ICA) bifurcation level with a midline neck incision. The ICA is followed rostrally to the pterygopalatine branch and the ECA is ligated and cut at its lingual and maxillary branches. A 3-0 nylon suture is then introduced into the ICA via an incision on the ECA stump (the suture's path was visually monitored through the vessel wall) and advanced through the carotid canal approximately 20 mm from the carotid bifurcation until it becomes lodged in the narrowing of the anterior cerebral artery blocking the origin of the middle cerebral artery. The skin incision is then closed and the endovascular suture left in place for 30 minutes or 2 hours. Afterwards the rat is briefly reanesthetized and the suture filament is retracted to allow reperfusion. For sham MCAO surgeries, the same procedure is followed, but the filament is advanced only 10 mm beyond the internal-external carotid bifurcation and is left in place until the rat is sacrificed. During all surgical procedures, animals are maintained at 37±1° C. by a homeothermic heating blanket (Harvard Apparatus, Holliston, Mass., U.S.A.). It is important to note that at the conclusion of each experiment, if the rat brains show pathologic evidence of subarachnoid hemorrhage upon necropsy they are excluded from the study. Appropriate pre- and post-injury management is preformed to insure compliance with all animal care and use guidelines.

EXAMPLE 5: Tissue and Sample Preparation

At the appropriate time points (2, 6, 24 hours and 2, 3, 5 days) after injury, animals are anesthetized and immediately sacrificed by decapitation. Brains are quickly removed, rinsed with ice cold PBS and halved. The right hemisphere (cerebrocortex around the impact area and hippocampus) is rapidly dissected, rinsed in ice cold PBS, snap-frozen in liquid nitrogen, and stored at −80° C. until used. For immunohistochemistry, brains are quick frozen in dry ice slurry, sectioned via cryostat (20 µm) onto SUPERFROST PLUS GOLD® (Fisher Scientific) slides, and then stored at −80° C. until used. For the left hemisphere, the same tissue as the right side is collected. For western blot analysis, the brain samples are pulverized with a small mortar and pestle set over dry ice to a fine powder. The pulverized brain tissue powder is then lysed for 90 min at 4° C. in a buffer of 50 mM Tris (pH 7.4), 5 mM EDTA, 1% (v/v) Triton X-100, 1 mM DTT, 1× protease inhibitor cocktail (Roche Biochemicals). The brain lysates are then centrifuged at 15,000×g for 5 min at 4° C. to clear and remove insoluble debris, snap-frozen, and stored at −80° C. until used.

For gel electrophoresis and electroblotting, cleared CSF samples (7 µl) are prepared for sodium dodecyl sulfate-polyacrylamide gel electrophoresis (SDS-PAGE) with a 2× loading buffer containing 0.25 M Tris (pH 6.8), 0.2 M DTT, 8% SDS, 0.02% bromophenol blue, and 20% glycerol in distilled $H_2O$. Twenty micrograms (20 µg) of protein per lane are routinely resolved by SDS-PAGE on 10-20% Tris/glycine gels (Invitrogen, Cat #EC61352) at 130 V for 2 hours. Following electrophoresis, separated proteins are laterally transferred to polyvinylidene fluoride (PVDF) membranes in a transfer buffer containing 39 mM glycine, 48 mM Tris-HCl (pH 8.3), and 5% methanol at a constant voltage of 20 V for 2 hours at ambient temperature in a semi-dry transfer unit (Bio-Rad). After electro-transfer, the membranes are blocked for 1 hour at ambient temperature in 5% non-fat milk in TBS and 0.05% Tween-2 (TBST) then are incubated with the primary monoclonal GFAP antibody in TBST with 5% non-fat milk at 1:2000 dilution as recommended by the manufacturer at 4° C. overnight. This is followed by three washes with TBST, a 2 hour incubation at ambient temperature with a biotinylated linked secondary antibody (Amersham, Cat #RPN1177v1), and a 30 min incubation with Streptavidin-conjugated alkaline phosphatase (BCIP/NBT reagent: KPL, Cat #50-81-08). Molecular weights of intact biomarker proteins are assessed using rainbow colored molecular weight standards (Amersham, Cat #RPN800V). Semi-quantitative evaluation of intact GFAP, UCHL1, or SBDP protein levels is performed via computer-assisted densitometric scanning (Epson XL3500 scanner) and image analysis with ImageJ software (NIH).

EXAMPLE 6: Breakdown Products as Biomarkers of Neuronal Injury

Figure 1A:
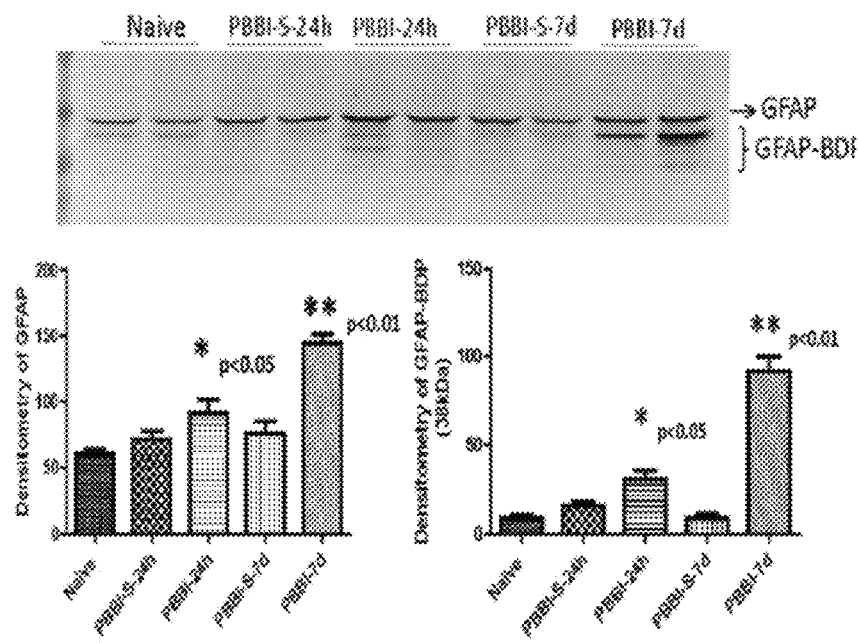
FIG. 1A and FIG. 1B are western blots for GFAP and GBDP in rat tissue following traumatic brain injury and quantification.
Figure 1B:
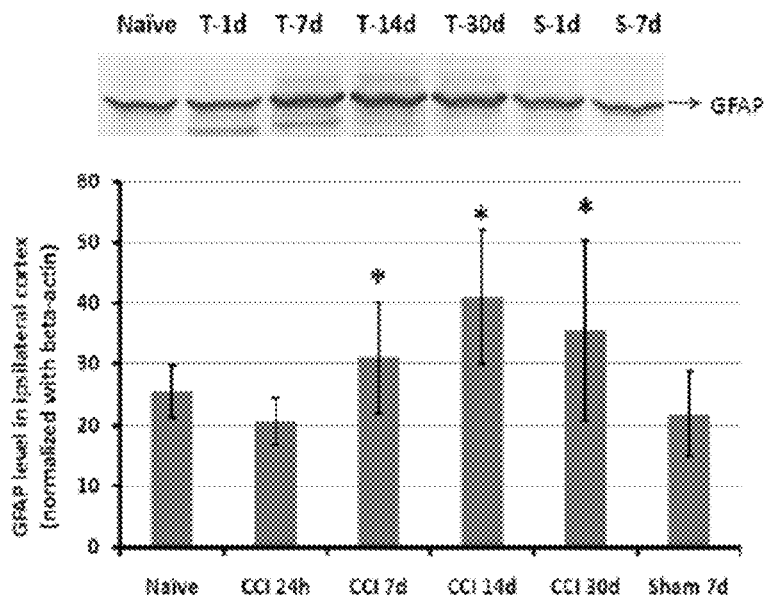
Figure 2:
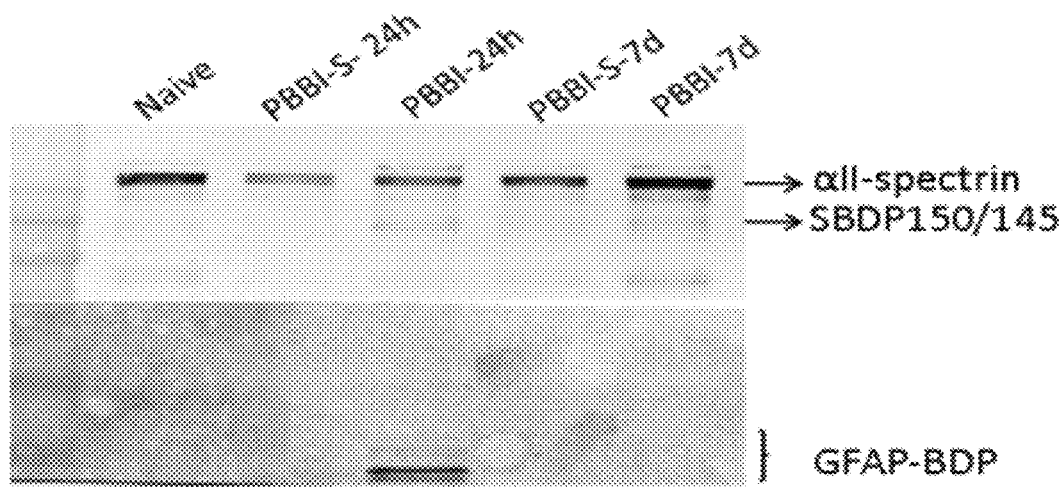
FIG. 2 are western blots of GFAP and GBDP in rat CSF following traumatic brain injury.

CSF is prepared as per Example 5 following CCI in rats as described in Example 3. Western blotting using anti-GFAP antibodies reveal an increase in GFAP with increasing time following CCI injury (FIG. 1A, B). Similarly, the levels of GFAP increase with time following CCI with statistically significant maximal levels at day 14 following injury (FIG. 1B). The levels of GFAP and GBDP in rat ipsilateral cortex are also measured and demonstrate increased levels relative to sham (S) treated animals (FIG. 2). These data demonstrate an increase in GFAP and GBDP in CSF and neuronal tissue following CCI similar to that of severe TBI.

Figure 3A:
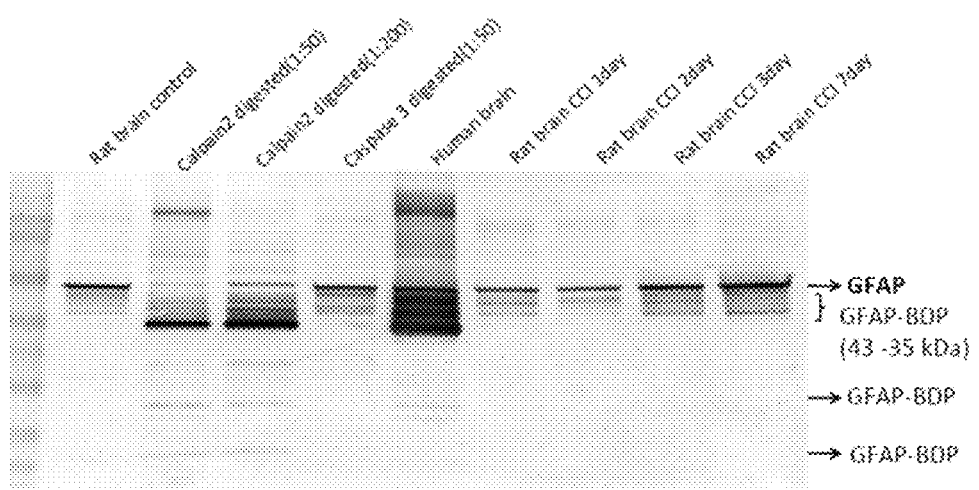
FIG. 3 are western blots of in vitro digested brain lysates compared to rat CCI samples and a digested human sample illustrating levels of GBDP (A) and SBDP (B)

The breakdown of GFAP in neurons is injury specific. Rat brain tissue lysates from sham treated animals of Example 3 as well as a human brain sample from a non-TBI cadaver are treated with two levels of calpain-2 and caspase-3 followed by western blotting using primary antibodies to either GFAP and GBDPs or SBDPs. FIG. 3 demonstrates that in vitro digestion of rat brain lysates with calpain-2 show overlapping GBDPs with digested human brain lysate. Caspase-3 cleavage of rat brain revealed similar GBDPs to CCI treated rats (FIG. 3A).

Figure 3B:

Similarly, the levels of SBDP 150/145 are increased in rat CSF following CCI at both 24 hours and 7 days following injury (FIG. 3B).

Lysates of mixed glial/neuron cultures are examined for the presence of GBDPs following various treatments. To obtain the cultures cerebrocortical cells are harvested from 1-day old Sprague-Dawley rat brains and plated on poly-L-lysine coated on 6-well culture plates (Erie Scientific, Portsmouth, N.H., USA) according to the method of Nath et al., J. Neurochem., 1998; 71:186-195 at a density of 4.36×105 cells/mL. Cultures are maintained in Dulbecco's modified Eagle's medium (DMEM) with 10% fetal bovine serum in a humidified incubator in an atmosphere of 10% $CO_2$ at 37° C. After 5 days in culture, the media are changed to DMEM with 5% horse serum. Subsequent media changes are performed three times a week. Experiments are performed on days 10 to 11 in vitro when astroglia had formed a confluent monolayer beneath morphologically mature neurons.

In addition to untreated controls, the following conditions are examined: methotrexate (MTX) (1 µM); apoptotic inducers staurosporine (STS) (0.5 µM; Sigma, St. Louis, Mo.) that activates calpain and caspase-3 for 24 hours (Zhang et al., 2009); the $Ca^{2+}$ chelator ethylene diamine tetra-acetic acid (EDTA) (5 mM; Sigma) for up to 24 hours as a caspase-dominated challenge (Waterhouse et al., 1996; Chiesa et al., 1998; Mizuno et al., 1998; McGinnis et al., 1999; Zhang et al., 2009). For pharmacologic intervention, cultures were pretreated one hour before the STS, EDTA or MTX challenge with the calpain inhibitor SNJ1945 (Senju Pharmaceuticals, Kobe, Japan) (Shirasaki et al., 2005; Oka et al. 2006; Koumura et al., 2008), or the pan-caspase inhibitor Z-VAD (OMe)-FMK (R & D, Minneapolis, Minn.).

Figure 4:
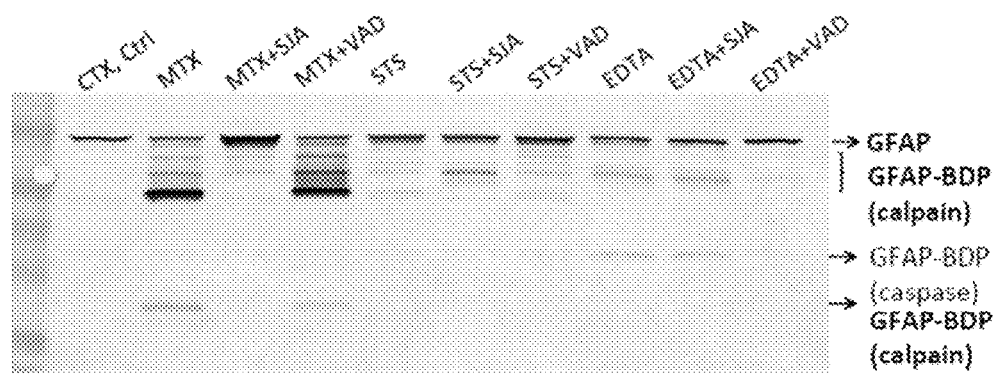
FIG. 4 illustrates differential proteolysis of GFAP to GBDP upon varying neurotoxic insult.

MTX treated cultured cells showed calpain specific cleavage of GFAP as illustrated by reduction in GBDPs using SJA treatment and the lack of inhibition by treatment with VAD (FIG. 4). In contrast, EDTA treatment produces caspase mediated GDBP formation as illustrated by no effect by SJA treatment and no GBDP with treatment by VAD. Treatment with the apoptosis inducer STS illustrated a balanced cleavage of GFAP by both calpain and caspase.

Figure 5:
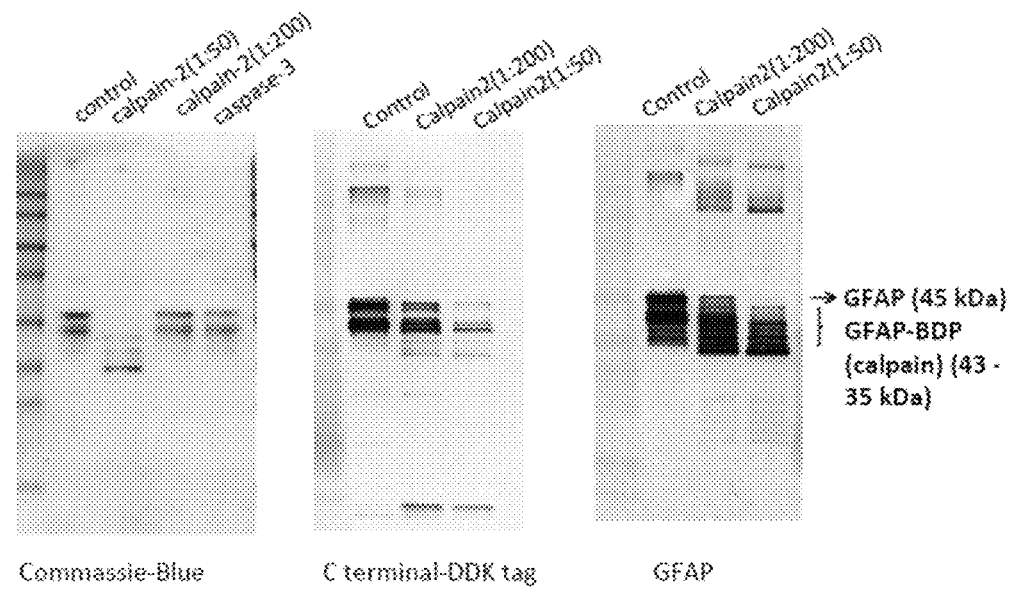
FIG. 5 illustrates calpain induced cleavages of recombinant human GFAP.

To identify the cleavage sites in GFAP mediated by calpains and caspases in neuronal cells, recombinant GFAP is subjected to cleavage with differing levels of calpain or caspase. FIG. 5 illustrates GFAP digestion as detected by Coomassie blue staining, detection of a C-terminal tag (DDK) associated with recombinant GFAP or by western blot with anti-GFAP antibody illustrates successful cleavage by both calpain and caspase. Excision of GBDP bands from Coomassie blue stained gels and subjecting the bands to N-terminal sequencing reveals cleavage by calpain 2 at Asn59 (GALN*$_{59}$AGFKETRASERAE) (SEQ ID NO: 3) to produce a GBDP with new C-terminus VDFSLAGALN-COOH (SEQ ID NO: 139) and a GBDP with new N-terminus NH$_2$-AGFKETRASE (SEQ ID NO: 140), and Thr383 (TIPVQT*$_{383}$FSNLQIRET) (SEQ ID NO: 4) producing a GBDP with new C-terminus ENRITIPVQT-COOH (SEQ ID NO: 141) and a GBDP with new N-terminus NH$_2$-FSNLQIRETS (SEQ ID NO: 142), overall producing multiple GBDPs between 49 and 38 kDa in recombinant human GFAP.

Breakdown products of Tau in rat hippocampus 48 hours following CCI are identified in U.S. Pat. No. 7,456,027, the contents of which are incorporated herein by reference. It was shown that following experimental TBI by CCI injury that rat Tau is cleaved to produce TBDPs of molecular weight 40-55 kDa, 36 kDa, 26 kDa, 18, kDa, and 13 kDa. The cleavage sites and their relevance to specific types of neuronal injury were unknown. The cleavage sites in Tau are identified by in vitro digestion of recombinant rat tau using calpain 2 or calpain 1. Following digestion, cleavage fragments are separated by SDS-PAGE, stained with Coomassie blue and bands excised and subjected to N-terminal sequencing. The sequence results are compared to the known sequence of rat tau. Full length rat Tau with calpain and caspase cleavage sites are illustrated in Table 6

TABLE 6

(SEQ ID NO: 5) The * represents a cleavage site; the bold lettering represents an epitope used to raise a TBDP specific antibody.
Rat Tau

```
  1    MAEPRQEFDT  MEDQAGDYTIM  LQDQEGDMDHGLK  *  ESPPQPPADD  GSEEPGS  ETSDAKSTPT

61    AEDVTAPLVE  ERAPDKQATA  QSHTEIPEGT  TAEEAGIGDT  PNMEDQAAG  HVTQARVAGVS*

121    KDRTGNDEK  KAKGADGKTGA  KIATPRGAAT  PGQKSTSNAT  RIPAKTTPSP  KTPPGSGEPP

181    KSGERSGYSS  PGSPGTPGSR  SRTPSLPTP  PTREPKKVAVV  *  RTPPKSPSAS  KSRLQTAPVP

241    MPDLKNVRSK  IGSTENLKHQ  PGGGKVQIIN  KKLDLSNVQS  KCGSKDNIKH  VPGGGSVQIV

301    YKPVDLSKVT  SKCGSLGNIH  HKPGGGQVEV  KSEKLDFKDR  VQSKIGSLDN  ITHVPGGGNK

361    KIETHKLTFR  *  ENAKAKTDHG  AEIVYKSPVV  SGDTSPRHLSNV  SSTGSIDMVD  *  SPQLATLA

421    DEVSASLAKQ  GL
```

Calpain cleaves rat tau at Lys43 (LK*$_{43}$ESPPQPPADD (SEQ ID NO: 6)) producing a TBDP with new C-terminus QEGDMDHGLK-COOH (SEQ ID NO: 115) and a TBDP with new N-terminus NH$_2$-QEGDMDHGLK (SEQ ID NO: 116); Ser120 (AGHVTQARMVS*$_{120}$KDRTGNDEK (SEQ ID NO: 7) producing a TBDP with new C-terminus VTQARVAGVS-COOH (SEQ ID NO: 117) and a TBDP with new N-terminus NH$_2$-KDRTGNDEKK (SEQ ID NO: 118), Val220 (PTREPKKVAVV*$_{220}$RTPPKSPSAS (SEQ ID NO: 8)) producing a TBDP with new C-terminus TREPKKVAVV-COOH (SEQ ID NO: 119) and a TBDP with new N-terminus NH$_2$-RTPPKSPSAS (SEQ ID NO: 120); and Arg370 (KIETHKLTFR*$_{370}$ENAKAKTDHGAEI (SEQ ID NO: 9)) (FIG. 5) producing a TBDP with new C-terminus KIETHKLTFR-COOH (SEQ ID NO: 121) and an TBDP with new N-terminus NH$_2$-ENAKAKTDHG (SEQ ID NO: 122). Caspase-3 cleaves rat Tau at Asp412 (SSTGSIDMVD*$_{412}$SPQLATLA (SEQ ID NO: 10)) to produce a TBDP with new C-terminus SSTGSIDMVD-COOH (SEQ ID NO: 123) and a TBDP with new N-terminus NH$_2$-SPQLATLADE (SEQ ID NO: 124).

Human Tau is cleaved by calpain and caspase at similar locations. Table 7 illustrates the cleavage locations in human tau.

TABLE 7

(SEQ ID NO: 11) The * represents a cleavage site; the bold lettering represents an epitope used to raise a TBDP specific antibody.
Human Tau

```
  1    MAEPRQEFEV  MEDHAGTYGLGKRKD*QGGYTMHQD  QEDGTDAGLK  *  ESPLQTPTED  GSEEPG

61    SETSDAKSTP  TAEDVTAPLV  DEGAPGKQAA  AQPHTEIPEG  TTAEEAGIGD  TPSLEDEAAG

121    HVTQARMVS  *  KSKDGTGSDDK  KAKGADGKTK  IATPRG  *  AAPP  GQKGQANATR  IPAKTPPAPK
```

TABLE 7-continued (SEQ ID NO: 11) The * represents a cleavage site; the bold lettering
represents an epitope used to raise a TBDP specific antibody.
Human Tau

```
181    TPPSSGEPPK SGDRSGYSSP GSPGTPGSRS RTPSLPTP PTREPKKVAVV * RTPPKSPSSAK

241    SRLQTAPVPM PDLKNVKSKI GSTENLKHQP GGGKVQIINK KLDLSNVQSK CGSKDNIKHV

301    PGGGSVQIVY KPVDLSKVTS KCGSLGNIHH KPGGGQVEVK SEKLDFKDRV QSKIGSLDNI

361    THVPGGGNKK IETHKLTFR * E NAKAKTDHGA EIVYKSPVVS GDTSPRHLSNV SSTGSIDMVD*

422    SPQLATLADEVSASLAKQGL
```

Figure 6:
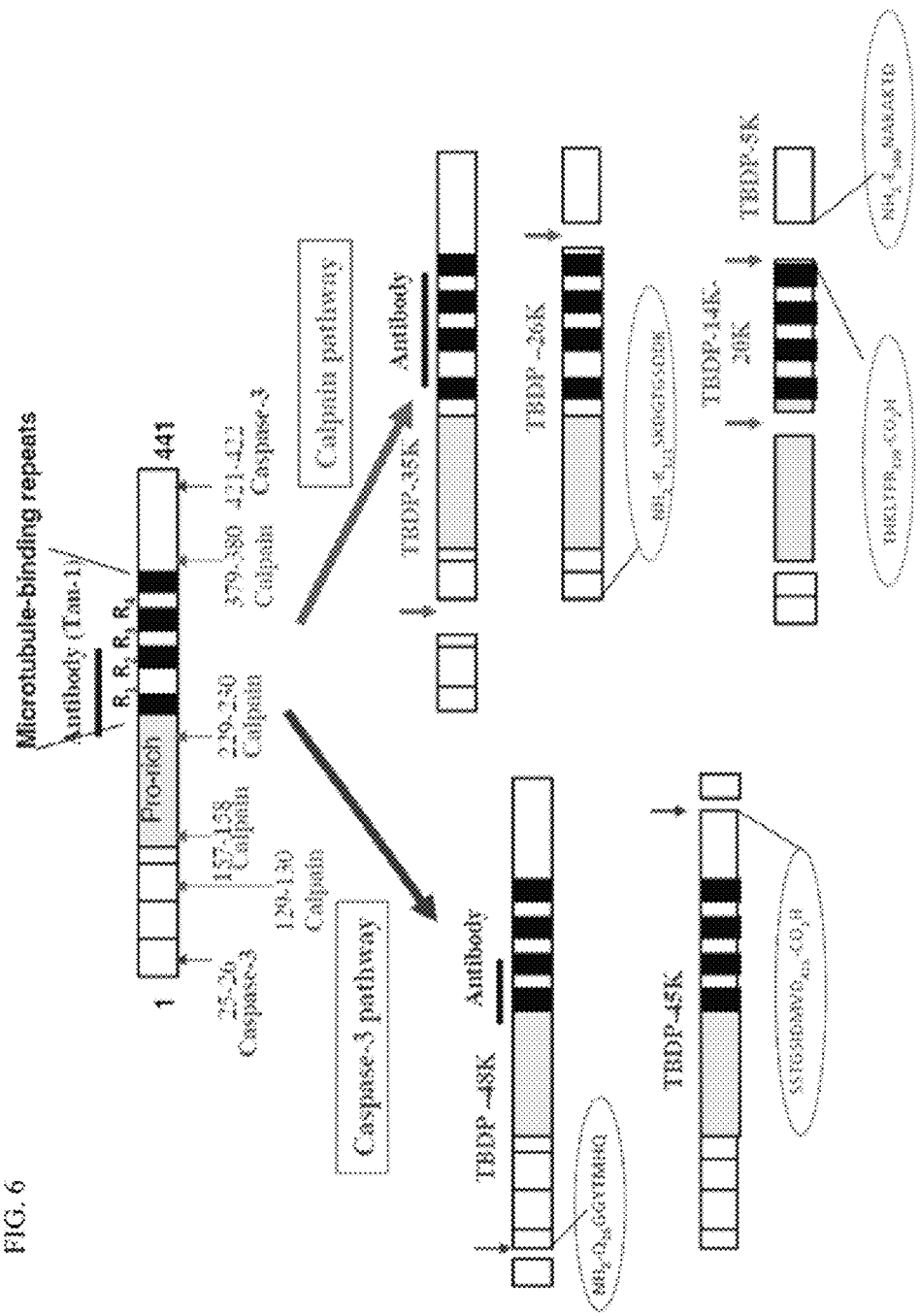
FIG. 6 is a schematic of Tau cleavage in neurons to produce TBDPs.

Human TBDPs are produced from Human Tau by calpain cleavage at Ser129 (AGHVTQARMVS$_{129}$KSKDGTGSDD (SEQ ID NO: 12)) to produce a TBDP with new C-terminus GHVTQARMVS-COOH (SEQ ID NO: 125) and a TBDP with new N-terminus NH$_2$-KSKDGTGSDD (SEQ ID NO: 126), Val229 (PTREPKKVAVV*$_{229}$RTPPKSPSSA (SEQ ID NO: 13)) to produce a TBDP with new C-terminus TREPKKVAVV-COOH (SEQ ID NO: 127) and a TBDP with new N-terminus NH$_2$-RTPPKSPSSA (SEQ ID NO: 128), Gly157 (GKTKIATPRG*$_{157}$AAPPGQKGQANATRITA (SEQ ID NO: 14)) to produce a TBDP with new C-terminus GKTKIATPRG-COOH (SEQ ID NO: 129) and a TBDP with new N-terminus NH$_2$-AAPPGQKGQA (SEQ ID NO: 130), Lys44 (LK*$_{44}$ESPLQTPTED (SEQ ID NO: 15)) to produce a TBDP with new C-terminus QEGDTDAGLK-COOH (SEQ ID NO: 131) and a TBDP with new N-terminus NH$_2$-ESPLQTPTED (SEQ ID NO: 132), and Arg379 (KIETHKLTFR*$_{379}$ENAKAKTDHGAEI (SEQ ID NO: 16)) to produce a TBDP with new C-terminus KIETHKLTFR-COOH (SEQ ID NO: 133), and a TBDP with new N-terminus NH2-ENAKAKTDHG (SEQ ID NO: 134). Caspase cleavage sites in human Tau are Asp25 (GDRKD*$_{25}$QGGYTMHQD (SEQ ID NO: 17)) to produce a TBDP with new C-terminus GTYGLGDRKD-COOH (SEQ ID NO: 135) and a TBDP with new N-terminus NH2-QGGYTMHQDQ (SEQ ID NO: 136), and Asp421 (SSTGSIDMVD*$_{421}$SPQLATLA (SEQ ID NO: 18)) to produce a TBDP with new C-terminus SSTGSIDMVD-COOH (SEQ ID NO: 137) and a TBDP with new N-terminus NH$_2$-SPQLATLADE (SEQ ID NO: 138). The overall neuronal injury cleavage pathways of human Tau are illustrated in FIG. 6.

Antibodies are raised to TAUBDP-45K (caspase) and TAUBDP-35K (calpain). A synthetic peptide (Cys-C$_6$-SIDMVD) (SEQ ID NO: 1) based on Tau C-terminal of tauBDP-45K generated by caspase-3 (Chung et al., 2001) and another peptide (KDRTGNDEK-C$_6$-Cys) (SEQ ID NO: 19) based on the new N-terminal of the calpain mediated TauBDP-35K are custom-made (California Peptide, Napa, Calif.). Other exemplary epitopes for antibodies specific for TBDPs are listed in Table 8.

TABLE 8

```
Tau Fragment-specific peptide epitopes
Human, rat: SSTGSIDMVD-COOH             (SEQ ID NO: 20)
Human, rat: NH2-SPQLATLA                (SEQ ID NO: 21)
Rat: AG HVTQARVAGVS-COOH                (SEQ ID NO: 22)
Rat: NH2-KDRTGNDEK                      (SEQ ID NO: 23)
Human, rat: PTREPKKVAVV-COOH            (SEQ ID NO: 24)
Human, rat: NH2-RTPPKSPSAS              (SEQ ID NO: 25)
Human, rat, mouse: KIETHKLTFR-COOH      (SEQ ID NO: 26)
Human, rat, mouse: NH2-ENAKAKTDHGAEI    (SEQ ID NO: 27)
Rat: QEGDMDHGLK-COOH                    (SEQ ID NO: 28)
Rat: NH2-ESPPQPPADD                     (SEQ ID NO: 29)
Human: QEGDTDAGLK-COOH                  (SEQ ID NO: 30)
Human: NH2-ESPLQTPTED                   (SEQ ID NO: 31)
Human: GTYG LG DRKD-COOH                (SEQ ID NO: 32)
Human: NH2-QGGYT MHQD                   (SEQ ID NO: 33)
Human: GKTKIATPRG-COOH                  (SEQ ID NO: 34)
Human: NH2-AAPPGQKGQA                   (SEQ ID NO: 35)
Human: AGHVTQARMVS-COOH                 (SEQ ID NO: 36)
Human: NH2-KSKDGTGSDD                   (SEQ ID NO: 37)

Calpain cleavage site peptide epitopes
Pro-calpain-2 (human, rat): SHERAIK     (SEQ ID NO: 38)

Activated calpain-1 (human, rat):       (SEQ ID NO: 39)
NH2-LGRHENA peptide
```

A C$_6$ linker and N-terminal cysteine are introduced for the subsequent coupling of the peptide to Keyhole Limpet Hemocyanin (KLH) protein using a sulfo-link crosslinking reagent (Pierce). After coupling efficiency determinations, peptides are dialyzed, concentrated, and 2 mg of conjugated protein is used for multiple antigen injections into two rabbits. After 3 months, collected serum samples from the rabbits are subjected to affinity purification using the same synthetic peptide-coupled to sulfo-linked resins (Pierce). Affinity-purified antibody is dialyzed against TBS (20 mM Tris-HCl, pH 7.4, 150 mM NaCl), before it is concentrated and stored in 50% glycerol at −20° C.

Additional antibodies to specific cleavage products are also produced. Antigens used include: Cys-eAhx-SSTGSID-MVD-OH (SEQ ID NO: 40) to produce an antibody specific to TBDP-45K (caspase) in human and rat; Cys-C6-PTREP-KKVAVV (SEQ ID NO: 41) to produce an antibody specific to human and rat TBDP-14K-20K (calpain); NH2-KSKDGTGSDD-C6-Cys (SEQ ID NO: 42) to human TBDP-35K (calpain); ESPLQTPTED-C6 (SEQ ID NO: 43) to human TBDP-14k; and Cs-Cy6-HVTQARMVS (SEQ ID NO: 44) to human TBDP-10k C-terminal. Other antibodies presented in U.S. Applications Publication No: 2005/0260697, incorporated herein by reference, are also produced.

Rat tau protein (100 ng) is digested with either calpain-2 or caspase-3. The resulting fragments are separated by SDS-PAGE and probed by western blot with the raised antibodies. Both calpain-1 and -2 digest tau into several immunoreactive fragments (42 kDa, 35 kDa and 15 kDa), while caspase-3 digestion only produces limited fragment doublet of 48 kDa/45/kDa (FIG. 7A-C). Probing with TauBDP-35K (Calpain) and TauBDP-45K (caspase) antibodies confirms the fragment-specificity of the antibodies and no cross-reactivity with intact protein or other fragments. (FIG. 7B-C).

Figure 8A:
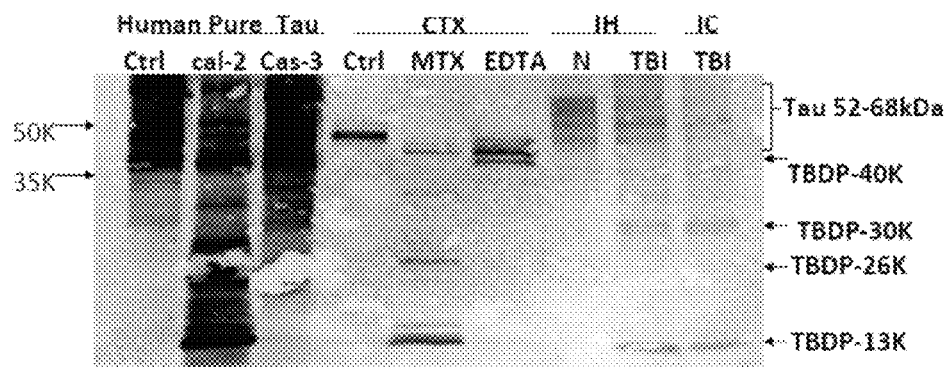
FIG. 8A illustrates breakdown products of human and rat Tau as probed by total Tau antibody.
Figure 8B:
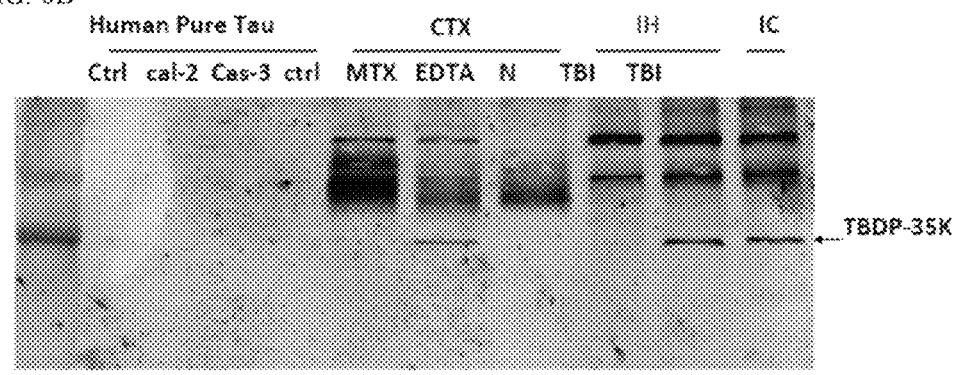
FIG. 8B illustrates breakdown products of human and rat Tau as probed by rat TBDP-35K antibody.
Figure 8C:
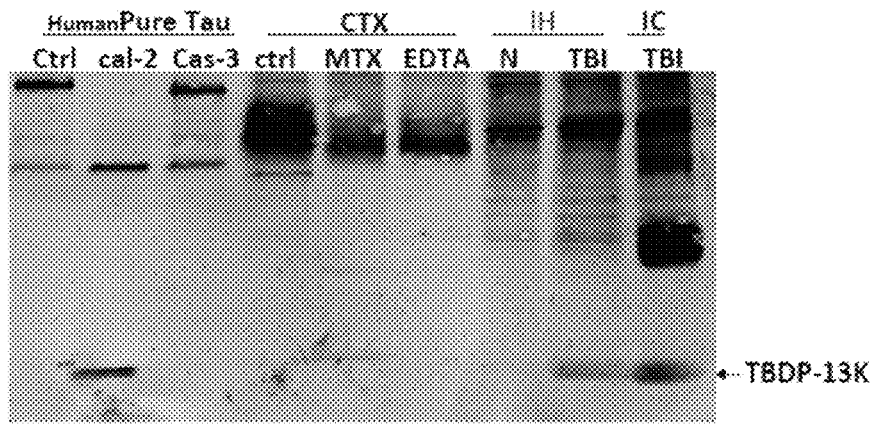
FIG. 8C illustrates breakdown products of human and rat Tau as probed by rat TBDP-13K specific antibody.

The TBDP antibodies are analyzed for cross reactivity with human Tau BDPs. Purified human Tau is left either untreated, calpain-2 treated, or caspase-3 treated to produce TBDPs. These are compared to TBDPs produced by MTX, or EDTA treated rat cerebrocortical culture cells (CTX) as described above as well as to naïve or TBI ipsilateral hippocampus (IH) or ipsilateral cortex (IC) models. The resulting fragments are separated by SDS-PAGE and probed with anti-total tau monoclonal antibody as illustrated in FIG. 8A. Treatment of human tau with calpain or caspase produce numerous breakdown products. MTX treated CTX cells reveals calpain specific cleavages of Tau and EDTA treated CTX cells shows caspase specific cleavages of Tau. The protease mediated cleavage of Tau following TBI is illustrated in both IH and IC TBI models. (FIG. 8A) The anti-TBDP-35K specific antibody shows no cross reactivity to human Tau (FIG. 8B).

Figure 9A:
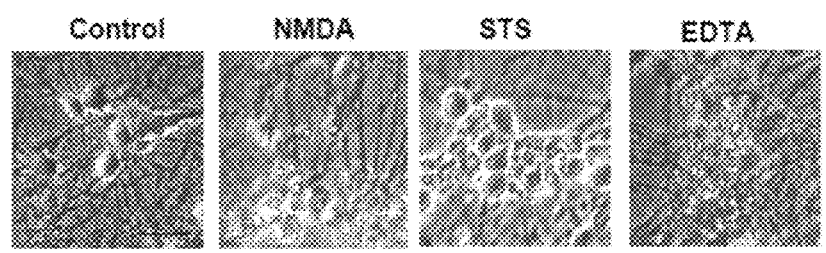
FIG. 9A and FIG. 9B illustrates rat cerebrocortical cultures challenged by various agents by phase contrast microscopy or assessed by using propidium iodine labeling of nuclei at 24 h for necrosis, and Hoechst 33342 stained condensed nuclear DNA as evidence for % apoptosis.
Figure 9B:
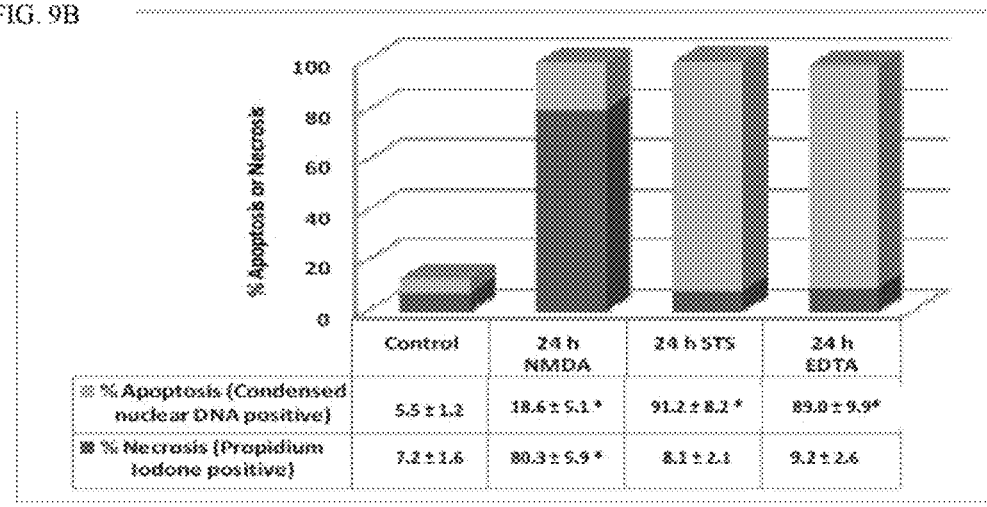

The TBDP specific antibodies are used to probe rat cerebrocortical cultures that are either naïve or subjected to treatment with: an excitotoxic challenge NMDA—(Nath et al., 1998); the apoptotic inducer staurosporine (STS) (0.5 µM) that activates calpain and caspase-3 for 24 hours (Zhang et al., 2009); or the $Ca^{2+}$ chelator and apoptotic inducer ethylene diamine tetra-acetic acid (EDTA) as a caspase-dominated challenge (Waterhouse et al., 1996; Chiesa et al., 1998; Mizuno et al., 1998; McGinnis et al., 1999; Zhang et al., 2009). NMDA, EDTA and STS treatments each produce extensive neurodegeneration in vitro. NMDA induces a mixed necrosis/apoptosis phenotype, while both STS and EDTA produce a robust apoptosis phenotype (FIG. 9A-B).

Figure 10:
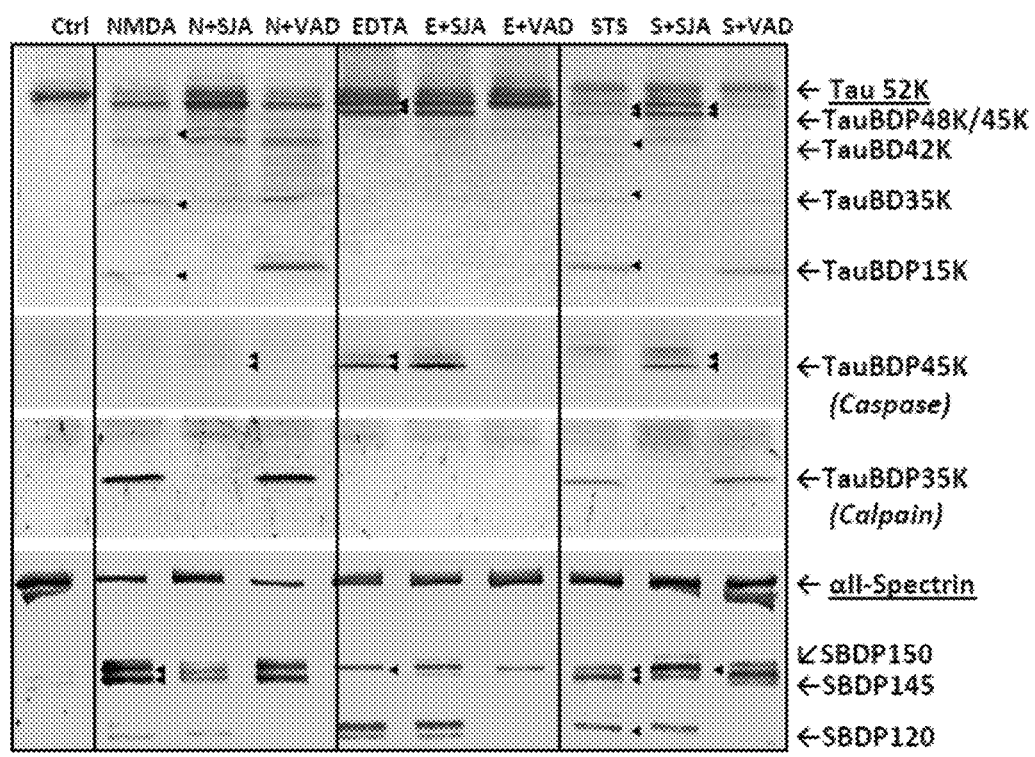
FIG. 10 illustrates rat cerebrocortical cultures challenged by various agents and probed for Tau and TBDPs.

Rat cerebrocortical culture lysates are probed with either total-Tau antibody or fragment specific antibodies. With NMDA treatment, Tau is significantly degraded into multiple fragments (42K, 35K, and 15K) including a dominant signal of calpain-mediated TauBDP-35K with minimal caspase-mediated Tau-BDP45K (FIG. 10). The caspase inhibitor (Z-VAD; 20 µM) produces no significant changes of Tau breakdown pattern. The inhibitor (SNJ-1945; 20 µM) significantly reduces the lower molecular weight fragment, including complete blockade of the calpain-mediated TauBDP-35K, although some high molecular weight fragments (425-48K) persist. Interestingly, when a blot was probed with the anti-caspase-mediated Tau-BDP45K antibody, the TauBDP-45/48K are detected in the calpain inhibitor-NMDA co-treatment lane. NMDA treatment yields prominent calpain-mediated SBDP150/SBDP145, with minor bands of caspase-3-mediated SBDP120. These fragments are strongly inhibited with their respective protease inhibitors (SNJ, Z-VAD). Taken together, these data suggest that in NMDA paradigm, calpain is the dominant pathway in tau fragmentation with a more minor contribution of caspase.

Using the apoptosis inducer EDTA, Tau is truncated only to Tau-BDP48K/45K, as confirmed by total tau blot and caspase-mediated anti-Tau-BDP45K blot (FIG. 10). Both fragments are caspase inhibitor (Z-VAD)-sensitive but insensitive to calpain inhibitor (SNJ-1945). Thus, EDTA challenge produces a straight caspase-dominant tau fragmentation condition. αII-Spectrin breakdown pattern from EDTA challenge confirms the presence of caspase-mediated SBDP120, but not calpain generated fragment SBDP145.

Staurosporine treatment illustrates a balance of higher molecular weight (45-48K) and low molecular weight (35K, 15K) tau-BDPs (FIG. 10). The 48/45K fragments are caspase-mediated as confirmed by the tau-45K fragment-specific antibody blot as well as its sensitivity to caspase inhibitor (Z-VAD). Similarly, the involvement of calpain is confirmed by the TauBDP-35K-specific antibody and its sensitivity to calpain inhibitor SNJ-1945. Importantly, the presence of calpain inhibitor strongly elevated the Tau-DBP-48k/45K by both total tau blot and anti-Tau-48/45K blot suggesting the dual involvement of both calpain and caspase. This is also consistent with αII-spectrin breakdown pattern. STS treatment produces a neurodegenerative paradigm where there is a dual and balanced contribution of both calpain and caspase in tau fragmentation.

TBDPs are produced by CCI injury in rats. Cortical and hippocampal tissue samples obtained following CCI injury as in Example 3 are lysed and the proteins are separated by SDS-PAGE followed by western blotting to identify the presence of specific TBDPs. In rat cortex TBDP-15K rapidly increases with early presentation at 2 hours and recurring maximal levels by 6 hours post-CCI (FIG. 11A, B). The levels then drop after 48 hours post-injury. TBDP-25K shows more gradual increases reaching a maximal level at 48 hours (FIG. 11A, B). Other Tau-BDPs are also observed. The numerous bands observed in both the sham treated as well as the post-CCI represent the numerous phosphorylation states and isoforms of the Tau protein. In the contralateral cortex, no tau proteolysis is observed in all three groups even when tau immunoblots are intentionally over-developed (data not shown). In rat hippocampus TBDP-15K is present at 2 hours post injury with a maximal level observed at 24 hours (FIG. 11C, D). Similar results are observed for TBDP-35K (FIG. 11C, D). Overall, the calpain mediated tau protein fragmentation pattern in vitro (TauBDP-35K, 25K, and 15K) (FIG. 7A-C) matches well with in vivo tau proteolysis after TBI (FIG. 11A-D). Since the controlled cortical impact device targets the cortex, greater focal injury occurs in the ipsilateral cortex tissue than in the hippocampal tissue, which is impacted indirectly by contusive force. As a result, there is more extensive tau proteolysis in the cortex than in the hippocampus.

The same samples are probed using the TBDP specific antibodies. FIG. 12A illustrates specific calpain activity producing TBDP-35K in rat cortex and no caspase mediated cleavages in the rat cortex following CCI. Similar results are observed in the rat hippocampus (FIG. 12B). Thus, CCI induced neurodegeneration is accompanied by the formation and accumulation of calpain-mediated TBDPs with only minor contributions to caspase-generated Tau fragments in the injured cortex.

The calpain-1 and calpain-2 temporal activation profiles of tauBDP-35K are examined using anti-activated calpain-1 new-N-terminal (anti-LGRHENA) (SEQ ID NO: 39) antibody, or pro-calpain-2N-terminal (anti-SHERAIK) (SEQ ID NO: 38) antibody. FIG. 13 illustrates activation of both calpain-1 (FIG. 13A) and calpain-2 (FIG. 13B) in injured cortex. Calpain-1 has an early peak on day 2 and 3 and subsided afterward (FIG. 13A) while calpain-2 also peaked on day 2 but was sustained to 3 and 5 days (FIG. 13B). The calpain-1 activation matches very well with the appearance of calpain specific TBDP-35K.

The calpain mediated cleavage of Tau is further demonstrated by its inhibition using the calpain inhibitor SNJ-1945 which is administered (100 mg/kg, i.v. bolus) immediately following CCI. Probing of the cortical tissue is subjected to immunoblotting with the TBDP-35K specific antibody. The increase in TBDP-35K is suppressed by SNJ-1945 (FIG. 14). Thus, calpain-1 acts as a major Tau cleaving protease following TBI.

EXAMPLE 7: Severe Human Traumatic Brain Injury Study

A study included 46 human subjects suffering severe traumatic brain injury. Each of these subjects is characterized by being over age 18, having a GCS of less than or equal to 8 and required ventriculostomy and neuromonitoring as part of routine care. A control group A, synonymously detailed as CSF controls, included 10 individuals also being over the age of 18 or older and no injuries. Samples are obtained during spinal anesthesia for routine surgical procedures or access to CSF associated with treatment of hydrocephalus or meningitis. A control group B, synonymously described as normal controls, totaled 64 individuals, each age 18 or older and experiencing multiple injuries without brain injury. Further details with respect to the demographics of the study are provided in Table 9.

TABLE 9

Subject Demographics for Severe Traumatic Brain Injury Study

|   |   | TBI | CSF Controls | Normal Controls |
|---|---|---|---|---|
|   | Number | 46 | 10 | 64 |
|   | Males | 34 (73.9%) | 29 (65.9%) | 26 (40.6%) |
|   | Females | 12 (26.1%) | 15 (34.1%) | 38 (59.4% |
| Age: | Average | 50.2 | 58.2 1, 2 | 30.09 2, 3 |
|   | Std Dev | 19.54 | 20.52 | 15.42 |
|   | Minimum | 19 | 23 | 18 |
|   | Maximum | 88 | 82 | 74 |
| Race: | Caucasian |   |   |   |
|   | Black | 45 | 38 (86.4%) | 52 (81.2%) |
|   | Asian | 1 | 6 (13.6) | 4 (6.3%) |
|   | Other |   |   | 7 (10.9%) |
|   |   |   |   | 1 (1.6%) |
| GCS in Emergency Department |   |   |   |   |
|   | Average | 5.3 |   |   |
|   | Std Dev | 1.9 |   |   |

The level of biomarkers found in the first available CSF samples for a first and second patient (FIGS. 15A and B) illustrate elevated GFAP and GBDP at emergency room admission for a first patient (FIG. 15A). Similarly, a second patient who had CSF drawn within 6 hours following TBI revealed the presence of elevated levels of GFAP and GBDP at this time point (FIG. 15B). The second patient also demonstrated detectable but lower levels of GFAP and GBDP at 18 hours following injury. The levels of SBDP 150/145 and SBDP 120 are also elevated in CSF of the first patient at emergency room admission with relatively lower levels at later time points (FIG. 15A).

EXAMPLE 8

Identification of autoantibodies as biomarkers of TBI. Following severe TBI autoantibodies to neuronal proteins are produced and detectable in the blood of subjects. Brain lysate from a human TBI subject is obtained post-mortem and solubilized with lysis buffer containing 20 mM Tris-HCl, pH 7.4, 150 mM NaCl, 5 mM EDTA, 5 mM EGTA, 1% Triton X-100, 1 mM NaF, 1 mM Na3VO4, and a protease inhibitor cocktail tablet (Roche, Indianapolis, Ind.). Lysates are separated by SDS-PAGE and subsequently stained for total protein (FIG. 16A) and transferred onto a Polyvinylidene fluoride (PVDF) membrane (Bio-Rad Laboratories) for probing. The blots are probed using serum obtained from a human control donor (FIG. 16B) or from a human obtained 10 days post TBI (FIG. 16C) and autoantibodies are detected using anti-IgG/IgM. Several intense bands are observed in the serum from the post-TBI subject indicating the presence of serum autoantibodies.

Human serum contains autoantibodies are observed at increasing levels following TBI. Serum from five individual human control and TBI subjects are probed for the presence of autoantibodies. Samples of solubilized human post-TBI brain lysate as described above are separated by SDS-PAGE and transferred to PVDF membranes by the iblot method. The blot is probed with either serum from normal control human subjects or from five TBI subjects where samples are obtained either at 72 hours post TBI or 30 days post-TBI. Following several washes with TBST, the PVDF membranes are removed from the multiscreen apparatus and washed three more times, then finally incubated with a AP-conjugated goat anti-human IgG+IgM or AP-conjugated donkey anti-human IgG diluted 1:10,000 for one hour followed by washing with TBST. Positive signals are visualized using 5-bromo-4-chloro-3-indolylphosphate/nitroblue tetrazolium (BCIP/NBT) phosphatase substrate (Kirkegaard & Perry Laboratories, Gaithersburg, Md., USA). FIG. 17 illustrates the presence of autoantibodies to several human brain proteins that are present following TBI. The amount of autoantibody is increased from day 72 to day 30 as illustrated by enhanced signal at the later timepoint.

The level of autoantibody increases with time following TBI. The serum from a single human subject obtained at admission and up to 30 days following TBI is used to probe human brain lysates loaded at equal concentrations in each lane of a gel and transferred to PVDF. The autoantigen is an IgG as demonstrated by detection using an anti-IgG secondary antibody (FIG. 18A). The rate at which autoantibody is produced is surprisingly fast with detectable levels appearing at day 5 and increasing out to day 30 (FIG. 18A). Confirmation that the autoantibodies are IgG specific is illustrated in FIG. 18B where blots are probed with secondary antibodies to particular immunoglobulin species.

The autoantibodies are directed to brain specific antigens. Lysates (30 µg of protein) from human brain, heart, kidney, lung, spleen, intestine, skin, muscle, and testes are separated by SDS-PAGE, transferred to PVDF and detected using western blot by probing with the serum of a human TBI subject at a dilution of 1:100. Any bound autoantibodies are detected by AP conjugated goat anti-human IgG/IgM at a dilution of 1:10,000. FIG. 19 illustrates that autoantibodies from TBI subjects recognize autoantigens migrating between 38 and 52 kDa from brain alone.

The autoantibodies are directed to a breakdown product as the result of calpain digestion. Naïve rat brain lysates are loaded onto a gel and probed with the serum from a human TBI subject. In the absence of calpain cleavage products, no antigen recognition is observed (data not shown). However, calpain digested rat brain lysate loaded at identical concentrations is recognized by human TBI patient autoantibody detectable beginning from day 5 (lane 12) and increasing to day 10 (lane 17) following TBI (FIG. 20).

To identify which antigens were recognized by autoantibodies in human serum post-TBI, purified GFAP, neurofacein, and MBP were loaded onto gels, separated by SDS-PAGE, transferred to PVDF and probed with serum from a TBI human subject obtained 10 days after injury followed by detection using an anti-IgG antibody. GFAP, neurofascin, and MBP are each detected as autoantigens recognized by autoantibodies generated in human serum following TBI (FIG. 21).

GFAP is confirmed as recognized by autoantibodies in the serum from a human subject obtained 10 days following TBI. Post-mortem human brain lysates are subjected to ion exchange chromatography and eluate fractions are loaded onto a gel and separated. Total protein in each fraction is stained with Coomassie blue (FIG. 22A). Identical fractions are separated and transferred to PVDF for detection of autoantigens by probing with serum from a human TBI subject (FIG. 22B). The overlapping bands on the stained gel are excised and subjected to sequence analysis. Sequence analyses reveal that the autoantibodies present in human serum post-TBI recognize GFAP.

Antigen competition experiments confirm that autoantibodies present in human serum post-TBI recognize GFAP and Tau. Human brain lysates (300 µg) are probed with serum from three human TBI subjects alone or pre-incubated with of varying concentrations of GFAP (2.6 µg; 10 µg (Banyan Biomarkers)) or Tau (2.6 µg or 10 µg (Cytoskeleton Co.)). The presence of 2.5 µg of GFAP reduces the ability of GFAP specific autoantibodies to recognize GFAP present in brain lysates (FIG. 23A). The signal is further reduced by 10 µg GFAP. Similarly, pre-incubation of serum with 10 µg Tau protein shows less antigen recognition than 2.6 µg Tau indicating the presence of Tau specific autoantibodies in human post-TBI serum (FIG. 23B).

Autoantibodies to GFAP preferentially recognize GBDPs. Gels are loaded with human brain lysates and intact purified recombinant GFAP and probed with either an anti-GFAP (FIG. 24A) antibody, human post-TBI serum containing autoantibodies to GFAP (FIG. 24B), and or gels are stained with Coomassie blue (FIG. 23C). Autoantibodies show much greater recognition of GBDPs naturally derived from brain lysates than intact recombinant GFAP.

EXAMPLE 9

Detection of autoantibodies in studies of human TBI. Serum samples are obtained from human subjects following TBI at various timepoints. Table 10 illustrates the number of patients with samples provided at three different phases of TBI: acute+subacute phase (injury to day 10); severe TBI subacute phase (day 1 to day 30); and severe TBI—chronic phase (>1 mo post TBI).

TABLE 10

| | Cases | Auto-Antibody Positive | Percent (%) | 95% CI |
|---|---|---|---|---|
| Normal | 41 | 7 | 17.7 | 0.0821-0.3158 |
| Severe TBI (Day 1-10) acute + subacute phase | 28 | 21 | 75 | 0.5639-0.8758 |
| Severe TBI (Day 1, Day 7, Day 30) -subacute phase | 10 | 6 | 60 | 03116-0.8329 |
| Severe TBI (1 mo. To 3 yr. post injury)- chronic phase | 28 | 21 | 75 | 0.5639-0.8758 |

Confidence intervals are established by modified Wald methods. Overall, the number of TBI patients presenting with autoantibodies in their serum is much greater than normal controls.

The intensity of autoantibodies is measured by western blot using the procedures described in Example 8. An intensity level of 5 is scored the highest level of autoantibodies with an intensity level of zero representing no detectable autoantibody by the western blotting procedures. Healthy controls are compared to study samples obtained by Banyan Biomarkers, UP, and Italy study hosts. The majority of TBI patients had detectable levels of autoantibodies in their serum (FIG. 25).

EXAMPLE 10

An additional study of human subjects diagnosed with TBI is performed to analyze the correlation of the presence of autoantibodies with survival. Serum samples are obtained from twenty human subjects with severe (GCI score of 3-5) or mild (GCI score of 6-15) TBI. Table 11 illustrates the characteristics of subjects in the study.

TABLE 11

| TBI (HU-SZ) | |
|---|---|
| n | 20 |
| Age, years Mean (SD) | 52 ± 21 |
| Range | 24-86 |
| F/M, n (%) | 3/17 (15/85) |
| Ethnicity | |
| Not Hispanic or Latino | 20 |
| Race | |
| Caucasian | 20 |
| Best GCS | |
| 3-5 | 10 |
| 6-15 | 9 |
| Mechanism of injury: | |
| Motor vehicle | 7 |
| Motor cycle | 1 |
| Fall | 11 |
| Other | 1 |

Overall, 6 (30 percent) of subjects are negative for autoantibodies in their serum. Seventy percent show positive autoantibody development with 10 percent showing highly positive autoantibody levels as illustrated in Table 12.

TABLE 12

| Intensity | Frequency | Percent |
| --- | --- | --- |
| Negative | 6 | 30 |
| Positive(1-4) | 12 | 60 |
| Highly Positive (5) | 2 | 10 |

TABLE 13

| Survival 6 months | Frequency | Percent |
| --- | --- | --- |
| Favourable Outcome | 5 | 27.78 |
| Unfavourable Outcome | 13 | 72.22 |

Figure 26A:
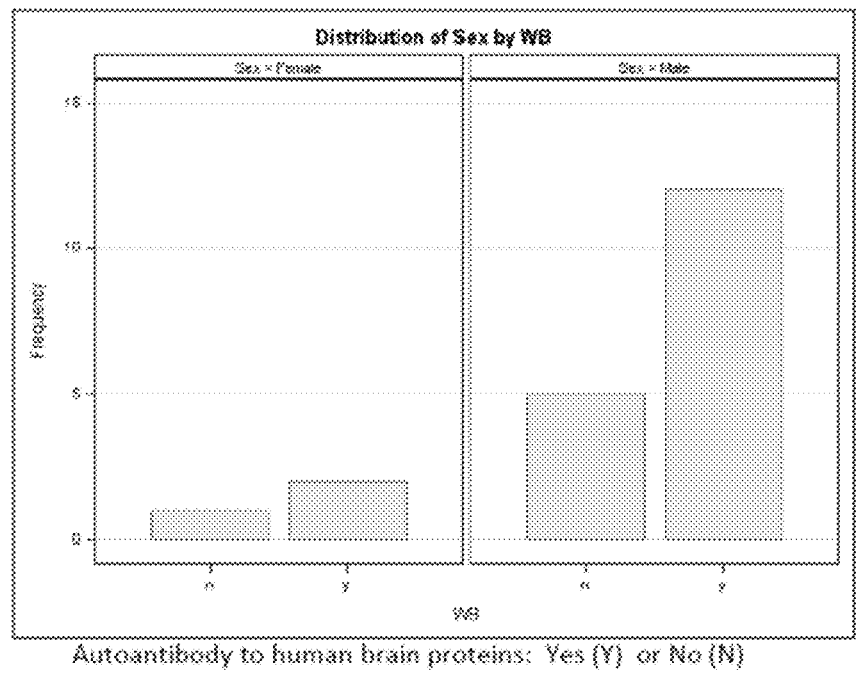
Figure 26B:
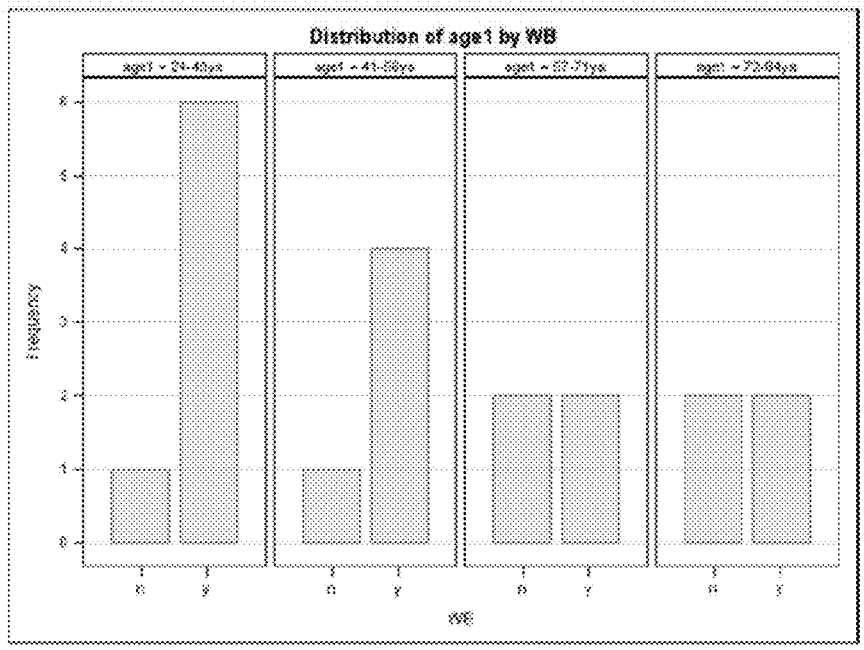

Overall, more male and female subjects present autoantibodies than not (FIG. 26A). Of subjects less than 56 years of age more present with autoantibodies than those who do not. For subjects from 57 to 71 years and 72 to 84 years two subjects present with autoantibodies and two subjects do not (FIG. 26B).

The presence of autoantibodies is relatively greater in subjects with a GCS score of 6-15 although more subjects with a GSC score of 3-5 are also autoantibody positive (FIG. 27). Interestingly, the subjects with unfavorable outcome (death <6 mo) show a higher propensity for the development of autoantibodies in serum than do subjects with a favorable outcome (FIG. 28). This indicates that the presence of autoantibodies correlates with survival.

The level of autoantibodies on the 5 point intensity scale correlates with the levels of GFAP and UCHL1 in serum taken within 24 hours of TBI. Serum samples from the human subjects taken within 24 hours after TBI are also analyzed for the presence and level of UCHL1, GFAP, and SBDP145 by ELISA essential as described in Example 2. These levels are then plotted against the intensity of autoantibodies. As depicted in FIG. 29 increased levels of GFAP and UCHL1 correlate with increased intensity of autoantibodies. GFAP correlates with a Pearson correlation coefficient of 0.72 and a P-value of 0.0009. UCHL1 correlates with a Pearson correlation of 0.56 and a P-value of 0.02.

Similar correlations are observed in CSF taken from human subjects within 24 hours after TBI. The level of GFAP correlates to later development of autoantibodies with a Pearson correlation of 0.47 and a P-value of 0.07. The levels of UCHL1 and autoantibody intensity correlate with a Pearson correlation of 0.56 and a P-value of 0.02. The level of SBDP145 also correlates with autoantibody intensity demonstrating a statistically significant Pearson correlation of 0.62 and a P-value of 0.01. (FIG. 30) Thus, the level of autoantibodies correlates with the level of soluble biomarker proteins in both serum and CSF in human subjects.

The relative abundance of autoantibodies in the subjects' serum is measured by western blot by similar techniques to those described in Example 9 with a maximal intensity level of 5. Overall, female subjects show a higher autoantibody intensity than do males (FIG. 31A). Among those with a favorable outcome (survival >6 mo.) male subjects have a higher autoantibody intensity than do females (FIG. 31B). Overall, while female subjects show reduced mortality, they also show higher autoantibody intensity and while males show higher mortality, the autoantibody intensity is lower (FIG. 31C). These data suggest that there is an inverse gender correlation between autoantibody intensity and outcome.

When the average intensity is correlated with survival independent of gender, there is no observable correlation between autoantibody intensity and survival of greater than 6 months (FIG. 32A). Thus, intensity functions as a predictor of outcome only on a gender dependent level. The presence of autoantibodies independent of their intensity also functions to predict outcome on a gender dependent level. Among female subjects, the presence of autoantibodies correlated with increased survival even thought the intensity is lower on average (FIG. 32B). Female non-survivors are less likely to show the presence of autoantibodies, yet the intensity is higher (FIG. 32B). Thus, among female study subjects the presence of low levels of autoantibodies suggests improved outcome relative to the presence of high levels of autoantibodies. Among male study subjects, while fewer study subjects with a favorable outcome show the presence of autoantibodies, those with a higher intensity are more likely to survive (FIG. 32C). Non-survivor males are more likely to have autoantibodies present, but their intensity is lower (FIG. 32C). Overall, the frequency and intensity of autoantibodies correlate with outcome in a gender dependent manner.

The intensity of autoantibodies does trend higher with the severity of TBI as measured by GCS score (FIG. 33). Subjects with a GCS value of 3 show much higher autoantibody intensity than do subjects with a higher GCS score of 7. A reducing trendline with increasing GCS score suggests that subjects with greater autoantibody intensity are more likely to have reduced GCS score and greater TBI severity.

EXAMPLE 11

Serum or CSF levels of nucleic acid biomarkers as a measure of neuronal injury. Just as proteins enter the CSF and plasma compartments after organ or brain injury, so do RNA and DNA. Cells undergoing apoptosis or necrosis release nucleic acid biomarkers into the blood or CSF (FIG. 34). The severity and site of injury is identifiable by appropriate real-time PCR assays to quantify the amount of cell type specific RNAs. Examples of neural-specific RNAs include beta III tubulin, UCHL1, GFAP, and synaptophysin.

Whole blood samples obtained from human subjects of the study of Example 7 are used to determine the level of nucleic acids encoding GFAP or UCHL1 therein. FIG. 35 illustrates the presence of increased serum GFAP and UCHL1 protein levels in subjects with severe TBI. To determine whether RNA encoding GFAP or UCHL1 is present in serum, analyses of serum by techniques similar to that described by Rainer, T H, et al., *Clin Chem,* 2003; 49:562-560, are used. Briefly, 10-mL of subject blood is withdrawn from the antecubital vein of each subject upon admission, collected into tubes containing EDTA, and double centrifuged at 3000×g for 15 min. Alternatively or in addition, the plasma is filtered to remove cellular material by centrifugation through a 0.2 micrometer filter. The supernatant cell free plasma is transferred into plain polypropylene tubes containing RNA/DNA Stabilization Reagent for Blood/Bone Marrow (Roche Diagnostics) and stored at −80° C. pending further processing.

Poly(A)$^+$ mRNA is extracted using the mRNA Isolation Kit for Blood and Bone Marrow (Roche Diagnostics) according to the manufacturer's protocol. cDNA is synthesized and amplified in a 50-μL PCR reaction using the Qiagen One Step RT-PCR reagent set (Qiagen). In brief, the mRNA in 6 μL of plasma is reverse-transcribed with specific primers for GFAP or UCHL1, using One Step RT-PCR enzyme mixture (Qiagen). The resulting cDNA is measured by Taqman assay using primers and probes for GFAP: forward primer—ACATCGAGATCGCCACCTACA (SEQ ID NO: 45); reverse primer—GTCTGCACGGGAATGGT-GAT (SEQ ID NO: 46); and labeled probe—AGCTGCTA-GAGGGCGAGGAGAACCG (SEQ ID NO: 47) using an annealing temperature of 60° C. as per the protocol of Pattyn, F, et al, *Nucleic Acids Research,* 2003; 31(1):122-123. For detection of UCHL1 the primers an probes are: forward primer—ACTGGGATTTGAGGATGGATCAG (SEQ ID NO: 48); reverse primer—GCCTTCCTGTGC-CACGG (SEQ ID NO: 49); labeled probe—AATGAGGC-CATACAGGCAGCCCATG (SEQ ID NO: 50) using an annealing temperature of 60° C. Overall, the presence of mRNA for both GFAP and UCHL1 are present in cell free plasma from subjects following TBI.

EXAMPLE 12

The presence of miRNAs related to TBI in humans is detected in human serum one day following TBI. Serum collected, made cell free by centrifugation at 3000×g for 15 min and moving through a 0.2 micrometer filter, and used to prepare total RNA. The total RNA (5 μg) is size fractionated (b300 nucleotides) by using a YM-100 Microcon centrifugal filter (Millipore). The collected small RNAs (b300 nt) are 3′-extended with a poly(A) tail using poly (A) polymerase. An oligonucleotide tag is ligated to the poly (A) tail for later fluorescent dye staining. The small RNAs are hybridized overnight on a μParaflo microfluidic chip using a micro-circulation pump (Atactic Technologies). Each detection probe on the chip consists of a chemically modified nucleotide coding segment complementary to target human miRNA sequences.

The miRNA sequences that show at least a two-fold increase or decrease in serum from TBI subjects versus serum from human control subjects are presented in Tables 14 and 15.

TABLE 14

Upregulated miRNA detected in human serum following TBI.

| S14_hsa_miRNA name | S14_hsa_miRNA_Sequence | SEQ ID NO: | S14_hsa_miRNA_MIMAT | Fold Change Up > 2 Serum TBI/ Serum Ctrl (Log2) |
|---|---|---|---|---|
| hsa-miR-744 | UGCGGGGCUAGGGCUAACAGCA | 51 | MIMAT0004945 | 2.22 |
| hsa-miR-762 | GGGGCUGGGGCCGGGGCCGAGC | 52 | MIMAT0010313 | 2.27 |
| hsa-miR-711 | GGGACCCAGGGAGAGACGUAAG | 53 | MIMAT0012734 | 2.41 |
| hsa-miR-484 | UCAGGCUCAGUCCCUCCCGAU | 54 | MIMAT0002174 | 2.46 |
| hsa-miR-765 | UGGAGGAGAAGGAAGGUGAUG | 55 | MIMAT0003945 | 2.58 |
| hsa-let-7b | UGAGGUAGUAGGUUGUGUGGUU | 56 | MIMAT0000063 | 2.61 |
| hsa-miR-663 | AGGCGGGGCGCCGCGGGACCGC | 57 | MIMAT0003326 | 2.90 |
| hsa-miR-30c-1* | CUGGGAGAGGGUUGUUUACUCC | 58 | MIMAT0004674 | 2.94 |
| hsa-let-7i | UGAGGUAGUAGUUUGUGCUGUU | 59 | MIMAT0000415 | 2.95 |
| hsa-miR-1246 | AAUGGAUUUUUGGAGCAGG | 60 | MIMAT0005898 | 3.02 |
| hsa-miR-1275 | GUGGGGAGAGGCUGUC | 61 | MIMAT0005929 | 3.88 |
| hsa-miR-1290 | UGGAUUUUUGGAUCAGGGA | 62 | MIMAT0005880 | 4.43 |
| hsa-miR-93 | CAAAGUGCUGUUCGUGCAGGUAG | 63 | MIMAT0000093 | 4.68 |
| hsa-miR-423-5p | UGAGGGGCAGAGAGCGAGACUUU | 64 | MIMAT0004748 | 4.75 |
| hsa-miR-1202 | GUGCCAGCUGCAGUGGGGAG | 65 | MIMAT0005865 | 5.90 |
| hsa-miR-198 | GGUCCAGAGGGGAGAUAGGUUC | 66 | MIMAT0000228 | 8.51 |
| hsa-miR-320c | AAAAGCUGGGUUGAGAGGGU | 67 | MIMAT0005793 | 11.13 |
| hsa-miR-320a | AAAAGCUGGGUUGAGAGGGCGA | 68 | MIMAT0000510 | 11.86 |
| hsa-miR-320b | AAAAGCUGGGUUGAGAGGGCAA | 69 | MIMAT0005792 | 12.83 |
| hsa-let-7c | UGAGGUAGUAGGUUGUAUGGUU | 70 | MIMAT0000064 | 14.07 |
| hsa-miR-24 | UGGCUCAGUUCAGCAGGAACAG | 71 | MIMAT0000080 | 14.81 |
| hsa-miR-320d | AAAAGCUGGGUUGAGAGGA | 72 | MIMAT0006764 | 14.91 |
| hsa-miR-486-5p | UCCUGUACUGAGCUGCCCCGAG | 73 | MIMAT0002177 | 16.85 |

TABLE 14-continued

Upregulated miRNA detected in human serum following TBI.

| S14_hsa_miRNA name | S14_hsa_miRNA_Sequence | SEQ ID NO: | S14_hsa_miRNA_MIMAT | Fold Change Up > 2 Serum TBI/ Serum Ctrl (Log2) |
|---|---|---|---|---|
| hsa-miR-425 | AAUGACACGAUCACUCCCGUUGA | 74 | MIMAT0003393 | 18.11 |
| hsa-miR-92a | UAUUGCACUUGUCCCGGCCUGU | 75 | MIMAT0000092 | 25.52 |
| hsa-let-7a | UGAGGUAGUAGGUUGUAUAGUU | 76 | MIMAT0000062 | 26.23 |
| hsa-miR-25 | CAUUGCACUUGUCUCGGUCUGA | 77 | MIMAT0000081 | 29.86 |
| hsa-miR-483-5p | AAGACGGGAGGAAAGAAGGGAG | 78 | MIMAT0004761 | 30.87 |
| hsa-miR-30d | UGUAAACAUCCCCGACUGGAAG | 79 | MIMAT0000245 | 33.21 |
| hsa-miR-185 | UGGAGAGAAAGGCAGUUCCUGA | 80 | MIMAT0000455 | 92.20 |
| hsa-miR-223 | UGUCAGUUUGUCAAAUACCCCA | 81 | MIMAT0000280 | 102.06 |
| hsa-miR-451 | AAACCGUUACCAUUACUGAGUU | 82 | MIMAT0001631 | 137.35 |
| hsa-miR-16 | UAGCAGCACGUAAAUAUUGGCG | 83 | MIMAT0000069 | 172.25 |

TABLE 15

Downregulated miRNA detected in human serum following TBI.

| S14_hsa_miRNA name | S14_hsa_miRNA_Sequence | SEQ ID NO: | S14_hsa_miRNA_MIMAT | Fold Change Down > 2 Serum TBI/ Serum Ctrl (Log2) |
|---|---|---|---|---|
| hsa-miR-675* | CUGUAUGCCCUCACCGCUCA | 84 | MIMAT0006790 | 0.27 |
| hsa-miR-1910 | CCAGUCCUGUGCCUGCCGCCU | 85 | MIMAT0007884 | 0.28 |
| hsa-miR-1181 | CCGUCGCCGCCACCCGAGCCG | 86 | MIMAT0005826 | 0.29 |
| hsa-miR-1972 | UCAGGCCAGGCACAGUGGCUCA | 87 | MIMAT0009447 | 0.30 |
| hsa-miR-1229 | CUCUCACCACUGCCCUCCCACAG | 88 | MIMAT0005584 | 0.30 |
| hsa-miR-634 | AACCAGCACCCCAACUUUGGAC | 89 | MIMAT0003304 | 0.31 |
| hsa-miR-449b* | CAGCCACAACUACCCUGCCACU | 90 | MIMAT0009203 | 0.31 |
| hsa-miR-885-5p | UCCAUUACACUACCCUGCCUCU | 91 | MIMAT0004947 | 0.35 |
| hsa-miR-1825 | UCCAGUGCCCUCCUCUCC | 92 | MIMAT0006765 | 0.35 |
| hsa-miR-532-3p | CCUCCCACACCCAAGGCUUGCA | 93 | MIMAT0004780 | 0.35 |
| hsa-miR-1224-3p | CCCCACCUCCUCUCUCCUCAG | 94 | MIMAT0005459 | 0.37 |
| hsa-miR-1260 | AUCCCACCUCUGCCACCA | 95 | MIMAT0005911 | 0.41 |
| hsa-miR-127-3p | UCGGAUCCGUCUGAGCUUGGCU | 96 | MIMAT0000446 | 0.41 |
| hsa-miR-1233 | UGAGCCCUGUCCUCCCGCAG | 97 | MIMAT0005588 | 0.42 |
| hsa-miR-636 | UGUGCUUGCUCGUCCCGCCCGCA | 98 | MIMAT0003306 | 0.42 |
| hsa-miR-1228 | UCACACCUGCCUCGCCCCCC | 99 | MIMAT0005583 | 0.43 |
| hsa-miR-197 | UUCACCACCUUCUCCACCCAGC | 100 | MIMAT0000227 | 0.43 |

TABLE 15-continued

Downregulated miRNA detected in human serum following TBI.

| S14_hsa_miRNA name | S14_hsa_miRNA_Sequence | SEQ ID NO: | S14_hsa_miRNA_MIMAT | Fold Change Down > 2 Serum TBI/ Serum Ctrl (Log2) |
|---|---|---|---|---|
| hsa-miR-1226 | UCACCAGCCCUGUGUUCCCUAG | 101 | MIMAT0005577 | 0.43 |
| hsa-miR-1296 | UUAGGGCCCUGGCUCCAUCUCC | 102 | MIMAT0005794 | 0.43 |
| hsa-miR-328 | CUGGCCCUCUCUGCCCUUCCGU | 103 | MIMAT0000752 | 0.44 |
| hsa-miR-1976 | CCUCCUGCCCUCCUUGCUGU | 104 | MIMAT0009451 | 0.45 |
| hsa-miR-574-3p | CACGCUCAUGCACACACCCACA | 105 | MIMAT0003239 | 0.46 |
| hsa-miR-766 | ACUCCAGCCCCACAGCCUCAGC | 106 | MIMAT0003888 | 0.46 |
| hsa-miR-1280 | UCCCACCGCUGCCACCC | 107 | MIMAT0005946 | 0.46 |
| hsa-miR-1470 | GCCCUCCGCCCGUGCACCCCG | 108 | MIMAT0007348 | 0.46 |
| hsa-miR-125b-1* | ACGGGUUAGGCUCUUGGGAGCU | 109 | MIMAT0004592 | 0.46 |
| hsa-miR-1227 | CGUGCCACCCUUUUCCCCAG | 110 | MIMAT0005580 | 0.47 |
| hsa-miR-615-3p | UCCGAGCCUGGGUCUCCCUCUU | 111 | MIMAT0003283 | 0.48 |
| hsa-miR-1225-3p | UGAGCCCCUGUGCCGCCCCCAG | 112 | MIMAT0005573 | 0.48 |
| hsa-miR-1285 | UCUGGGCAACAAAGUGAGACCU | 113 | MIMAT0005876 | 0.49 |

The identified sequences are subjected to a cluster analysis as depicted in FIG. 36.

Additional miRNAs with associated localizations are listed in Tables 16 and 17.

TABLE 16

Examples of brain specific or brain enriched miRNAs.

| MicroRNA Name | Brain region localization | Other characteristics |
|---|---|---|
| miR-92b | Ventral and dorsal subpallium, pallium, thalamus (dorsal (DT) and ventral (VT), hypothalamus, retectum, tegmentum and hindbrain as well as in the tectal proliferative zone, rhombic lip and retinal ciliary marginal zone | Neuronal precursors and stem cells |
| miR-124 | Larval brain and retina | Proliferation to differentiation |
| miR-124 | Mature neuron | |
| miR-222 | telecephalon | |
| miR-135 | Larval brain | |
| miR-9 | Telencephalic, diencephalic and tectal periventricular proliferative zones as well as the mature neuron | |
| miR-183 | Retinal photoreceptors, peripheral sensory neuromasts, olfactory sensory neurons and hair cells of the ear. | |
| miR-34, miR-218a | Habenular cells of the adult brain Motor neurons | |

Seven Human brain-specific miRNAs: miR-9, -124a, -124b, -135, -153, -183, -219
Seven human brain-enriched miRNAs: miR-9*, -125a, -125b, -128, -132, -137, -139

TABLE 17 miRNAs with putative targets and functions.

| miRNA | Putative mRNA targets | Function/disease |
|---|---|---|
| rno-miR-130a | synaptotagmin VI, CRMP-2 | polyQ disease |
| rno-miR-140* | CRMP-2, CAPN1 | TBI, MCAO |
| rno-miR-145 | CRMP-2, insulin receptor substrate-1 (IRS-1) | MCAO, colon cancer |
| rno-miR-135a | Synaptotagmin-1, Smad5 | Brain enriched, Colorectal Cancer |
| miR-124 | CAPN1, 2, 6, | Brain specific, neurogenesis |
| rno-miR-34b | MBP, synaptotagmin IX, Rho-kinase, p53 | Apoptosis/chronic lymphocytic leukemia |
| rno-miR-19b | SYTL1, calpastatin, synapsin I, CRMP-1, syntaphilin, ATXN1 | MCAO, TBI, polyQ disease |

The presence of miRNA associated with regulation of GFAP is also measured in cell free plasma samples as described above. The miRNA-125b is increased in subjects with degenerative neuronal conditions. Pogue, A I, et al, Neurosci. Lett., 2010; 476:18-22. Using the same primers and probes to detect miRNA-125b, increased levels of this miRNA are detected in cell free plasma from subjects following TBI. Briefly, total RNA from the cell free plasma is extracted with miRNeasy Mini kit (Qiagen, Valencia, Calif.) according to the manufacturer's instructions. RNA purity is determined by spectrophotometric determination at 260/280 nm and 260/230 nm. An absorbance ration of 260/280 nm greater than 1.8 is usually considered an acceptable indicator of RNA purity. 10 ng of total RNA from each sample is then reverse-transcribed to cDNA using TaqMan® MicroRNA Reverse Transcription Kit (Applied Biosystems, Foster City, Calif.) and miRNA specific primers (Applied Biosystems). The presence of the miRNAs identified by Dharap, A, and Vemuganti, R, *J. Neurochem.*, 2010; 113: 1685-1691 are detected in cell free plasma in TBI subjects as well as in an independent set of subjects following ischemic stroke. Also, the levels of the miRNAs identified by Lei, P, et al., *Brain Research,* 2009; 1284:191-201 are examined for presence in cell free plasma.

EXAMPLE 13

```
Sequence of human GFAP
                                                    (SEQ ID NO: 114)
   1    MERRRITSAA  RRSYVSSGEM  MVGGLAPGRR  LGPGTRLSLA  RMPPPLPTRV  DFSLAGALNA

61    GFKETRASER  AEMMELNDRF  ASYIEKVRFL  EQQNKALAAE  LNQLRAKEPT  KLADVYQAEL

121    RELRLRLDQL  TANSARLEVE  RDNLAQDLAT  VRQKLQDETN  LRLEAENNLA  AYRQEADEAT

181    LARLDLERKI  ESLEEEIRFL  RKIHEEEVRE  LQEQLARQQV  HVELDVAKPD  LTAALKEIRT

241    QYEAMASSNM  HEAEEWYRSK  FADLTDAAAR  NAELLRQAKH  EANDYRRQLQ  SLTCDLESLR

301    GTNESLERQM  REQEERHVRE  AASYQEALAR  LEEEGQSLKD  EMARHLQEYQ  DLLNVKLALD

361    IEIATYRKLL  EGEENRITIP  VQTFSNLQIR  ETSLDTKSVS  EGHLKRNIVV  KTVEMRDGEV

421    IKESKQEHKD  VM
```

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

REFERENCE LIST

Leon, S A et al (1977) Patients Cancer Research 37, 646
Muller, H. M. et al (2003) Expert Rev Mol. Diagn. 3, 443
Silva, J M et al (1999) Cancer Research, 59, 3251
Lo, Y M et al (1997) Lancet
Menke, T M and Warnecke, J M (2004) Ann NY Acad. Sci 1022, 185-189.
Hasselmann, D. O. et al (2001) Extracellular tyrosinase mRNA within apoptotic bodies is protected from degradation in human serum. Clin. Chem. 47: 1488-1489.
Circulating Nucleic acids in plasma and Serum (CNAPS) III and serum proteomics. Ann NY Acad Sci 1022 (Eds. D. S. B. Hoon, B. Taback).
Tan E. M. et al. 1966 Deoxyribonucleic acid (DNA) and antibodies to DNA in the serum of patients with systemic lupus erythematosus. J. Clin. Invest. 45:1732-1740.
Rainer, T H et al (2003) Prognostic use of circulating plasma nucleic acid concentrations in patients with acute stroke. Clin Chem. 49:562-560.
Hmaouim K., Butt, A., Powrie, J., and Swaminathan, R. (2004) Real-time Quantitative PCR Measurement of Circulatory Rhodopsin mRNA in Healthy Subjects and Patients with Diab etic Retinopathy. In Circulating Nucleic acids in plasma and Serum (CNAPS) III and serum proteomics. Ann NY Acad Sci 1022 (Eds. D. S. B. Hoon, B. Taback). Pp 152-156.
Rainer, T H et al (2004) Effects of filtration on glyceraldehydes –3-phosphate dehydrogenase mRNA in the plasma of trauma patients and healthy individuals. Clin. Chem. 50:206-208.
Terryberry J W, Thor G, Peter J B. (1998) Autoantibodies in neurodegenerative diseases: antigen-specific frequencies and intrathecal analysis. Neurobiol Aging 19:205-216.
Terryberry J W, Shoenfeld Y, Peter J B. (1998) Clinical utility of autoantibodies in Guillain-Barre syndrome and its variants. Clin Rev Allergy Immunol 16:265-273.
Dambinova S A, Khounteev G A, Izykenova G A, Zavolokov I G, Ilyukhina A Y, Skoromets A A. (2003) Blood test detecting autoantibodies to N-methyl-D-aspartate neuroreceptors for evaluation of patients with transient ischemic attack and stroke. Clin Chem 49:1752-1762.
Dambinova S A, Izykenova G A, Burov S V, Grigorenko E V, Gromov S A. (1997) The presence of autoantibodies to N-terminus domain of GluR1 subunit of AMPA receptor in the blood serum of patients with epilepsy. J Neurol Sci 152:93-97.
Goryunova A V, Bazarnaya N A, Sorokina E G, et al. (2007) Glutamate receptor autoantibody concentrations in children with chronic post-traumatic headache. Neurosci Behav Physiol 37:761-764.
ADAMS, J. H., GRAHAM, D. I., and JENNETT, B. (2000). The neuropathology of the vegetative state after an acute brain insult. Brain. 123, 1327-1338.
ARNAUD L T, MYEKU N, FIGUEIREDO-PEREIRA M E. (2009) Proteasome-caspase-cathepsin sequence leading to tau pathology induced by prostaglandin J2 in neuronal cells. J Neurochem. 2009 110(1):328-42.
AVILA, J., PEREZ, M., LUCAS, J. J., GOMEZ-RAMOS, A., MARIA, I. S., MORENO, F., SMITH, M., PERRY, G., and HERNANDEZ, F. (2004). Assembly in vitro of tau protein and its implications in Alzheimer's disease. Curr Alzheimer Res. 1, 97-101.
BARTUS, R. T. (1997). The calpain hypothesis of neurodegeneration: evidence for a common cytotoxic pathway. The Neuroscientist. 3, 314-327.
BEER, R., FRANZ, G., SRINIVASAN, A., HAYES, R. L., PIKE, B. R., NEWCOMB, J. K., ZHAO, X., SCHMUTZHARD, E., POEWE, W., and KAMPFL, A. (2000). Temporal profile and cell subtype distribution of activated caspase-3 following experimental traumatic brain injury. Neurochem. 75, 1264-1273.

BINDER, L. I., FRANKFURTER, A., and REBHUN, L. I. (1985). The distribution of tau in the mammalian central nervous system. J. Cell Biol. 101, 1371-1378.

BITSCH, A., HORN, C., KEMMLING, Y., SEIPELT, M., HELLENBRND, U., STIEFEL, M., CIESIELCZYK, B., CEPEK, L., BAHN, E., RATZKA, P., PRANGE, H., and OTTO, M. (2002). Serum tau protein level as a marker of axonal damage in acute ischemic stroke. Eur. Neurol. 47, 45-51.

BRAMLETT, H. M., and DIETRICH, W. D. (2002). Quantitative structural changes in white and gray matter 1 year following traumatic brain injury in rats. Acta Neuropathol. (Berl). 103, 607-614.

BUKI, A., OKONKWO, D. O., WANG K. K. W., and POVLISHOCK, J. T. (2000) Cytochrome c release and caspase activation in traumatic axonal injury. J. Neurosci. 20, 2825-2834.

BUKI, A., SIMAN, R., TROJANOWSKI, J. Q., and POVLISHOCK, J. T. (1999). The role of calpain-mediated spectrin proteolysis in traumatically induced axonal injury. J. Neuropathol. Exp. Neurol. 58, 365-375.

BARTUS, R. T. (1997). The calpain hypothesis of neurodegeneration: evidence for a common cytotoxic pathway. The Neuroscientist. 3, 314-327.

CANU, N., DUS, L., BARBATO, C., CIOTTI, M. T., BRANCOLINI, C., RINALDI A. M., NOVAK, M., CATTANEO, A., BRADBURY A., and CALISSANO, P. (1998). Tau cleavage and dephosphorylation in cerebellar granule neurons undergoing apoptosis. J. Neurosci. 8, 7061-7074.

CHRISTMAN, C. W., GRADY, M. S., WALKER, S. A., HOLLOWAY, K. L., and POVLISHOCK, J. T. (1994). Ultrastructural studies of diffuse axonal injury in humans. J. Neurotrauma. 11, 173-186.

CHUNG, C. W., SONG, Y. H., KIM, I. K., YOON, W. J., RYE, B. R., JO, D. G., WOO, H. N., KWON, Y. K., KIM, H. H., GWAG, B. J., MOOK-JUNG, I. H., and JUNG, Y. K. (2001). Proapoptotic effects of tau cleavage product generated by caspase-3. Neurobiol. Dis. 8, 162-172.

CLARK, R. S., KOCHANEK, P. M., WATKINS, S. C., CHEN, M., DIXON, C. E., SEIDBERG, N. A., MELICK, J., LOEFFERT, J. E., NATHANIEL, P. D., JIN, K. L., and GRAHAM, S. H. (2000). Caspase-3 mediated neuronal death after traumatic brain injury in rats. J. Neurochem. 74, 740-753.

DELOBEL P, LEROY O, HAMDANE M, SAMBO A V, DELACOURTE A, BUÉE L. (2005) Proteasome inhibition and Tau proteolysis: an unexpected regulation. FEBS Lett. 579, 1-5.

DIXON, C. E., CLIFTON, G. L., LIGHTHALL J. W., YAGHMAI, A. A., and HAYES, R. L. (1991). A controlled cortical impact model of traumatic brain injury in the rat. J. Neurosci. 39, 253-262.

DRUBIN, D. G., and KIRSCHNER, M. W. (1986). Tau protein function in living cells. J. Cell Biol. 103, 2739-2746.

FRANZ, G., BEER, R., KAMPFL, A., ENGELHARDT, K., SCHMUTZHARD, E., ULMER, H., and DEISENHAMMER, F. (1995). Amyloid beta 1-42 and tau in cerebrospinal fluid after severe traumatic brain injury. Neurology. 60, 1457-1461.

GABBITA S P, SCHEFF S W, MENARD R M, ROBERTS K, FUGACCIA I, ZEMLAN F P. (2005) Cleaved-tau: a biomarker of neuronal damage after traumatic brain injury. J Neurotrauma. 22, 83-94.

GAMBLIN T C, CHEN F, ZAMBRANO A, ABRAHA A, LAGALWAR S, GUILLOZET A L, LU M, FU Y, GARCIA-SIERRA F, LAPOINTE N, MILLER R, BERRY R W, BINDER L I, CRYNS V L. Caspase cleavage of tau, linking amyloid and neurofibrillary tangles in Alzheimer's disease. Proc Natl Acad Sci USA 100, 10032-10037.

GARCÍA-SIERRA F, MONDRAGÓN-RODRÍGUEZ S, BASURTO-ISLAS G. (2008). Truncation of tau protein and its pathological significance in Alzheimer's disease. J Alzheimers Dis. 14, 401-9.

GALE, S. D., JOHNSON, S. C., BIGLER, E. D., and BLATTER, D. D. (1995). Nonspecific white matter degeneration following traumatic brain injury. J. Int. Neuropsychol. Soc. 1, 17-28.

GARCIA, M. L., and CLEVELAND, D. W. (2001). Going new places using an old MAP: tau, microtubules and human neurodegenerative diseases. Curr. Opin. Cell Biol. 13, 41-48.

GUILLOZET-BONGAARTS A L, GARCIA-SIERRA F, REYNOLDS M R, HOROWITZ P M, FU Y, WANG T, CAHILL M E, BIGIO E H, BERRY R W, BINDER L I. (2005) Tau truncation during neurofibrillary tangle evolution in Alzheimer's disease. Neurobiol Aging. 26, 1015-1022.

HIGUCHI, M., LEE, V. M., and TROJANOWSKI, J. Q. (2002). Tau and axonopathy in neurodegenerative disorders. Neuromolecular Med. 2, 131-150.

JOHNSON, G. V., JOPE, R. S., and BINDER, L. I. (1989). Proteolysis of tau by calpain. Biochem. Biophys. Res. Commun. 163, 1505-1511.

KAMPFL, A., POSMANTUR, R. M., ZHAO, X., SCHMUTZHARD, E., CLIFTON, G. L., and HAYES R. L. (1997). Mechanisms of calpain proteolysis following traumatic brain injury: implications for pathology and therapy: a review and update. J. Neurotrauma 14, 121-134.

KIRALY M, KIRALY S J. (2007) Traumatic brain injury and delayed sequelae: a review—traumatic brain injury and mild traumatic brain injury (concussion) are precursors to later-onset brain disorders, including early-onset dementia. ScientificWorldJournal. 2007 Nov. 12; 7:1768-76.

KNOBLACH, S. M., NIKOLAEVA, M., HUANG, X., FAN, L., KRAJEWSKI, S., REED, J. C., and FADEN, A. I. (2002). Multiple caspases are activated after traumatic brain injury: evidence for involvement in functional outcome. J. Neurotrauma 19, 1155-1170.

Kosik, K. S., and Finch, E. A. (1987). MAP2 and tau segregate into dendritic and axonal domains after the elaboration of morphologically distinct neurites: an immunocytochemical study of cultured rat cerebrum. J. Neurosci. 7, 3142-3153.

KÖVESDI E, LÜCKL J, BUKOVICS P, FARKAS O, PÁL J, CZEITER E, SZELLÁR D, DÓCZI T, KOMOLY S, BÜKI A. (2010). Update on protein biomarkers in traumatic brain injury with emphasis on clinical use in adults and pediatrics. Acta Neurochir (Wien). 152(1):1-17.

KRISHNAMURTHY, S., and SNEIGE, N. (2002). Molecular and biologic markers of premalignant lesions of human breast. Adv. Anat. Pathol. 9, 185-197.

LITERSKY, J. M., SCOTT, C. W., and JOHNSON, G. V. (1993). Phosphorylation, calpain proteolysis and tubulin binding of recombinant human tau isoforms. Brain Res. 604, 32-40.

MCCRACKEN, E., HUNTER, A. J., PATEL, S., GRAHAM, D. I., and DEWAR, D. (1999). Calpain activation and cytoskeletal protein breakdown in the corpus callosum of head-injured patients. J Neurotrauma 16, 749-761.

MCINTOSH, T. K., SMITH, D. H., MEANEY, D. F., KOTAPKA, M. J., GENNARELLI, T. A., and GRAHAM, D. I. (1996). Neuropathological sequelae of traumatic brain injury: relationship to neurochemical and biomechanical mechanisms. Lab. Invest. 74, 315-341.

MCKEE A C, CANTU R C, NOWINSKI C J, HEDLEY-WHYTE E T, GAVETT B E, BUDSON A E, SANTINI V E, LEE H S, KUBILUS C A, STERN R A. (2009). Chronic traumatic encephalopathy in athletes: progressive tauopathy after repetitive head injury. J Neuropathol Exp Neurol. 68(7):709-35.

MEDANA, I. M., and ESIRI, M. M. (2003). Axonal damage: a key predictor of outcome in human CNS diseases. Brain. 126, 515-530.

NATH, R., MCGINNIS, K. J., NADIMPALLI, R., STAFFORD, D., and WANG, K. K. W. (1996). Effects of ICE-like proteases and calpain inhibitors on neuronal apoptosis. NeuroReport. 8, 249-255.

NATH, R., PROBERT, A., JR., MCGINNIS, K. M., WANG, K. K. W. (1998) Evidence for Activation of Caspase-3-like Protease in Excitotoxins- and Hypoxia/hypoglycemia-Injured Neurons. J. Neurochem. 71, 186-195.

Newcomb J K, Kampfl A, Posmantur R M, Zhao X, Pike B R, Liu S J, Clifton G L, and Hayes R L. (1997) Immunohistochemical study of calpain-mediated breakdown products to alpha-spectrin following controlled cortical impact injury in the rat. J. Neurotrauma. 14, 369-383.

NG, H. K., MAHALIYANA, R. D., and POON, W. S. (1994). The pathological spectrum of diffuse axonal injury in blunt head trauma: assessment with axon and myelin strains. Clin. Neurol. Neurosurg. 96, 24-31.

PARK S Y, FERREIRA A. (2005) The generation of a 17 kDa neurotoxic fragment: an alternative mechanism by which tau mediates beta-amyloid-induced neurodegeneration. J Neurosci. 25, 5365-5375.

PETTUS, E. H., CHRISTMAN, C. W., GIEBEL, M. L., and POVLISHOCK, J. T. (1994). Traumatically induced altered membrane permeability: its relationship to traumatically induced reactive axonal change. J. Neurotrauma. 11, 507-522.

PIKE, B. R., ZHAO, X., NEWCOMB, J. K., WANG, K. K. W., POSMANTUR, R. M., and HAYES, R. L. (1998b). Temporal relationships between de novo protein synthesis, calpain and caspase 3-like protease activation, and DNA fragmentation during apoptosis in septo-hippocampal cultures. J. Neurosci. Res. 52, 505-520.

PIKE, B. R., ZHAO, X., NEWCOMB, J. K., POSMANTUR, R. M., WANG, K. K. W., and HAYES, R. L. (1998). Regional calpain and caspase-3 proteolysis of alpha-spectrin after traumatic brain injury. NeuroReport. 9, 2437-2442.

PIKE, B. R., FLINT, J., DAVE, J. R., LU, X. C., WANG, K. K., TORTELLA, F. C., and HAYES, R. L. (2004). Accumulation of calpain and caspase-3 proteolytic fragments of brain-derived alphaII-spectrin in cerebral spinal fluid after middle cerebral artery occlusion in rats. J Cereb Blood Flow Metab. 24, 98-106.

POSMANTUR, R., KAMPFL, A., SIMAN, R., LIU, J., ZHAO, X., CLIFTON, G. L., and HAYES R. L. (1997). A calpain inhibitor attenuates cortical cytoskeletal protein loss after experimental traumatic brain injury in the rat. Neuroscience. 77, 875-88.

RAO M V, MOHAN P S, PETERHOFF C M, YANG D S, SCHMIDT S D, STAVRIDES P H, CAMPBELL J, CHEN Y, JIANG Y, PASKEVICH P A, CATALDO A M, HAROUTUNIAN V, NIXON R A. (2008). Marked calpastatin (CAST) depletion in Alzheimer's disease accelerates cytoskeleton disruption and neurodegeneration: neuroprotection by CAST overexpression. J Neurosci. 28(47):12241-54.

RISSMAN R A, POON W W, BLURTON-JONES M, ODDO S, TORP R, VITEK M P, LAFERLA F M, ROHN T T, COTMAN C W. (2004) Caspase-cleavage of tau is an early event in Alzheimer disease tangle pathology. J Clin Invest. 114(1), 121-30.

ROHN, T. T., RISSMAN, R. A., HEAD, E., and COTMAN, C. W. (2002). Caspase Activation in the Alzheimer's Disease Brain: Tortuous and Torturous. Drug News Perspect. 15, 549-557.

SAATMAN, K. E., BOZYCZKO-COYNE, D., MARCY, V., SIMAN, R., and MCINTOSH, T. K. (1996). Prolonged calpain-mediated spectrin breakdown occurs regionally following experimental brain injury in the rat. J. Neuropathol. Exp. Neurol. 55, 850-860.

SAATMAN, K. E., MURAL H., BARTUS, R. T., SMITH, D. H., HAYWARD, N. J., PERRI, B. R., and MCINTOSH T. K. (1996). Calpain inhibitor AK295 attenuates motor and cognitive deficits following experimental brain injury in the rat. Proc. Natl Acad. Sci. USA 93, 3428-3433.

SAATMAN, K. E, ZHANG, C., BARTUS, R. T., and MCINTOSH, T. K. (2000). Behavioral efficacy of post-traumatic calpain inhibition is not accompanied by reduced spectrin proteolysis, cortical lesion, or apoptosis. J. Cereb. Blood Flow Metab. 20, 66-73.

SHIMOHAMA S, TANINO H, FUJIMOTO S. (1999) Changes in caspase expression in Alzheimer's disease: comparison with development and aging. Biochem Biophys Res Commun. 256, 381-384.

SIMAN R, MCINTOSH T K, SOLTESZ K M, CHEN Z, NEUMAR R W, ROBERTS V L. (2004) Proteins released from degenerating neurons are surrogate markers for acute brain damage. Neurobiol Dis. 16(2), 311-20.

SINJOANU R C, KLEINSCHMIDT S, BITNER R S, BRIONI J D, MOELLER A, FERREIRA A. (2008). The novel calpain inhibitor A-705253 potently inhibits oligomeric beta-amyloid-induced dynamin 1 and tau cleavage in hippocampal neurons. Neurochem Int. 53(3-4):79-88.

URYU K, CHEN X H, MARTINEZ D, BROWNE K D, JOHNSON V E, GRAHAM D I, LEE V M, TROJANOWSKI J Q, SMITH D H. (2007) Multiple proteins implicated in neurodegenerative diseases accumulate in axons after brain trauma in humans. Exp Neurol. 208, 185-92.

VAN DEN HEUVEL C, THORNTON E, VINK R. (2007) Traumatic brain injury and Alzheimer's disease: a review. Prog Brain Res. 161:303-16.

WANG, K. K. W. (2000). Calpain and caspase: can you tell the difference? Trends Neurosci. 23, 20-26.

WARREN, M. W., KOBEISSY, F. H., HAYES, R. L., GOLD, M. S., WANG, K. K. W. (2005) Concurrent calpain and caspase-3 mediated proteolysis of αII-spectrin and tau in rat brain after methamphetamine exposure: A similar profile to traumatic brain injury. Life Sciences 78: 301-309.

WARREN, M W. ZHENG, W. R., KOBEISSY, F., LIU, M. C., HAYES, R. L., GOLD, MARK, M. C. LIU, AND WANG, K. K. W. (2006) Calpain and caspase mediated proteolysis of αII-spectrin and tau in rat cerebrocortical neuron cultures after ecstasy (MDMA) or methamphetamine exposure Int. J. Neuropsypharm. 9, 1-11.

YANG L. S., and KSIEZAK-REDING, H. (1995). Calpain-induced proteolysis of normal human tau and tau associated with paired helical filaments. J. Biochem. 233, 9-17.

YEN, S., EASSON, C., NACHARAJU, P., HUTTON, M., and YEN, S. H. (1999). FTDP-17 tau mutations decrease the susceptibility of tau to calpain I digestion. FEBS Lett. 461, 91-95.

YOSHIYAMA Y, URYU K, HIGUCHI M, LONGHI L, HOOVER R, FUJIMOTO S, MCINTOSH T, LEE V M, TROJANOWSKI J Q. (2005) Enhanced neurofibrillary tangle formation, cerebral atrophy, and cognitive deficits induced by repetitive mild brain injury in a transgenic tauopathy mouse model. J Neurotrauma. 22, 134-1141.

ZEMLAN, F. P., JAUCH, E. C., MULCHAHEY, J. J., GABBITA, S. P., and ROSENBERG, W. S. Speciale S G, and Zuccarello M. (2002). C-tau biomarker of neuronal damage in severe brain injured patients: association with elevated intracranial pressure and clinical outcome. Brain Res. 23, 131-139.

ZEMLAN, F. P., MULCHAHEY, J. J., and GUDELSKY, G. A. (2003). Quantification and localization of kainic acid-induced neurotoxicity employing a new biomarker of cell death: cleaved microtubule-associated protein-tau (C-tau). Neuroscience 121, 399-409.

ZHANG J Y, PENG C, SHI H, WANG S, WANG Q, WANG J Z. (2009) Inhibition of autophagy causes tau proteolysis by activating calpain rat brain. J Alzheimers Dis. 16, 39-47.

ZHANG Z, LARNER S, LIU M C, ZHENG W, HAYES R L, WANG K K W. (2009) Multiple αII-spectrin Breakdown Products Distinguish Calpain and Caspase Dominated Necrotic and Apoptotic Cell Death Pathways. Apoptosis, 14, 1289-1298.

The invention claimed is:

1. A process for detecting an autoantibody to glial fibrillary acid protein (GFAP) or a breakdown product thereof comprising: measuring an autoantibody to GFAP or an autoantibody to a GFAP breakdown product in a sample obtained from a subject presenting with clinical symptoms of a traumatic brain injury by contacting the sample with GFAP or a GFAP breakdown product and detecting binding between the autoantibody to GFAP and GFAP or between the autoantibody to the GFAP breakdown product and the GFAP breakdown product, wherein the GFAP is set forth in SEQ ID NO: 114, and wherein the GFAP breakdown product is within 10 amino acids of the cleavage site at amino acid position 59 or 383 set forth in SEQ ID NO: 114.

2. The process of claim 1, wherein the GFAP breakdown product is selected from the group consisting of: SEQ ID NO: 3, SEQ ID NO: 139, SEQ ID NO: 140, SEQ ID NO: 4, SEQ ID NO: 141, and SEQ ID NO: 142.

3. The process of claim 1, wherein the GFAP or GFAP breakdown product is detectably labeled.

4. The process of claim 1, wherein the sample is blood, serum, plasma, CSF, urine, saliva or tissue.

5. The process of claim 1, wherein the sample is blood, serum, or plasma.

6. The process of claim 1, wherein the binding between the autoantibody to GFAP and GFAP or between the autoantibody to the GFAP breakdown product and the GFAP breakdown product is detected using an enzyme linked immunosorbent assay (ELISA) or a western blot.

7. The process of claim 1, wherein the sample is obtained at least five days after the subject suffers the TBI.

8. The process of claim 1, wherein the sample is obtained up to 30 days after the subject suffers the TBI.

9. The process of claim 1, further comprising administering a therapeutic to the subject if binding between the autoantibody to GFAP and GFAP or between the autoantibody to the GFAP breakdown product and the GFAP breakdown product is detected.

10. The process of claim 9, further comprising:
detecting whether an autoantibody to glial fibrillary acidic protein (GFAP) or an autoantibody to a GFAP breakdown product is present in an additional sample obtained from the subject by contacting the additional sample with GFAP or a GFAP breakdown product and detecting binding between the autoantibody to GFAP and GFAP or between the autoantibody to the GFAP breakdown product and the GFAP breakdown product, wherein the GFAP is set forth in SEQ ID NO: 114 and wherein the GFAP breakdown product is within 10 amino acids of the cleavage site at amino acid position 59 or 383 set forth in SEQ ID NO: 114.

11. The process of claim 1, further comprising:
detecting whether an autoantibody to glial fibrillary acidic protein (GFAP) or an autoantibody to a GFAP breakdown product is present in an additional sample obtained from the subject by contacting the additional sample with GFAP or a GFAP breakdown product and detecting binding between the autoantibody to GFAP and GFAP or between the autoantibody to the GFAP breakdown product and the GFAP breakdown product, wherein the GFAP is set forth in SEQ ID NO: 114 and wherein the GFAP breakdown product is within 10 amino acids of the cleavage site at amino acid position 59 or 383 set forth in SEQ ID NO: 114.

* * * * *